(12) United States Patent
Varchi et al.

(10) Patent No.: US 8,859,599 B2
(45) Date of Patent: Oct. 14, 2014

(54) ANDROGEN RECEPTOR MODULATING COMPOUNDS, PREPARATION AND USES THEREOF

(75) Inventors: Greta Varchi, Bologna (IT); Andrea Guerrini, Bologna (IT); Anna Tesei, Meldola (IT); Giovanni Brigliadori, Meldola (IT)

(73) Assignees: CNR—Consiglio Nazionale delle Ricerche, Rome (IT); Istituto Scientifico Romagnolo per lo Studio e la Cura dei Tumori (I.R.S.T.) S.r.l., Meldola (FC) (IT)

( * ) Notice: Subject to any disclaimer, the term of this patent is extended or adjusted under 35 U.S.C. 154(b) by 240 days.

(21) Appl. No.: 13/144,566

(22) PCT Filed: Feb. 11, 2010

(86) PCT No.: PCT/IB2010/050636
§ 371 (c)(1),
(2), (4) Date: Jul. 14, 2011

(87) PCT Pub. No.: WO2010/092546
PCT Pub. Date: Aug. 19, 2010

(65) Prior Publication Data
US 2011/0275829 A1    Nov. 10, 2011

(30) Foreign Application Priority Data
Feb. 13, 2009    (IT) .............................. BO2009A0078

(51) Int. Cl.
*A61K 31/34*    (2006.01)
*A61K 31/343*    (2006.01)
(Continued)

(52) U.S. Cl.
USPC ........... 514/365; 514/307; 514/311; 514/357; 514/361; 514/367; 514/383; 514/393; 514/396; 514/408; 514/412; 514/438; 514/443; 514/461; 514/469; 544/242; 546/139; 546/152; 546/329; 548/125; 548/146; 548/152; 548/255; 548/300.1; 548/302.7; 548/400; 548/452; 549/29; 549/32; 549/429; 549/462

(58) Field of Classification Search
USPC ........... 544/242; 546/139, 152, 329; 548/125, 548/146, 152, 255, 200.1, 302.7, 400, 452; 549/29, 32, 429, 462; 514/307, 311, 514/357, 361, 365, 367, 383, 393, 396, 408, 514/412, 438, 443, 461, 469
See application file for complete search history.

(56) References Cited

U.S. PATENT DOCUMENTS
2005/0277628 A1    12/2005    Pfau et al.

FOREIGN PATENT DOCUMENTS
WO    2005/039506 A2    5/2005
WO    2005/049580 A1    6/2005
(Continued)

OTHER PUBLICATIONS
STN CAPLUS abstract of Greiciute et al, Phosphorous and Sulfur and the Related Elements (1977).*
(Continued)

*Primary Examiner* — Kamal Saeed
*Assistant Examiner* — Janet L Coppins
(74) *Attorney, Agent, or Firm* — Lucas & Mercanti, LLP

(57) ABSTRACT

The present invention concerns compounds of general formula (I): Method of preparation and uses thereof.

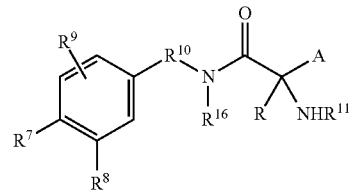

10 Claims, 27 Drawing Sheets

| [μM] | % net growth |
|------|--------------|
| 0,02 | 96,9 |
| 0,2 | 80,3 |
| 2 | 46,7 |
| 20 | 46,0 |

(R)-Bicalutamide

(51) Int. Cl.

| | | |
|---|---|---|
| *A61K 31/381* | (2006.01) | |
| *A61K 31/40* | (2006.01) | |
| *A61K 31/404* | (2006.01) | |
| *A61K 31/4164* | (2006.01) | |
| *A61K 31/4184* | (2006.01) | |
| *A61K 31/4192* | (2006.01) | |
| *A61K 31/426* | (2006.01) | |
| *A61K 31/428* | (2006.01) | |
| *A61K 31/433* | (2006.01) | |
| *A61K 31/435* | (2006.01) | |
| *A61K 31/47* | (2006.01) | |
| *A61K 31/505* | (2006.01) | |
| *C07D 207/30* | (2006.01) | |
| *C07D 209/04* | (2006.01) | |
| *C07D 213/24* | (2006.01) | |
| *C07D 215/12* | (2006.01) | |
| *C07D 217/02* | (2006.01) | |
| *C07D 233/56* | (2006.01) | |
| *C07D 235/04* | (2006.01) | |
| *C07D 239/24* | (2006.01) | |
| *C07D 249/02* | (2006.01) | |
| *C07D 285/02* | (2006.01) | |
| *C07D 277/22* | (2006.01) | |
| *C07D 277/62* | (2006.01) | |
| *C07D 307/36* | (2006.01) | |
| *C07D 307/78* | (2006.01) | |
| *C07D 333/02* | (2006.01) | |
| *C07D 333/52* | (2006.01) | |

(56) References Cited

FOREIGN PATENT DOCUMENTS

| | | | |
|---|---|---|---|
| WO | WO-2005/049580 A1 * | 6/2005 | |
| WO | 2007/137874 A2 | 12/2007 | |

OTHER PUBLICATIONS

Ducry, L., et al.: "Synthesis of 1,2,5-thiadizolidin-3-one 1, 1-dioxide derivatives and evaluation of their affinity for MHC class-II proteins", Helvetica Chimica Acta, Verlag Helvetica Chimica Acta., Basel, CH, vol. 82, No. 12, Jan. 1, 1999, pp. 2432-2447.

Payen, O., et al: "Synthesis and structure-activity relationships of the first ferrocenyl-aryl-hydantoin derivatives of the nonsteroidal antiandrogen nilutamide", Journal of Medicinal Chemistry, vol. 51, 2008, pp. 1791-1799.

* cited by examiner

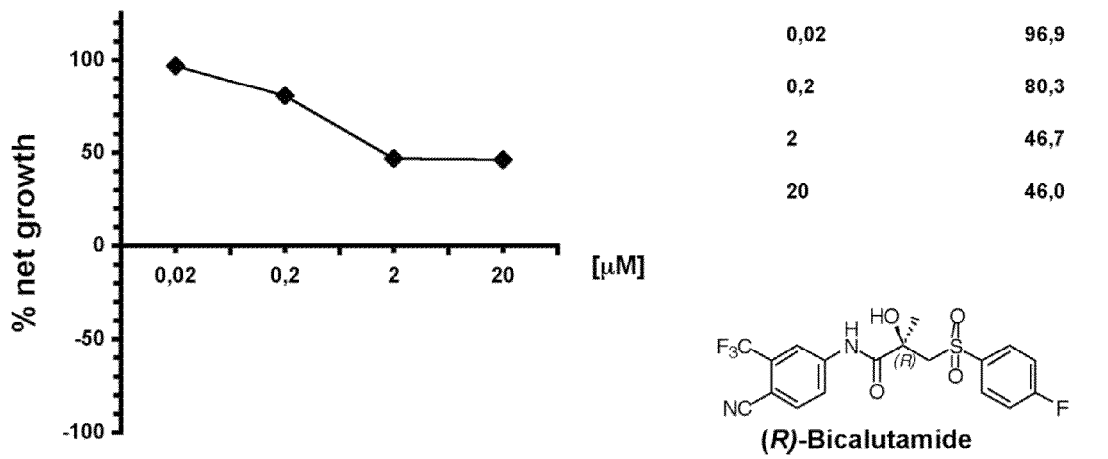
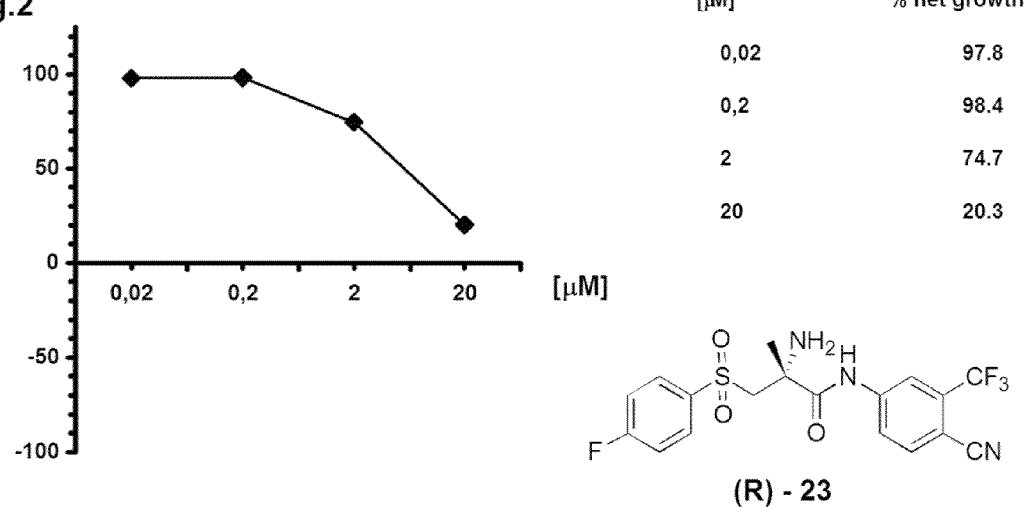

| [μM] | % net growth |
|---|---|
| 0,02 | 87.1 |
| 0,2 | 86.4 |
| 2 | 74.5 |
| 20 | 31.3 |

| [μM] | % net growth |
|---|---|
| 0,02 | 99.8 |
| 0,2 | 88.8 |
| 2 | 70.2 |
| 20 | 35.3 |

| [μM] | % net growth |
|---|---|
| 0,02 | 99.7 |
| 0,2 | 99.9 |
| 2 | 98.7 |
| 20 | 96.0 |

(R) - 30

| [μM] | % net growth |
|---|---|
| 0,02 | 98.6 |
| 0,2 | 97.9 |
| 2 | 98.3 |
| 20 | 79.1 |

(S) - 30

| [M] | % net growth |
|---|---|
| 0,02 | 98.4 |
| 0,2 | 99.9 |
| 2 | 99.5 |
| 20 | 83.4 |

| [μM] | % net growth |
|---|---|
| 0,02 | 99.5 |
| 0,2 | 99.5 |
| 2 | 98.8 |
| 20 | 75.3 |

Fig. 14
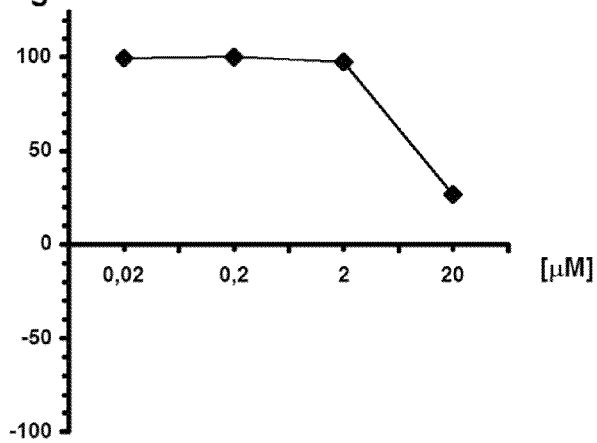
| [μM] | % net growth |
|---|---|
| 0,02 | 99.2 |
| 0,2 | 99.9 |
| 2 | 97.4 |
| 20 | 26.9 |
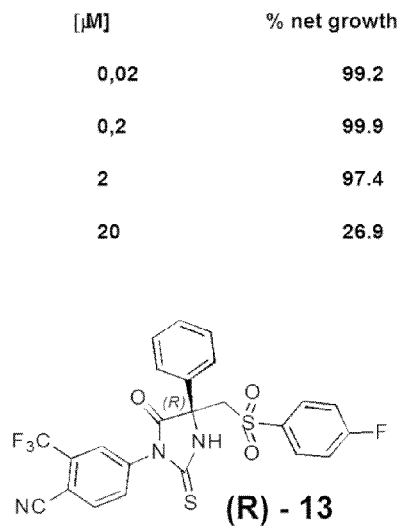
(R) - 13
Fig. 15
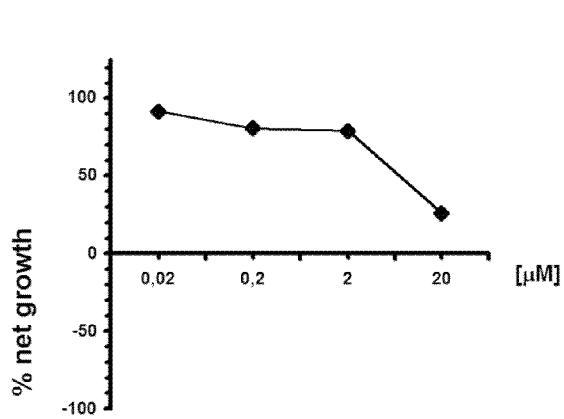
| [M] | % net growth |
|---|---|
| 0,02 | 91.4 |
| 0,2 | 80.7 |
| 2 | 78.8 |
| 20 | 25.8 |
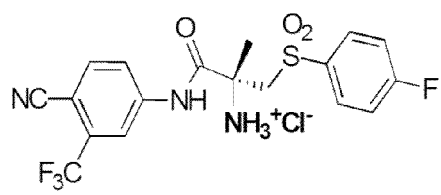
(S) - 24

| [μM] | % net growth |
|---|---|
| 0,02 | 99.5 |
| 0,2 | 96.2 |
| 2 | 96.9 |
| 20 | 68.7 |

| [μM] | % net growth |
|---|---|
| 0,02 | 98.9 |
| 0,2 | 90.5 |
| 2 | 57.4 |
| 20 | 2.8 |

Fig.18
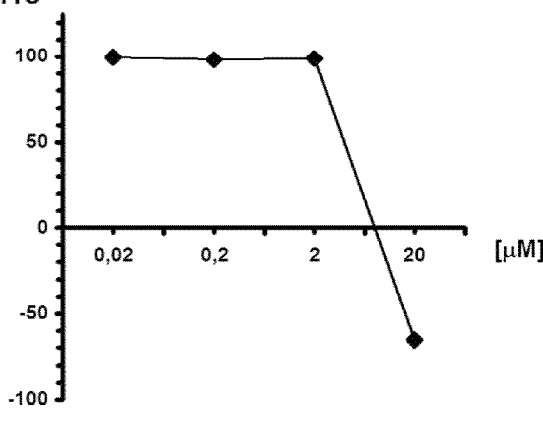
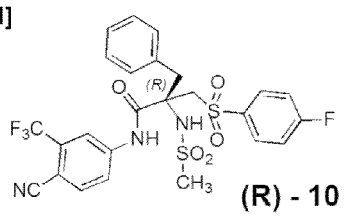
| [M] | % net growth |
|---|---|
| 0,02 | 99.7 |
| 0,2 | 98.3 |
| 2 | 98.9 |
| 20 | -65.4 |
(R) - 10
Fig. 19
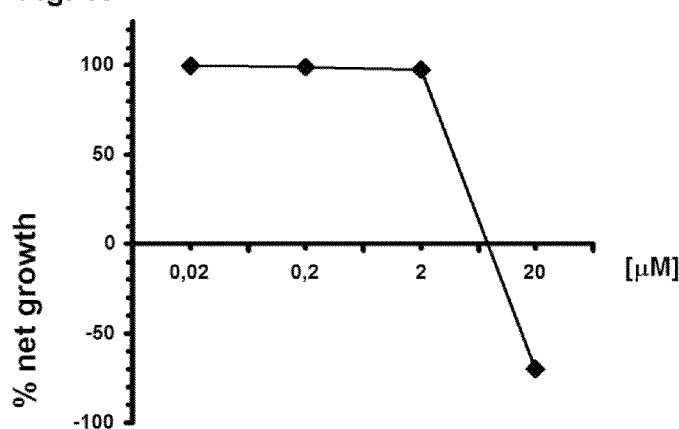
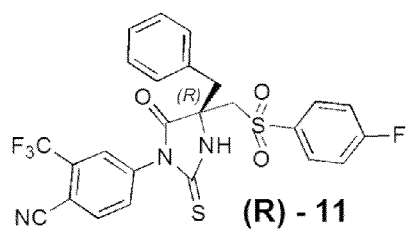
| [µM] | % net growth |
|---|---|
| 0,02 | 99.8 |
| 0,2 | 98.9 |
| 2 | 97.8 |
| 20 | -69.8 |
(R) - 11

| [M] | % net growth |
|-----|--------------|
| 0,02 | 91.1 |
| 0,2 | 99.5 |
| 2 | 84.5 |
| 20 | -70.2 |

| [M] | % net growth |
|-----|--------------|
| 0,02 | 99.8 |
| 0,2 | 99.8 |
| 2 | 89.4 |
| 20 | 5.5 |

| [μM] | % net growth |
|---|---|
| 0,02 | 83.4 |
| 0,2 | 84.9 |
| 2 | 85.6 |
| 20 | -64.2 |

| [μM] | % Net Growth |
|---|---|
| 0,02 | 83,40268 |
| 0,2 | 85,1986 |
| 2 | 71,36999 |
| 20 | 22,61067 |

FIG. 30
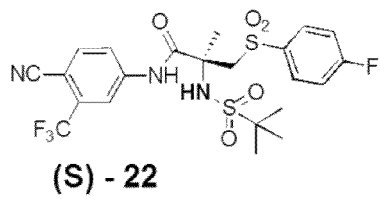
(S) - 22
PC-3
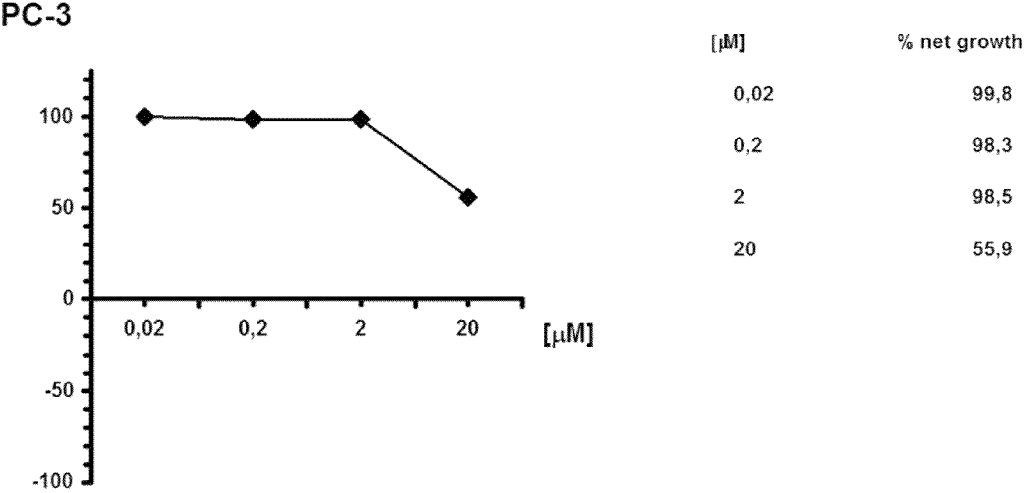
| [µM] | % net growth |
|---|---|
| 0,02 | 99,8 |
| 0,2 | 98,3 |
| 2 | 98,5 |
| 20 | 55,9 |
DU-145
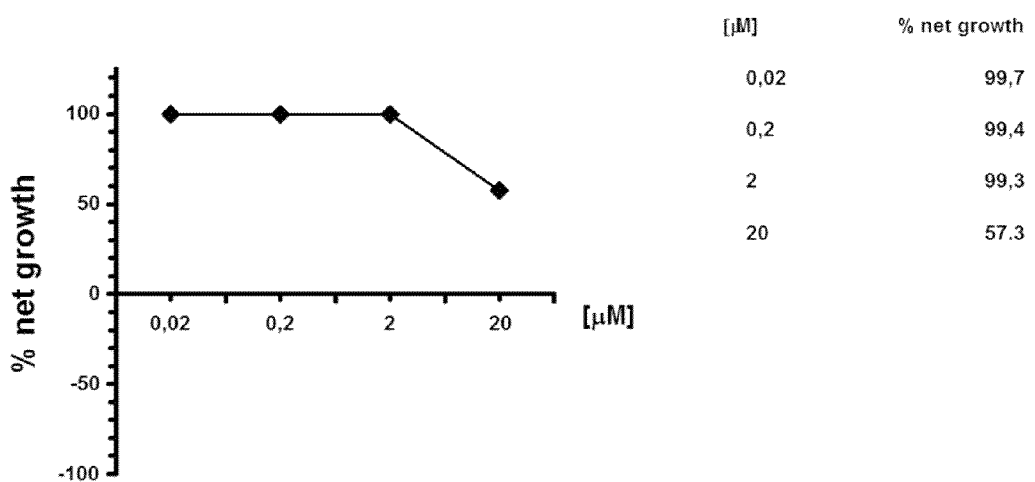
| [µM] | % net growth |
|---|---|
| 0,02 | 99,7 |
| 0,2 | 99,4 |
| 2 | 99,3 |
| 20 | 57.3 |

FIG. 31
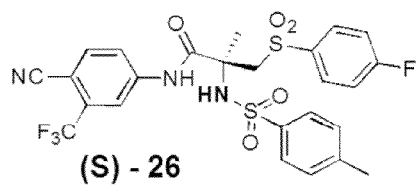
(S) - 26
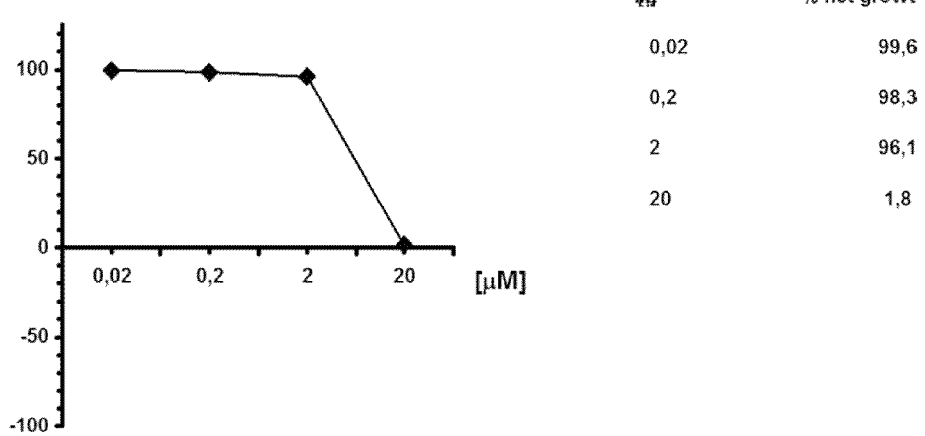
| [µM] | % net growt |
|---|---|
| 0,02 | 99,6 |
| 0,2 | 98,3 |
| 2 | 96,1 |
| 20 | 1,8 |
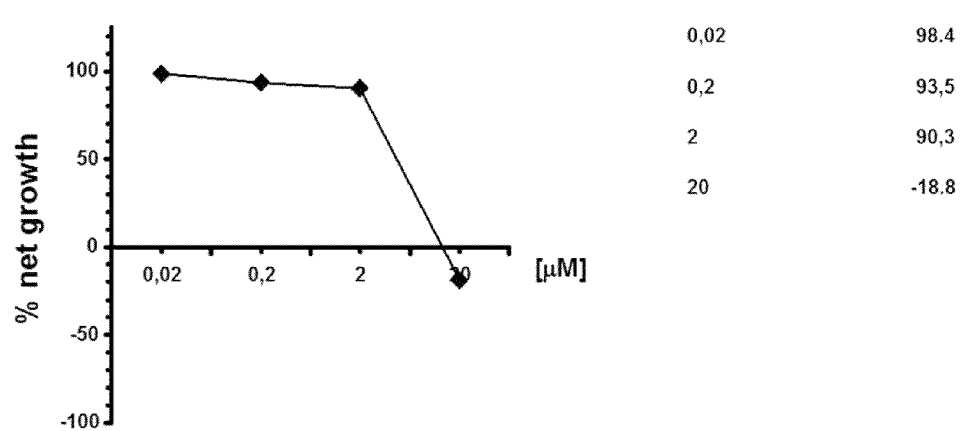
| [µM] | % net growth |
|---|---|
| 0,02 | 98.4 |
| 0,2 | 93,5 |
| 2 | 90,3 |
| 20 | -18.8 |

FIG. 32
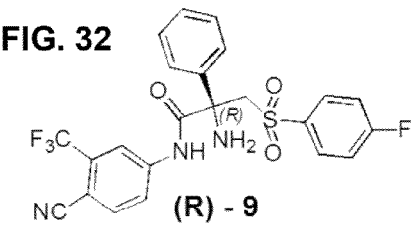
(R) - 9
PC-3
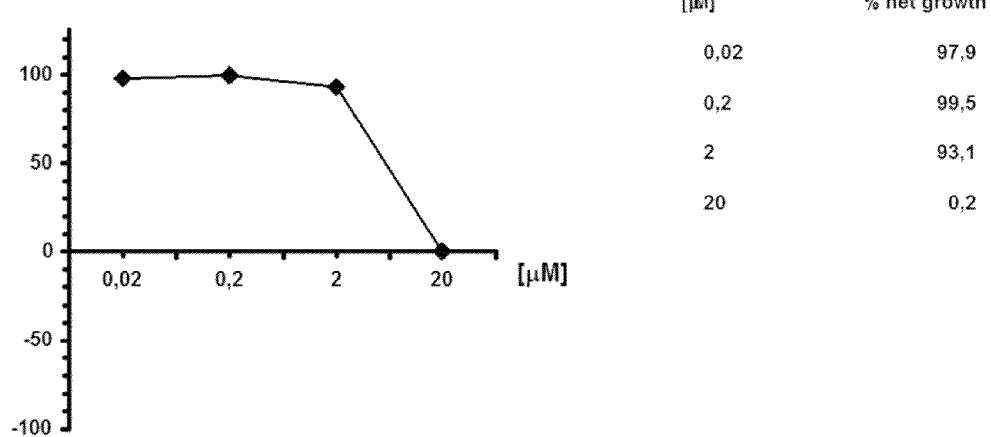
| [μM] | % net growth |
|---|---|
| 0,02 | 97,9 |
| 0,2 | 99,5 |
| 2 | 93,1 |
| 20 | 0,2 |
DU-145
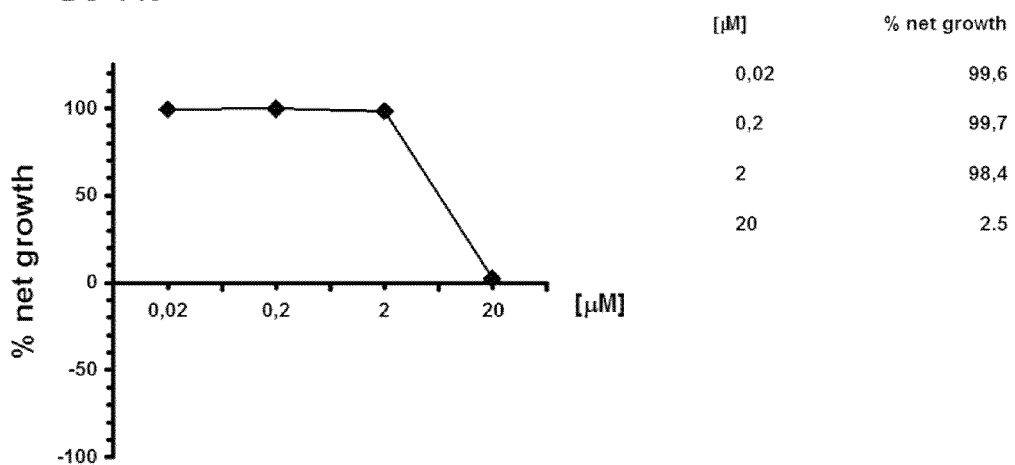
| [μM] | % net growth |
|---|---|
| 0,02 | 99,6 |
| 0,2 | 99,7 |
| 2 | 98,4 |
| 20 | 2.5 |

FIG. 33
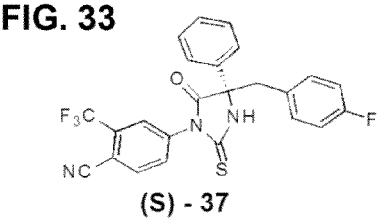
(S) - 37
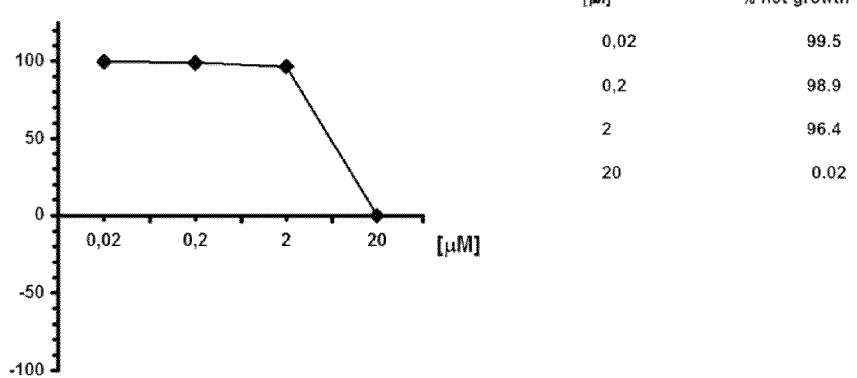
| [μM] | % net growth |
|------|--------------|
| 0,02 | 99.5 |
| 0,2  | 98.9 |
| 2    | 96.4 |
| 20   | 0.02 |
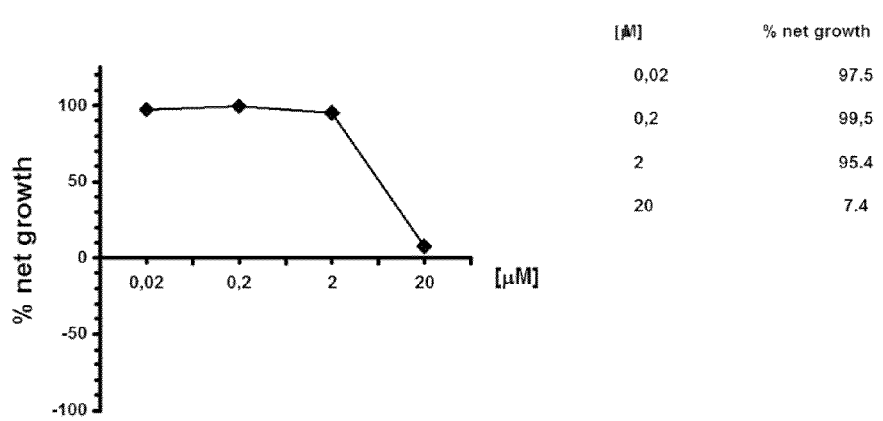
| [μM] | % net growth |
|------|--------------|
| 0,02 | 97.5 |
| 0,2  | 99,5 |
| 2    | 95.4 |
| 20   | 7.4 |

FIG. 34
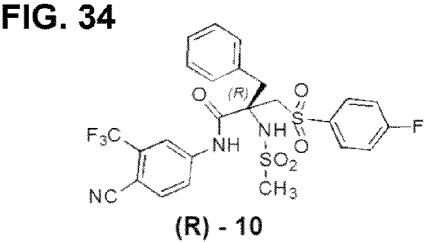
(R) - 10
PC-3
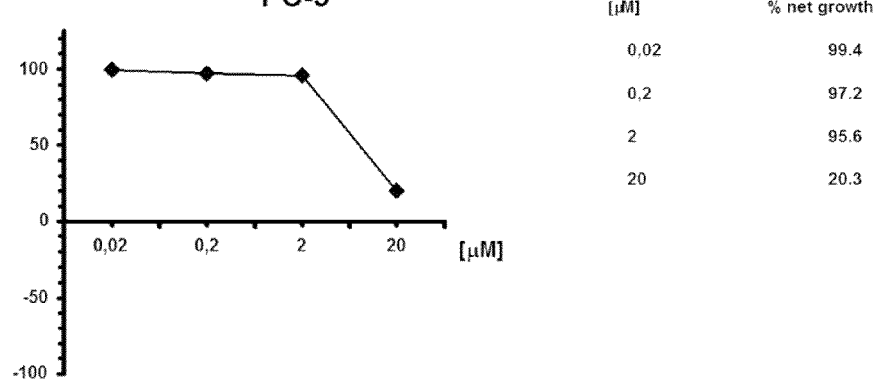
| [μM] | % net growth |
|---|---|
| 0,02 | 99.4 |
| 0,2 | 97.2 |
| 2 | 95.6 |
| 20 | 20.3 |
DU-145
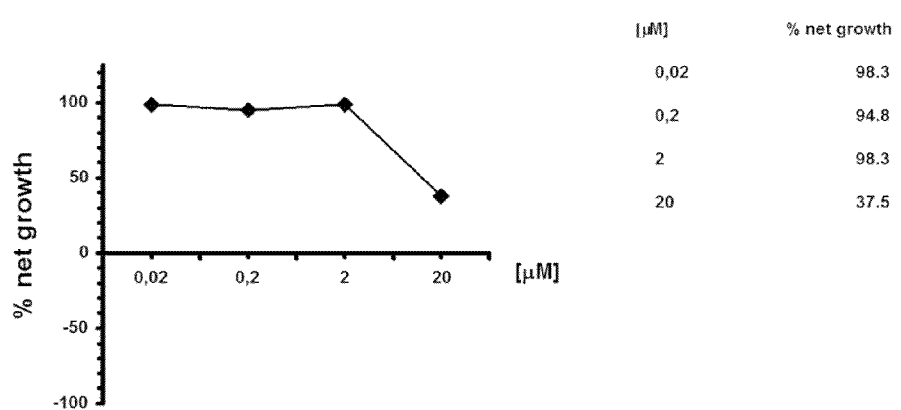
| [μM] | % net growth |
|---|---|
| 0,02 | 98.3 |
| 0,2 | 94.8 |
| 2 | 98.3 |
| 20 | 37.5 |

ANDROGEN RECEPTOR MODULATING COMPOUNDS, PREPARATION AND USES THEREOF

CROSS-REFERENCE TO RELATED APPLICATIONS

This application is a 371 of PCT/IB2010/050636 filed on Feb. 11, 2010, which claims the benefit of Italian Patent Application No. BO2009A000078 filed on Feb. 13, 2009, the contents of each of which are incorporated herein by reference.

FIELD OF THE INVENTION

The present invention provides nuclear hormone receptor binding compounds and pharmaceutically acceptable salts and esters thereof useful in the treatment of nuclear receptor, especially steroid receptor, and in particular androgen receptor (AR) dependent conditions. In particular, the invention discloses novel non-steroidal propionanilide and hydantoine structured compounds having utility as tissue-selective androgen receptor modulators (SARM). The compounds of the invention, which possess AR antagonist activity, are useful in prostate cancer therapy, especially in treatment of hormone-dependent cancer and in some hormone-refractory prostate cancers.

BACKGROUND OF THE INVENTION

Androgen receptor (AR), a member of the steroid receptor super-family, is a ligand-dependent transcription factor that mediates androgen action in cells. The AR is widely distributed among cardiac muscle, skeletal and smooth muscle, gastrointestinal vesicular thyroid follicular cells, adrenal cortex, liver, pineal, and numerous brain cortical and subcortical regions, including spinal motor neurons. AR is composed of three major domains: an $NH_2$-terminal transcriptional activation domain, a central DNA-binding domain, and a COOH-terminal ligand-binding domain. After binding to androgens, AR translocates to the nucleus and regulates expression of AR target reproductive and non-reproductive tissues, including the prostate and seminal vesicles, male and female external genitalia, skin, testis, ovary, cartilage, sebaceous glands, hair follicles, sweat glands, genes. [Gelmann E. P. *J Clin Oncol* 2002, 20, 3001-15; Heinlein, C. A.; Chang, C. *Endocr Rev* 2004, 25, 276-308] AR hypersensitivity, as a result of AR gene mutation and/or amplification, overexpression of coactivators, often occurs and plays crucial roles in prostate cancer development, progression, and androgen-independent growth. [Heinlein, C. A.; Chang, C. *Endocr Rev* 2004, 25, 276-308; Chen, C. D et al., *Nat Med.,* 2004; 10, 33-9; Isaacs, J. T.; Isaacs, W. B. Nat. Med. 2004; 10, 26-7] Therefore, in most cases advanced prostate cancer, one of the leading cause of cancer death in men after lung cancer, it has been directly linked to the androgen receptor (AR). Most prostatic tumors are stimulated to grow by androgens, and consequently androgen withdrawal is a well-established therapy for prostate cancer treatment. Androgen deprivation therapies consist of surgical castration, through orchiectomy or medical castration by administration of a luteinising hormone-releasing hormone analogue (LHRH-A), such as goserelin [Kirby, R. S. *Crit J Clin Pract* 1996; 50, 88-93](Zoladex™, AstraZenaca). However, although castration removes androgen release from the testes, androgen biosynthesis in the adrenals (8±10% of total circulating androgens) is not affected. [Geller J. *The role of adrenal androgens in prostate cancer* in: Pasqualini J. R., Katzenellenbogen, B. S. (eds). *Hormone-Dependent Cancer.* Marcel Dekker: New York, 1996, 289-305] Because of this, a widely used management strategy for advanced prostate cancer is a combination of surgical or chemical castration and administration of antiandrogens. [Labrie, F.; et al., *Clin Invest Med* 1982; 5, 267-275] Antiandrogens bind to the AR and inhibit all androgens at the target cell level. In particular, antiandrogens compete with endogenous androgens for binding sites of the androgen receptors in the prostate cell nucleus, thereby promoting apoptosis and inhibiting prostate cancer growth. By contrast with androgens, however, the receptor-antiandrogen complex is unstable so that gene transcription and protein synthesis are not stimulated. [Gaillard-Moguilewsky, M. *Urology* 1991, 37 (Suppl), 5-12]

Ideally, an antiandrogen should possess high specificity and affinity for the androgen receptor, being devoid of other hormonal or anti-hormonal activity. Antiandrogens act by two primary mechanisms: inhibition of ligand (androgen) binding to the AR, and inhibition of androgen-independent activation of the receptor. It is more accurate to refer to these compounds as androgen-receptor antagonists, since they inhibit activation, whether this is androgen-mediated or not. There are two structurally distinct types of antiandrogen, i.e. steroidal and non-steroidal. One steroidal and three non-steroidal antiandrogens are in common use for the treatment of prostate cancer. However, the use of the steroidal agent cyproterone acetate (CPA), a synthetic derivative of hydroxyprogesterone, is limited since, in addition to blocking androgen receptors, has progestational and antigonadotrophic properties. [Furr, B. J. A.; Kaisary, A. V. Treatment: hormonal manipulation: Antiandrogens. In Kaisary, A. V.; et al., eds. *Textbook of Prostate Cancer: Pathology, Diagnosis and Treatment*. London: Martin Dunitz, 1999: 277-90]

CPA therefore inhibits the release of LH, decreasing serum testosterone levels, and causing a severe suppression of libido and loss of erectile potency. The nonsteroidal antiandrogens, bicalutamide, flutamide and nilutamide are pure antiandrogens, which exert their effects through competitive inhibition of the binding of testosterone, and its metabolite 5-α dihydrotestosterone (5α-DHT), to the nuclear androgen receptor. As testosterone levels are not blocked by nonsteroidal antiandrogens, [Gaillard-Moguilewsky, M. *Urology* 1991, 37 (Suppl), 5-12] these drugs offer the possibility of maintaining sexual interest and potency. Within the class of non-steroidal anti-androgens, there is variation in the degree to which ligand-independent activation is inhibited. Preclinical data suggest that non-steroidal antiandrogen bicalutamide may be a more effective drug in the treatment of prostate cancer with respect to flutamide and nilutamide. [Tucker, H.; et al., *J. Med. Chem.,* 1988, 31, 954-959]

The endocrine therapy using non-steroidal antiandrogens and LHRH analogs is initially very effective but is time-limited. Nearly half of all patients with these tumors develop resistance to this therapy after several years, suggesting the development of androgen-independent prostate cancer cells or the ability of adrenal androgens to support tumor growth. This leads to serious clinical inconveniences. [Oh, W. K.; Kantoff, P. W. *J Urol* 1998, 160, 1220-1229]

Surprisingly, clinical benefit has been observed following the withdrawal of anti-androgens (*Anti-Androgen Withdrawal Response*, AAWR) in a subset of prostate cancer patients with therapy-resistant disease. [Scher, H. I.; Kolvenbag, G. J. *Eur Urol.,* 1997, 31, 3-7] The anti-androgen withdrawal event indicate that there may be clinically relevant changes in AR expression and function during long-term androgen ablation which can be in part attributed to mutant ARs detected in prostatic carcinomas. For example, bicalutamide that acts as a pure antagonist in parental LNCaP cells, showed agonistic effects on AR transactivation activity in LNCaP-abl cells and was not able to block the effects of androgen in these cells. [Culig, Z. et al., *British J. of Cancer* 1999, 81, 242-251] However, alternative mechanisms may also be considered. In fact, it has been found that non-steroidal antiandrogens act as AF-1 agonists under conditions of high AR protein expression. This partial antagonistic property of antiandrogens may be a molecular mechanism by which prostate cancer develops resistance to these drugs. [Fuse, H et al., *The Prostate,* 2007, 67, 630-637] These findings may have repercussions on the natural course of prostate cancer with androgen deprivation and on strategies of therapeutic intervention. For this reason, secondary treatment to block androgen receptors in a primary, secondary or tertiary manner has been developed. Secondary hormonal manipulations for affected patients include antiandrogen withdrawal, second-line antiandrogens, [Kojima, S. et al., *J Urol.* 2004, 171, 679-683] direct adrenal androgen inhibitors (aminoglutethimide, ketoconazole), [Mahler, C.; Verhelst, J.; Denis, *Cancer,* 1993, 71, 1068; Sartor, O et al., *J. Natl. Cancer Inst.* 1944, 86, 222] corticosteroids (e.g.: mitoxantone), [Tannock, I. F et al., *J. Clin. Oncol.* 1996, 14, 1756] estrogens [Ferro, M. A. et al., *Urology* 1989, 34: 134] and progestins. More recently, new classes of antiandrogens have been investigated. These compounds have not yet clinically been evaluated, but demonstrate potent antiandrogenic activity in in vitro and preclinical models. Selected examples are: a) Bicyclic-$^1$H-isoindole-1,3-(2H)-dione analogues which can be considered as tructurally modified of nilutamide analogues. [Salvati, M. E. et al., *Bioorg. Med. Chem. Lett.* 2005, 15, 389] b) quinolone derivatives with a linear tricyclic pharmacophore, 2(1H)-piperidino[3,2-g]quinolinone. [Hamann, L. G. et al., *J. Med. Chem.* 1998, 41, 623] c) androgen receptor antagonists containing a carborane moiety as a hydrophobic skeletal structure. These compounds bind to AR and show antiandrogenic activity towards androgen-dependent SC-3 cells with almost the same potency as the known anti-androgen hydroxyflutamide. [Fujii, S. et al., *Bioorg. Med. Chem. Lett.* 2005, 15, 227-230] d) β-Alkylthio indolyl carbinols [Lanter, J. C.; et al., *Bioorg. Med. Chem. Lett.* 2007, 17, 2545-2548] e) Phenotiazine derivatives. [Bisson, W. H. et al. *PNAS,* 2007, 104, 11927-11932] Although these nonsteroidal antiandrogens exhibit high specificity for AR and are orally available, they do not possess tissue selectivity. Along with the blockade of AR action in the prostate, antiandrogens also block AR actions in other target tissues, including anabolic tissues (e.g., skeletal muscle and bone) and the hypothalamus-pituitary-testis axis.

In the past several years, a new class of non-steroid molecules targeting the androgen receptors has emerged. [Zhi, L.; Martinborough, E. *Annu. Rep. Med. Chem.* 2001, 36, 169; Negro-Vilar, A. *J. Clin. Endocrinol. Metab.* 1999, 84, 3459] For these molecules the term of selective androgen receptor modulators (SARMs) has been chosen after the discovery of similar molecules, the selective estrogen receptor modulators (SERMs), which targets the estrogen receptors. SARMs selectively bind and modulate ARs depending on tissue type. The goal of research in this area is to allow a customized response, namely, tissues that are the target of the therapy will respond as they would to testosterone; other tissues, where undesirable side effects are produced, will not. For an ideal selective androgen receptor modulator, the antagonist or weak agonist activity in the prostate will not stimulate nascent or undetected prostate cancer; while the strong agonist activity can be, exploited to stimulate testosterone's beneficial action in bone, muscle and brain, either cross or not cross into the central nervous system to affect lipids. Because of these properties, SARMs could be developed to treat a range of medical conditions and physiological functions. Potential indications are: andropause conditions of aging [Tenover, J. L. *J Androl* 1997, 18, 103-106] (hypogonadism, sarcopenia, osteoporosis, high cholesterol); disorders of the nervous central system (low libido, depression and mood); male reproduction [Wu, F. C. *Baillieres Clin. Endocrinol. Metab.* 1992, 6, 373-403] (infertility, male contraception, erectile dysfunction); wasting conditions associated with disease and trauma (cancer, AIDS); end stage of renal disease; severe burns; prostate disorders (BPH, prostate cancer) and other conditions (anaemia, obesity, high cholesterol, hair loss). Structural modifications of bicalutamide led to the discovery of selective androgen receptor modulators. Lead compounds (S)-3-(4-acetylphenoxy)-2-hydroxy-2-methyl-N-[4-nitro-3-(trifluoromethyl)phenyl]-propanamide and (S)-2-hydroxy-2-methyl-N-[4-nitro-3-(trifluoromethyl)phenyl]-3-(4-propionylphenoxy)propanamide, which not only bind AR with high affinity, but also demonstrate tissue selectivity in animal models. [Yin, D. et al., *J. Pharmacol. Exp. Ther.* 2003, 304, 1334-1340; Gao, W. et al., *Endocrinology* 2004, 145, 5420-5428]

Quite interestingly, in intact male rats, (S)-3-(4-acetylphenoxy)-2-hydroxy-2-methyl-N-[4-nitro-3-(trifluoromethyl)phenyl]-propanamide and (S)-2-hydroxy-2-methyl-N-[4-nitro-3-(trifluoromethyl)-phenyl]-3-(4-propionylphenoxy)propanamide behaved as antagonists in the prostate without reducing the anabolic effects of androgens, thus suggesting that selective androgen receptor modulators with low intrinsic activity in the prostate, might serve as an alternative therapy for benign prostate hyperplasia (BPH) or even prostate cancer. For this reason, the AR binding ability and in vitro functional activity and the structure-activity relationships (SARs) of a series of non-steroidal compounds derived from bicalutamide was examined. [He, Y. et al., *Eur. J. Med. Chem.* 2002, 37, 619-634; Yin, D. et al., *Mol. Pharmacol.* 2003, 63, 211-223] These studies demonstrated that non-steroidal ligands can be structurally modified from known non-steroidal antiandrogens to generate ligands capable of activating AR-mediated transcriptional activation. The conclusion was that the overall effect on AR binding affinities, as well as, their abilities to stimulate AR-mediated transcriptional activation is determined, by a delicate balance of factors, including nature, size, and position of the substituent.

There is a need for new compounds having desirable pharmacological properties, and synthetic pathways for preparing them. Because activities are very sensitive to small structural changes, one compound may be effective in treating prostate cancer, whereas a second compound may be effective in treating other AR related pathologies, such as: male contraception, treatment of a variety of hormone-related conditions, for example conditions associated with Androgen Decline an Aging Male (ADAM), such as fatigue, depression, decreased libido, sexual dysfunction, hypogonodism, osteoporosis, hair loss, anemia, erectile dysfunctions, obesity, sarcopenia, osteopenia, benign prostate hyperplasia, alterations in mood and cognition; treatment of conditions associated with AIDF, such as sexual dysfunction, decreased sexual libido, depression, anemia, hair loss, obesity, endometriosis, breast cancer, uterine cancer and ovarian cancer; treatment and/or prevention of chronic muscular wasting.

Therefore, the aim of the present invention is to provide compounds, their synthesis and their pharmaceutically acceptable preparations, which are useful in the treatment of the above mentioned pathologies.

SUMMARY OF THE INVENTION

The present invention provides compounds, pharmaceutical preparations, uses and procedures for their synthesis, which can be easily and inexpensively prepared and are able to fully or partially overcome the inconveniences of the compounds of the state of the art.

According to a first aspect of the present invention, a compound of general formula (I) is provided:

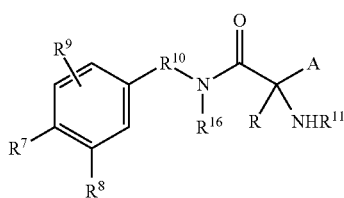

(I)

wherein
R is: H, i), ii), iii), iv), v) or vi) as defined below:
i) aryl, optionally substituted aryl, The term "aryl" means an aromatic carbocyclic ring system having a single radical containing 6 or more carbon atoms. An aryl group may be a fused or polycyclic ring system. Exemplary aryl groups include phenyl and napthyl. The term "substituted aryl" refers to an aryl group substituted with one, two or three substituents independently selected from halo, hydroxy, protected hydroxy, cyano, nitro, alkyl, alkoxy, carboxy, protected carboxy, carbamoylmethyl, hydroxymethyl, amino, aminomethyl, trifluoromethyl, N-methylsulfonylamino, and the like. Optionally "substituted" is intended to include both substituted and unsubstituted. Thus, for example, optionally substituted aryl could represent a pentafluorophenyl or a phenyl ring;

ii) heteroaryl, optionally substituted heteroaryl;
as used herein, the term "heteroaryl" means aromatic monocyclic or fused or polycyclic ring system having at least five ring atoms in which one or more of the atoms in the ring system is other than carbon, for example, nitrogen (including N-oxide), oxygen or sulfur. In a bicyclic aromatic radical only one ring, containing a heteroatom, need to be aromatic. Examples of heteroaryl include pyridyl, pyrrolyl, pyrazolyl, imidazolyl, thienyl, furanyl, indolyl, indolizinyl, azaindolizinyl, quinolyl, pyrazinyl, pyrimidinyl, pyridazinyl, oxazolyl, isoxazolyl, benzoxazolyl, benzisoxazolyl, benzothiazolyl, isoquinolinyl, benzimidazolyl, benztriazolyl, benzofuranyl, benzothienyl, benzopyranyl, imidazo[2,1-b]thiazolyl, imidazo[1,2-a]pyridyl, imidazo[1,2-a]-pyrimidinyl, pyrazolo[1,5-a]pyridyl, imidazolyl, triazolyl, thiadiazolyl, oxadiazolyl, thiazolyl, triazolopyrimidinyl, pyrazolopyrimidinyl, thienopyridinyl, pyrrolopyridinyl 4,5,6,7-tetrahydrobenzisoxazolyl, indazolyl, 4,5,6,7-tetrahydroindazolyl, and 4,5,6,7-tetrahydrobenzothienyl. The term "substituted heteroaryl" refers to a heteroaryl group substituted with one, two or three substituents independently selected from halo, hydroxy, protected hydroxy, cyano, nitro, alkyl, alkoxy, carboxy, protected carboxy, carbamoylmethyl, hydroxymethyl, amino, aminomethyl, trifluoromethyl, N-methylsulfonylamino, and the like;

iii) Straight or branched $C_{1-10}$ alkyl, wherein the alkyl may be substituted with one or more substituents which may be the same or different, and include halo, cycloalkyl containing three to six carbon atoms, hydroxy, alkoxy, amino, acylamino, aroylamino, carboxy, alkoxycarbonyl, aralkyloxycarbonyl;

iv) $C_1$-$C_4$-arylalkyl as defined herein. Suitable arylkyl groups include benzyl, phenethyl, alpha-methylbenzyl, picolyl, and the like, and may be optionally substituted. "Optionally substituted" is intended to include both substituted and unsubstituted. Thus, for example, optionally substituted aryl could represent a pentafluorophenyl or a phenyl ring; or v) $C_{1-4}$ heteroarylalkyl. The term heteroarylalkyl refers to a $C_{1-4}$ alkyl group substituted with an optionally substituted heteroarylalkyl group, wherein the terms alkyl and heteroaryl are described below;

vi) Substituted heterocyclylalkyl. The term heterocyclylalkyl refers to an alkyl group substituted with an optionally substituted heterocyclylalkyl group, wherein the term "Heterocyclyl" means a monocyclic or bicyclic radical that is fully saturated or partially saturated, containing 3 to 10 ring atoms at least one of which is selected from N—$R^g$ (including N-oxides), O, S and S(O)$_2$, wherein $R^g$ is selected from (1) H, (2) $C_{1-4}$alkyl, (3) aryl, (4) aryl-$C_{1-6}$alkyl, (5) C(O)$_2$C1-4alkyl, (6) C(O)$C_{1-4}$alkyl. Examples of heterocyclyl include aziridinyl, azetidinyl, pyrrolidinyl, piperidinyl, piperazinyl, morpholinyl, thiamorpholinyl, oxetanyl, tetrahydrofuranyl, tetrahydropyranyl, azepinyl, diazepinyl, dihydrobenzofuranyl, 1,2,3,4-tetrahydroquinolinyl, dioxanyl, dioxolanyl, imidazolinyl, imidazolidinyl, oxazolidinyl, 7-oxabicyclo[2.2.1]heptanyl, and the like;

$R^9$ is H, F, Cl, I or Br;

$R^7$ is H, CN, NO$_2$, F, Cl, I, Br, carbamoyl, or alkyl, alkoxy, alkanoyl, alkylthio, alkylsulphinyl, alkylsulphonyl, perfluoroalkyl, perfluoroalkylthio, perfluoroalkylsulphinyl or perfluoroalkysulphonyl each being substituted or unsubstituted and having up to 4 carbon atoms, or phenyl, phenylthio, phenylsulphinyl or phenylsulphonyl; each being substituted or unsubstituted;

$R^8$ is cyano, carbamoyl, nitro, fluoro, chloro, bromo, iodo or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each being substituted or unsubstituted and having up to 4 carbon atoms, or phenyl, phenylthio, phenylsulphinyl or phenylsulphonyl, each being substituted or unsubstituted;

$R^{10}$ is $C_1$-$C_4$alkyl or a bond;

$R^{16}$ is H, $C_1$-$C_4$-alkyl, —CO—, —CS—, —SO—, —SO$_2$—, —$R^p$CS—, —$R^p$CO—, —$R^p$SO—, —$R^p$SO$_2$— wherein $R^p$ is a $C_1$-$C_4$ alkyl and with, the condition that when $R^{16}$ is —CO— or —CS—, it is connected to NHR$^{11}$ to form a cycle; $C_1$-$C_4$-alkyl, —SO—, —SO$_2$—, —$R^p$CS—, —$R^p$CO—, —$R^p$SO—, —$R^p$SO$_2$— can also be connected to NHR$^{11}$ to form a cycle;

$R^{11}$ is H, $C_1$-$C_6$ alkyl, substituted $C_1$-$C_6$ alkyl, $C_1$-$C_6$ hetero alkyl, substituted $C_1$-$C_6$ hetero alkyl, aryl, substituted aryl, $C_1$-$C_4$-alkylaryl, hetero aromatic $C_1$-$C_4$ alkyl, aromatic hetero cycle, substituted aromatic hetero cycle, a protecting group or a chiral auxiliar. The protecting group is selected among the group of —COR$^r$, —COOR$^r$, —OSO$_2$R$^r$, —SO$_2$R$^r$, —SR$^r$. The chiral auxiliar is selected among the group of —OS(O)R$^r$, —OP(O)R$^s$R$^r$ where R$^r$ and R$^s$ can be the same or different; R$^r$ and R$^s$ are selected among: $C_1$-$C_6$ alkyl, $C_1$-$C_6$ halo-alkyl, aryl, substituted aryl, aromatic hetero cycle, substituted aromatic hetero cycle.

A is a group selected from aryl, as defined above, $C_{1-4}$ arylalkyl as defined above, or A is formula II:

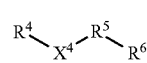

(II)

wherein
R⁴ is substituted or unsubstituted alkyl (alkylene) having up to 6 carbon atoms and is attached to the rest of the molecule. Most preferably, R⁴ is methyl (methylene);
X⁴ is oxygen, sulfur, sulfinyl (—SO—), sulfonyl (—SO₂—) imino (—NH—) or alkylimino (—NR″—) wherein R″ is H, $C_1$-$C_4$ alkyl;
R⁵ is a direct bond or a substituted or unsubstituted alkylene having up to 6 carbon atoms. Preferably, R⁶ is a direct bond or an unsubstituted alkylene having 1, 2 or 3 carbon atoms;
R⁶ is alkyl, alkenyl, hydroxyalkyl, or cycloalkyl each being substituted or unsubstituted and having up to 6 carbons (e.g. methyl, ethyl, n-propyl, isopropyl, n-butyl, allyl, 2-methlyprop-2-enyl, 2-hydroxyethyl, cyclopentyl or cyclohexyl); or R⁶ is phenyl which bears one, two or three substituents independently selected from hydrogen, halogen, nitro, carboxy, carbamoyl and cyano, alkyl, alkoxy, alknoyl, alkylthio, alkylsulfinyl, alkylsulfonyl, perfluoroalkyl, perfluoroalkoxy, perfluoroalkylthio, perfluoroalkylsulfinyl, perfluoroalkylsulfonil, alkoxycarbonyl and N-alkylcarbamoyl each up to 4 carbon atoms and phenyl, phenylthio, phenylsulfynil and phenylsulfonyl, or R⁶ is naphthyl, or R⁶ is a 5- or 6-membered saturated or unsaturated heterocyclic which contains one, two or three heteroatoms selected form oxygen, nitrogen and sulfur, which heterocyclic may be single ring or may be fused to a benzo-ring, and which heterocyclic is unsubstituted or bears one or two halogen, cyano or amino, or alkyl, alkoxy, alkylsulfinyl or alkylsulfonyl each of up to 4 carbon atoms, or oxy or hydroxy substituents, or which is sufficiently saturated may bear one or two oxo substituents (e.g. furyl, thinly, pyrrolyl, pyridyl, imidazolyl, thiazolyl, pyrimidinyl, thiadiazolyl, triazolyl, benzimidazolyl, benzothiazolyl, indolyl, bebzothienyl, quinolyl, isoquinolyl, benzofuryl, or 1,2-dihydro-2-oxoquinolyl), R⁶ is preferably phenyl which bears one, two or three substituents independently selected form hydrogen, halogen, cyano, nitro.

In another embodiment, compound of formula I, is represented by the following stereoisomer or diastereoisomer structure:

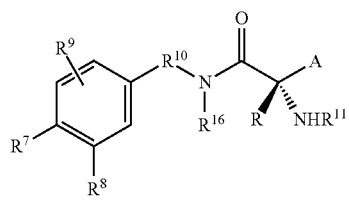

In another embodiment, compound of formula I, is represented by the following stereoisomer or diastereoisomer structure:

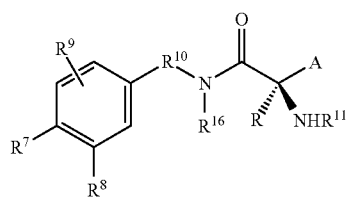

In one embodiment, the compound is represented by, the structure of formula III, IV or V:

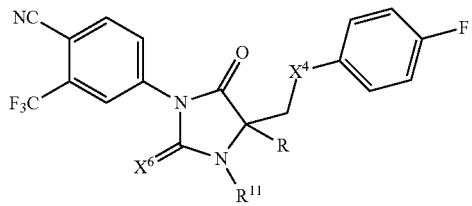

III or

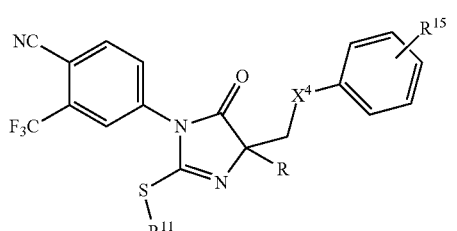

IV or

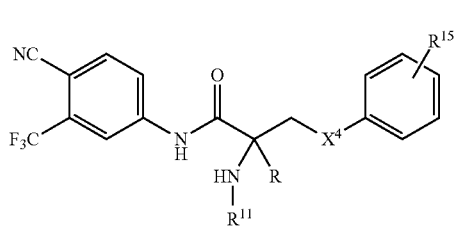

V

Wherein
X⁴ is oxygen, sulfur, sulfinyl (—SO—), sulfonyl (—SO₂—) imino (—NH—) or alkylimino (—NR″—). R″ is H, $C_1$-$C_4$ alkyl;
R, R¹¹ and R¹⁵ are as described above;
X⁶ is O or S;

In another embodiment, the compound has the formula selected from the group:

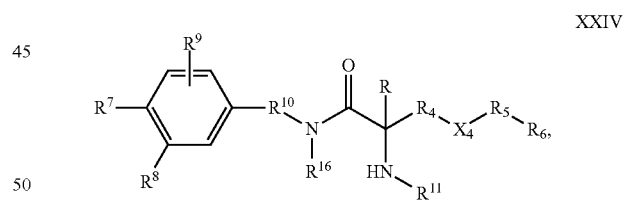

XXIV

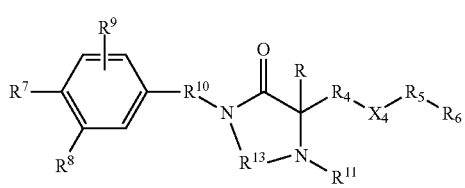

(XVI)

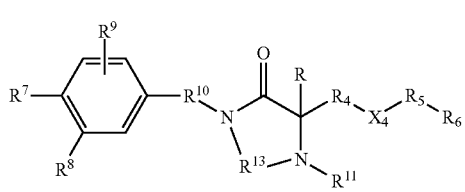

(XVI)

-continued

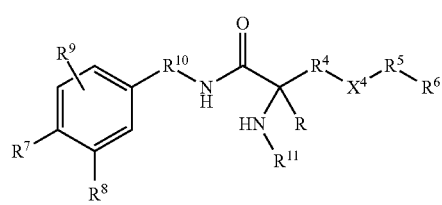
(XIV)

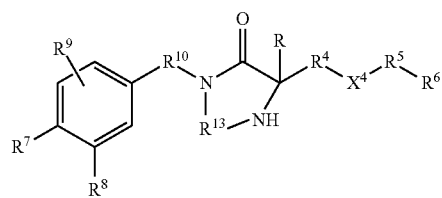
(XV)

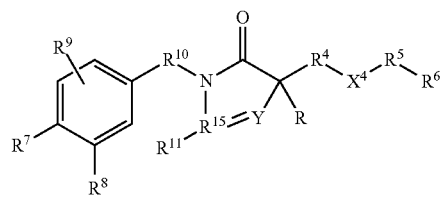
(XVII)

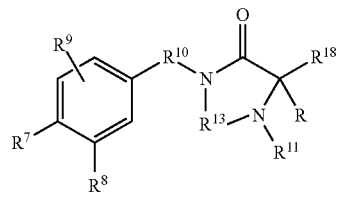
(XXI)

wherein R¹³ is $C_1$-$C_4$-alkyl, —CO—, —CS—, —SO—, —SO$_2$—, —R$^p$CO—, —R$^p$CS—, —R$^p$SO—, —R$^p$SO$_2$— in which R$^p$ is a $C_1$-$C_3$-alkyl;

R¹⁵ is —C═S—; R¹⁸ is aryl, $C_1$-$C_4$-alkyl, $C_1$-$C_4$-heteroalkyl, $C_1$-$C_4$-arylalkyl, $C_1$-$C_4$-heteroarylalkyl, substituted $C_1$-$C_4$-arylalkyl, substituted $C_1$-$C_4$-heteroarylalkyl or is A as defined above; the other substituents are defined above.

According to specific embodiments, compound (I) is selected among the following structures:

(R)-23

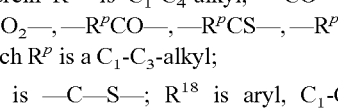
(S)-23

-continued

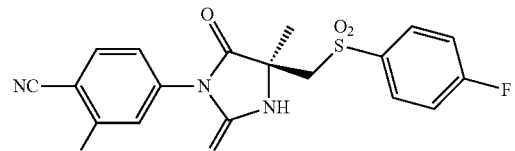
(S)-28

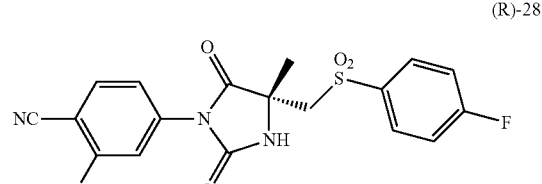
(R)-28

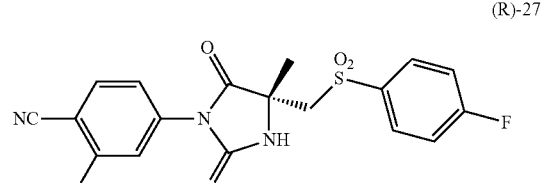
(R)-27

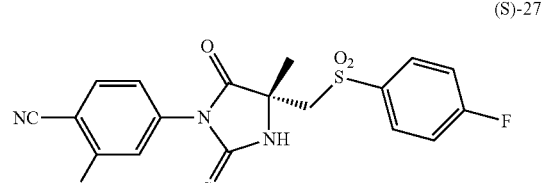
(S)-27

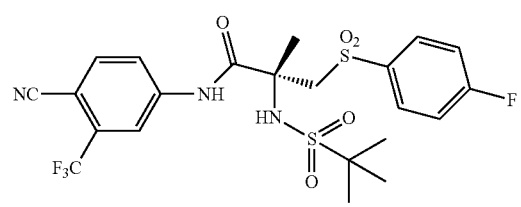
(R)-22

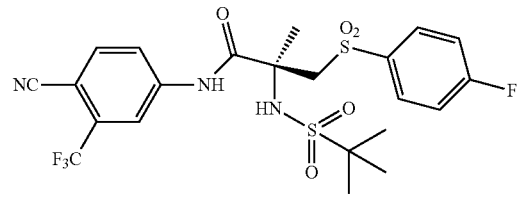
(S)-22

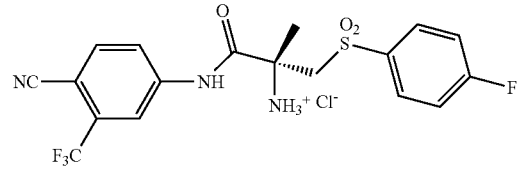
(R)-24

-continued (R)-26

(S)-26

(R)-29

(S)-29

(R)-30

(S)-30

(R)-8

-continued (S)-8

(R)-9

(S)-9

(R)-31

(S)-31

(S)-32

(R)-11
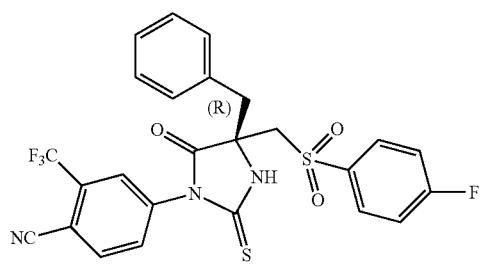

(S)-36
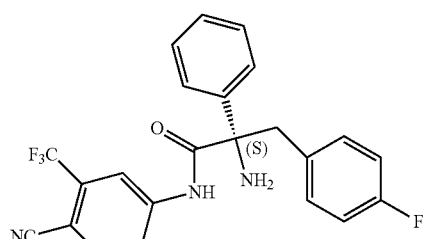

(S)-37
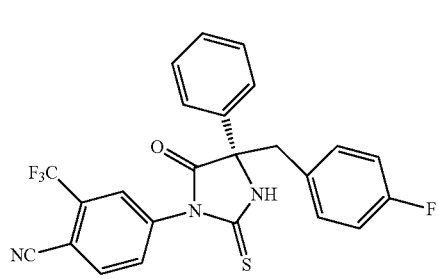

(R)-10
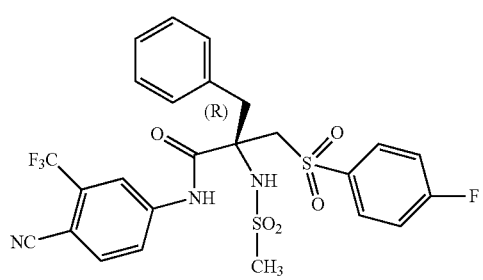

(R)-13
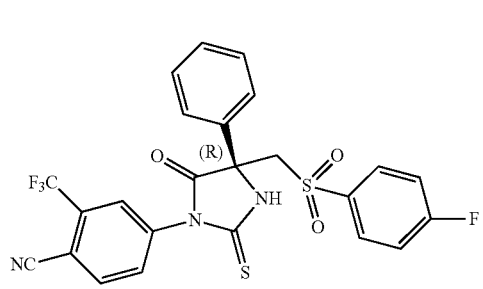

(S)-7d
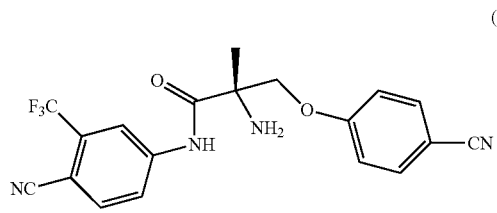

(S)-14d
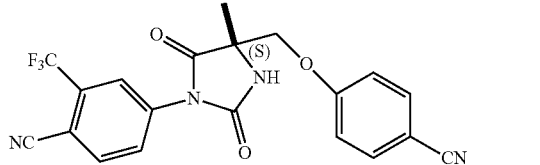

(S)-14e
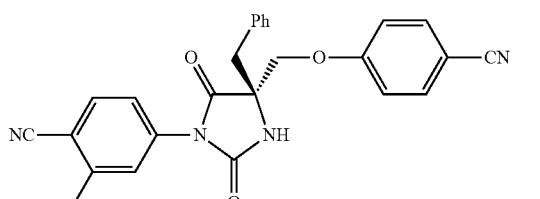

(S)-7c
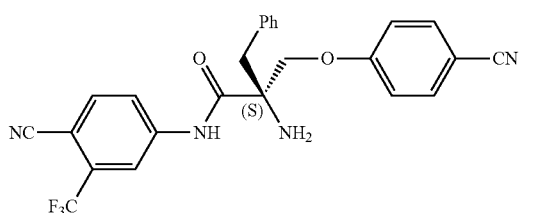

(R)-12
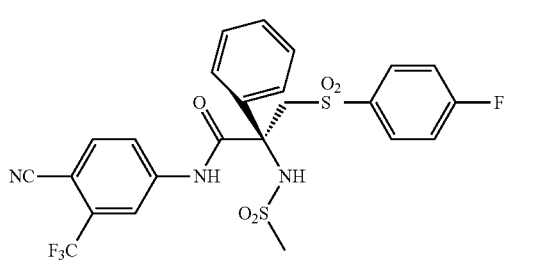

According to a second aspect of the present invention, two different processes for the preparation of compound of general formula (I), as defined above, are provided.

The first process (Scheme 1) comprises:
an addition step, during which a compound whose synthetic equivalent has general formula XXVI

(XXVI)

is reacted with an imine of general formula XXIII

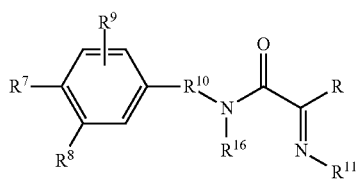
(XXIII)

wherein R, $R_4$, $R^5$, $R^6$, $R^7$, $R^8$, $R^9$, $R^{10}$, $R^{11}$, $R^{16}$, and $X^4$ are as defined above.

According to some aspect of the present invention, the compound, whose synthetic equivalent has general formula XXV, present the general formula XXIV

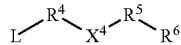

(XXV)

wherein L is selected among the group of metal, metal halide. In particular, L is selected among Li, MgX$^6$, wherein X$^6$ is halogen.

Furthermore, the process comprises a cyclization step, during which a compound of general formula XXIV

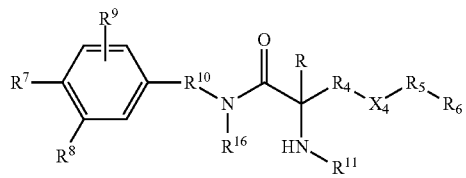

(XXIV)

wherein, if R$^{16}$ is H and R$^{11}$ is G, the compound has general formula XIII

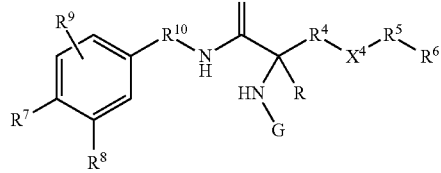

(XIII)

wherein G is H or a leaving group as defined below, is reacted with a cyclization compound, whose synthetic equivalent has general formula XXVI

(XXVI)

wherein R$^{13}$ is C$_1$-C$_4$-alkyl, —CO—, —CS—, —SO—, —SO$_2$—, —R$^p$CO—, —R$^p$CS—, —R$^p$SO—, —R$^p$SO$_2$— wherein R$^p$ is a C$_1$-C$_3$-alkyl;
in order to obtain a compound of general formula XVI

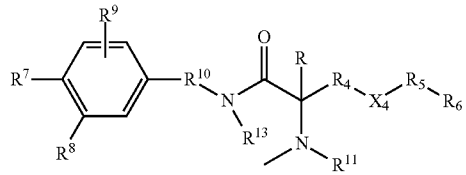

(XVI)

The second process (Scheme 2) exploit known literature procedures used for the synthesis of other compounds, except for the step which comprises the reaction of a compound of general formula IX

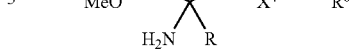

(IX)

or of general formula XIX

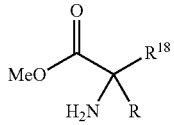

(XIX)

is coupled with a compound of general formula X

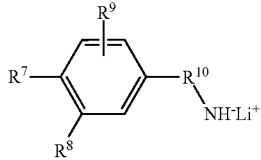

(X)

in order to provide a compound of general formula XIII

(XIII)

or of general formula XX

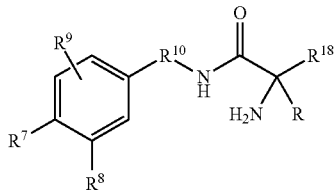

(XX)

wherein, wherein R, R$_4$, R$^5$, R$^6$, R$^7$, R$^8$, R$^9$, R$^{10}$ and X$^4$ are as defined above, R$^{18}$ is aryl, C$_1$-C$_4$-alkyl, C$_1$-C$_4$-heteroalkyl, C$_1$-C$_4$-arylalkyl, C$_1$-C$_4$-heteroarylalkyl, substituted C$_1$-C$_4$-arylalkyl, substituted C$_1$-C$_4$-heteroarylalkyl or is A as defined above.

According to specific embodiments, it is possible to prepare the compounds of general formula (I) following one of the synthetic procedures reported below:

Scheme 1
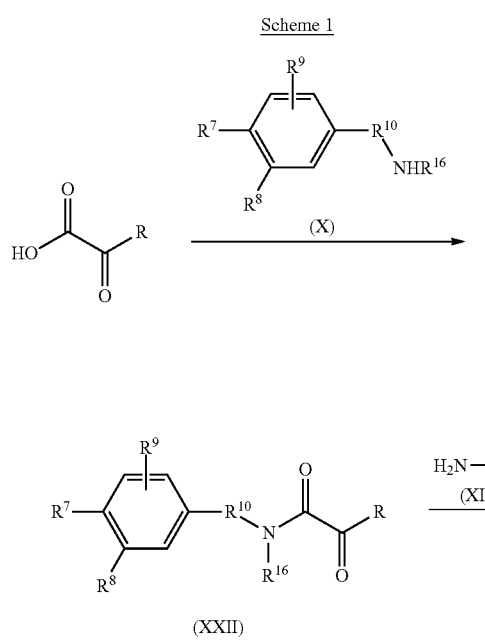
(XXII)
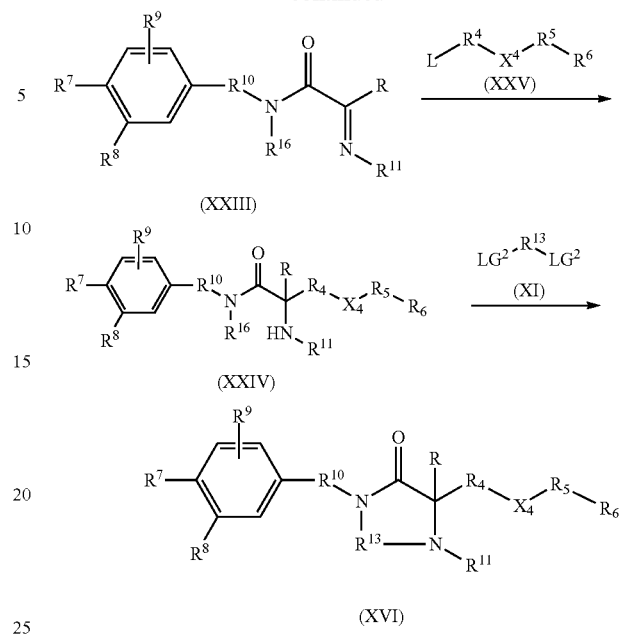
(XXIII) → (XXIV) → (XVI)
Scheme 2
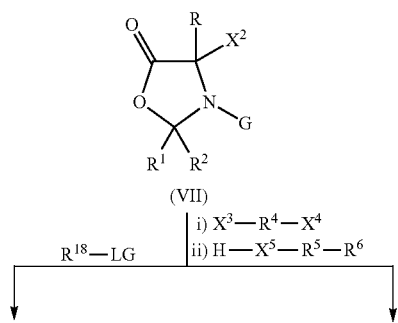
(VII)
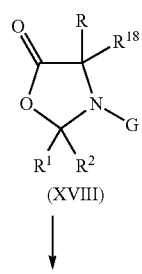
(XVIII)
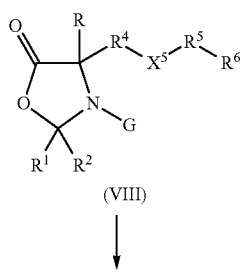
(VIII)

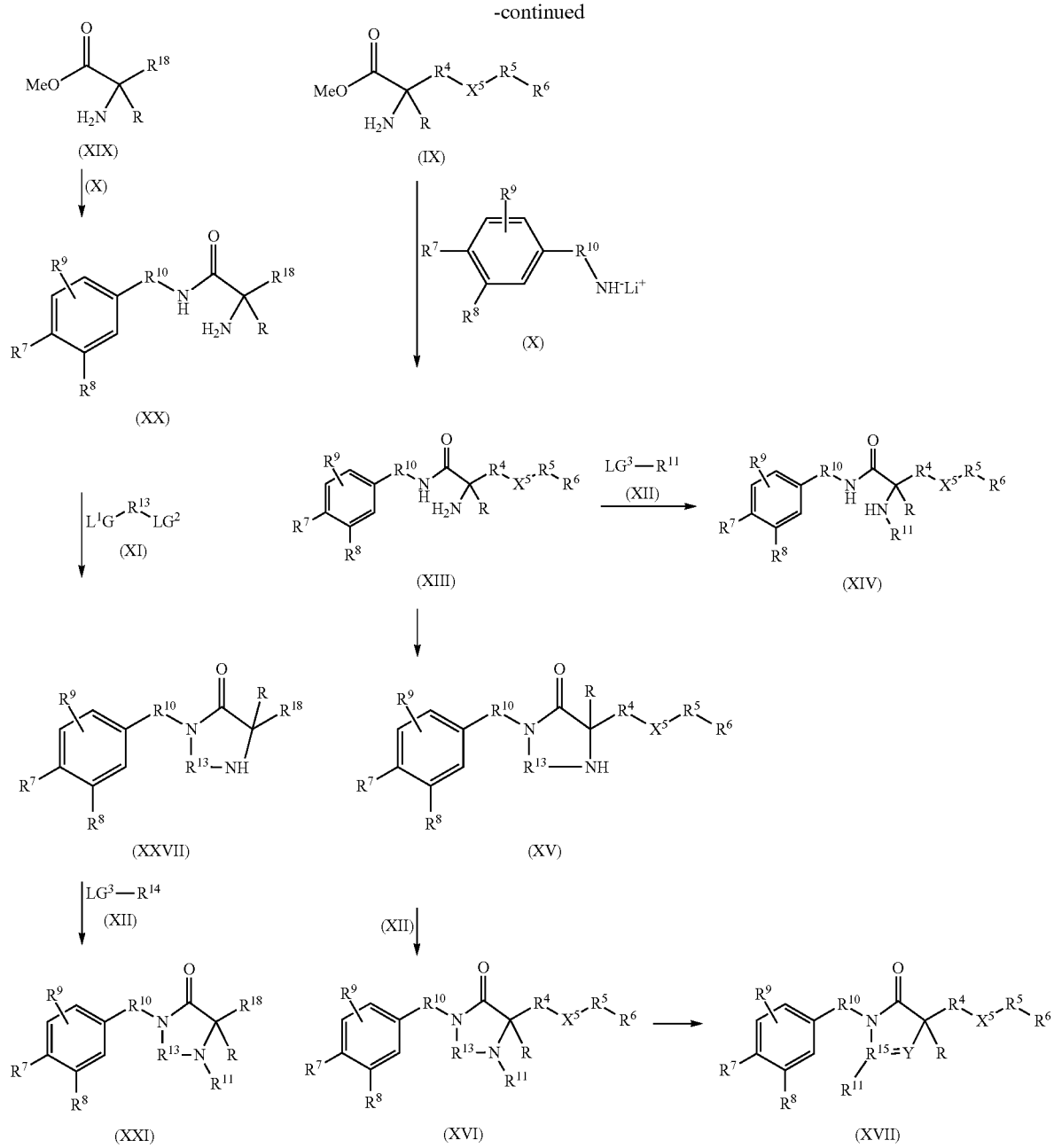

wherein $R^{13}$ is —CO— or —CS—, —SO—, —SO$_2$—, —R$^p$CO—, —R$^p$CS—, —R$^p$SO—, —R$^p$SO$_2$—, wherein R$^p$ is a $C_1$-$C_3$-alkyl;
$R^{15}$ is —C—S—;
$X^5$ is a leaving group as defined herein;
wherein L is selected among the group of metal, metal halide.
In particular, L is selected among Li, MgX$^6$, wherein X$^6$ is halogen;
wherein LG, LG$^-$, LG$^2$ and LG$^3$ are independent leaving groups as defined below; all other substituents are as defined above.

The compounds of general formula XIV, XV, XVI, XVII, XXI and XXIV are comprised in the compounds of formula I or are intermediates thereof.

All compounds that can exist as diastereomeric compounds, when not diastereoisomerically pure, can be easily separated by simple and inexpensive laboratory techniques, such as column chromatography or crystallization procedures.

In one embodiment, this invention provides a method of treating a subject suffering from prostate cancer or a method of delaying the progression of prostate cancer in a subject suffering from prostate cancer or a method for treating a hyperproliferative disorder comprising the step of administering to said subject a compound of formula (I), and/or its isomer, pharmaceutically acceptable salt, pharmaceutical product, crystal, N-oxide, hydrate or any combination thereof, or a composition comprising the same in an amount effective to treat prostate cancer in the subject.

The hyperproliferative disorder may be hormone refractory prostate cancer.

In one embodiment, the present invention provides a composition comprising a compound of formula (I) and/or its isomer, pharmaceutically acceptable salts, pharmaceutical product, crystal or N-oxide, hydrate or any combination thereof. In one embodiment, the compound is a selective androgen receptor modulator (SARM).

In one embodiment, the SARM is a partial antagonist. In one embodiment, the SARM is a partial agonist, or in some embodiments, a tissue-selective agonist.

In one embodiment, this invention provides a method of contraception in a male subject, comprising the step of administering to the subject a compound of formula (I) and/or its isomer, pharmaceutically acceptable salt, pharmaceutical product, crystal, N-oxide, hydrate or any combination thereof, or a composition comprising the same, in an amount effective to suppress sperm production in the subject, thereby effecting contraception in the subject.

In one embodiment, this invention provides a method of hormone therapy comprising the step of contacting an androgen receptor of a subject with a compound of formula (I) and/or its isomer, pharmaceutically acceptable salt, pharmaceutical product, crystal, N-oxide, hydrate or any combination thereof, or a composition comprising the same, in an amount effective to effect a change in an androgen-dependent condition.

In one embodiment, this invention provides a method of treating a bone-related disorder in a subject, or increasing a bone mass in a subject, promoting bone formation in a subject, administering an effective amount of a compound of formula (I) and/or its isomer, pharmaceutically acceptable salt, pharmaceutical product, crystal, N-oxide, hydrate or any combination thereof, or a composition comprising the same, in an amount effective to treat said bone-related disorder. According to this aspect, and in one embodiment, the subject suffers from osteoporosis, osteopenia, bone fracture, bone frailty, loss of bone mineral density (HMD), or any combination thereof. In one embodiment, the method increases, the strength of a bone of said subject. In one embodiment, the compound stimulates or enhances osmioblasiogenesis, or, in another embodiment the compound inhibits osteoclast proliferation.

In one embodiment, this invention provides a method of treating, reducing the incidence of, delaying progression of, reducing the severity of or alleviating symptoms associated with a muscle wasting disorder in a subject, comprising the step of administering to said subject a compound of formula (I) and/or its isomer, pharmaceutically acceptable sail, pharmaceutical product, crystal, N-oxide, hydrate or any combination thereof, or a composition comprising the same, in an amount effective to treat the muscle wasting disorder in said subject.

According to this aspect, and in one embodiment, the muscle wasting disorder is due a pathology, illness, disease or condition. In one embodiment, the pathology, illness, disease or condition is neurological, infectious, chronic or genetic. In one embodiment, the pathology, illness, disease or condition is a muscular dystrophy, a muscular atrophy. X-linked spinal-bulbar muscular atrophy (SBMA), a Cachexia, malnutrition, leprosy, diabetes, renal disease, chronic obstructive pulmonary disease (COPD), cancer, end stage renal failure, sarcopenia, emphysema, osteomalacia, HIV infection. AIDS, or cardiomyopathy.

In one embodiment, the muscle wasting disorder is an age-associated muscle wasting disorder; a disease deconditioning-associated muscle wasting disorder; or the muscle wasting disorder is due to chronic lower back pain; bums; central nervous system (CNS) injury or damage; peripheral nerve injury or damage; spinal cord injury or damage; chemical injury or damage or alcoholism.

In one embodiment, this invention provides a method of treating, reducing the severity of reducing the incidence of delaying the onset of or reducing pathogenesis of diabetes or of glucose intolerance or of hyperinsulinemia or of insulin resistance or of diseases associated with diabetes or of pathogenesis of fatty liver conditions or of reducing the pathogenesis of cardiovascular disease or of reducing the pathogenesis of cachexia in a human subject, comprising administering an effective amount of a compound of formula (I) and/or its isomer, pharmaceutically acceptable salt, pharmaceutical product, crystal, N-oxide, hydrate or any combination thereof, to said subject.

In one embodiment the cachexia is associated with cancer in said subject.

In one embodiment this invention provides a method of treating a disease or condition of the eye comprising Sjogren's syndrome, or xerophthalmia of a subject, comprising the step of administering an effective amount of a compound of formula (I) and/or its isomer, pharmaceutically acceptable salt, pharmaceutical product, crystal, N-oxide, hydrate or any combination thereof, to the subject. In one embodiment, the disease or condition of the eye.

In one embodiment, the present invention provides a method of reducing a fat mass or increasing a lean mass in a subject comprising the step of administering an effective amount of a compound of formula (1) and/or its isomer, pharmaceutically acceptable salt, pharmaceutical product, crystal, N-oxide, hydrate or any combination thereof, to the subject.

In another embodiment, this invention provides a method of treating reducing the severity of reducing the incidence of, delaying the onset of, or reducing pathogenesis of rheumatoid arthritis or reducing pathogenesis of chronic kidney disease or reducing pathogenesis of end stage renal disease or reducing pathogenesis of frailty or reducing pathogenesis of hypogonadism or reducing pathogenesis of age-related functional decline in a subject, comprising the step of administering to said subject a compound of formula (I) and/or its isomer pharmaceutically acceptable salt, pharmaceutical product, crystal, N-oxide, hydrate or any combination thereof, to the subject.

Unless otherwise stated, the terms employed herein have the following meanings:

The term "pharmaceutically acceptable salts" as used herein refers to a compound, which maintain the same biological properties of the parent compound. Not-limitative examples of their preparation include the acid addition salts (formed with the free amino groups of the starting compound) which are formed with inorganic acids such as, for example, hydrochloric or phosphoric acids, or such oranic acids as acetic, oxalic, tartaric, mandelic, and the like. Salts formed from the free carboxyl groups can also be derived from inorganic bases such as, for example, sodium potassium, ammonium, calcium, or ferric hydroxides, and such organic bases as isopropylamine, triethylamine, 2-ethylamoni ethanol, and the like.

Some of the compounds of the present invention may present one or more stereocentres, therefore can be produced as stereoisomers (R)— or (S)— or their mixtures. Therefore, the compounds of the present invention have to be considered as either including their isolated stereoisomers or their racemic mixture.

The compounds of the present invention can be tautomers and/or geometrical isomers (cis/trans isomers) and can be alone or in mixture with each other. Therefore, the term "geometrical isomers" as employed herein refers to isomers, which differ from each other by the spatial orientation of the functional groups linked to a double bond carbon (cis/trans). Therefore, the compounds of the present invention have to be considered as including cis-isomers, trans-isomers and/or their mixtures.

The terms "treatment" or "treat a pathology" as employed herein, refer to a cure and/or a prophylaxis, and/or a therapy for that pathology. The term prophylaxis refers to a therapy able to prevent, and/or partially prevent the pathology occurrence, and/or its worsening, and/or its progression. A "therapy" as used herein, partially or totally alleviates the pathology symptoms and/or reduces and/or eliminates the pathology effects.

The term "halo" or "halogen" as employed herein as such or as a part of another group, refers to chlorine, bromine, fluorine or iodine.

The term "$(C_x-C_y)$alkyl", as employed herein as such or as a part of another group, refers to a straight, branched or cyclized chain radical having x to y carbon atoms. Representative example for $(C_x-C_y)$alkyl include, but are not limited to, methyl, ethyl, n-propyl, n-butyl, n-propyl, isobutyl, sec-butyl, tert-butyl, n-pentyl, isopentyl neopentil, n-hexyl, cyclopentyl, cyclohexyl and the like.

The term "substituted alkyl", as employed herein as such or as a part of another group, refers to a straight, branched or cyclized radical chain, linked to 1 to 9 substituents each selected one independently form the other, in the group of: halogens, cyclic $C_1-C_6$-alkyl, cyclic $C_1-C_6$-heteroalkyl, —OH, alkoxy, amino, ayclamino or carboxy. Whenever the term "substituted alkyl" in connected to $(C_x-C_y)$, this last one refers to the total number of carbon atoms, including those of the substituent.

The term "substituted heteroalkyl", as employed herein as such or as a part of another group, refers to a straight, branched or cyclized radical chain where at least one is an heteroatom such as —N—, —O—, —S—, —NR$^g$, —SO$_2$— where R$^g$ is H or $(C_1-C_4)$ alkyl as defined herein, and linked to 1 to 9 substituents each selected one independently form the other, in the group of: halogens, cyclic $C_1-C_6$-alkyl, cyclic $C_1-C_6$-heteroalkyl, —OH, alkoxy, amino, ayclamino or carboxy. Whenever the term "substituted heteroalkyl" in connected to $(C_x-C_y)$, this last one refers to the total number of carbon atoms, including those of the substituent.

The term "$(C_x-C_y)$heteroalkyl", as employed herein as such or as a part of another group, refers to a straight, branched or cyclized chain radical having x to y atoms where at least one is an heteroatom such as —N—, —O—, —S—, —NR$^g$, —SO$_2$— where R$^g$ is H or $(C_1-C_4)$alkyl as defined herein.

The term "$(C_x-C_y)$alkenyl", as employed herein as such or as a part of another group, refers to a straight, branched or cyclized chain radical having x to y carbon atoms, containing (a) double bond(s).

The term "hydroxy", as employed herein as such or as a part of another group, refers to an —OH group.

The term "hydroxy$(C_x-C_y)$alkyl", as employed herein, refers to at least one hydroxy group as defined herein, appended to the parent molecular moiety though an $(C_1-C_7)$ alkyl group, as defined herein. Representative examples of hydroxy$(C_x-C_y)$alkyl include, but are not limited to, hydroxymethyl, 2,2-dihydroxyethyl, 1-hydroxyethyl, 3-hydroxypropyl, 1-methyl-1-hydroxypropyl, and the like.

The term "cyano", as employed herein as such or as a part of another group, refers to an —CN group.

The term "amino", as employed herein as such or as a part of another group, refers to an —NH$_2$ group.

The term "nitro", as employed herein as such or as a part of another group, refers to an —NO$_2$ group.

The term "carbamoyl methyl", as employed herein as such or as a part of another group, refers to a —CH$_2$—CONH$_2$ group.

The term "per-fluoro", as employed herein refers to a group bearing a $(C_x-C_y)$alkyl, which will be completely substituted with fluorine atoms. Representative, but not exclusive examples of per-fluorinated compounds are —CF$_3$ or —S—CF$_2$—CF$_3$.

The term "alkyl-thio", as employed herein refers to a —SR$^m$ group, where R$^m$ is an alkyl group as defined herein.

The term "alkyl-sulfinyl", as employed herein refers to a —SOR$^m$ group, where R$^m$ is an alkyl group as defined herein.

The term "alkyl-sulfonyl", as employed herein refers to a —SO$_2$R$^m$ group, where R$^m$ is an alkyl group as defined herein.

The term "mono- or di(Ci-C7)alkyl amino", as employed herein as such or as part of another group, refers to one or two $(C_1-C_7)$alkyl group(s), as defined herein, appended to the parent molecular moiety through an amino group, as defined herein. Representative examples of mono- or di$(C_1-C_7)$alkyl amino include, but are not limited to methylamino, ethylamino, propylamino, butylamino, dimethylamino, diethylamino, and the like.

The term "$(C_1-C_7)$alkoxy", as employed herein as such or as part of another group, refers to —O—$(C_1-C_7)$alkyl, wherein —$(C_1-C_7)$alkyl is as defined herein. Representative examples of $(C_1-C_7)$alkoxy include, but are not limited to methoxy, ethoxy, propoxy, butoxy, isobutoxy, sec-butoxy, tert-butoxy, and the like.

The term "$(C_1-C_7)$alkoxy$(C_1-C_7)$alkyl", as employed herein, refers to at least one $(C_1-C_7)$alkoxy group, as defined herein, appended to the parent molecular moiety through an (C1-C7)alkyl group, as defined herein. Representative examples of (Ci-C7)alkoxy(Ci-C7)alkyl include, but are not limited to methoxymethyl, ethoxymethyl, 2-methoxyethyl, 2-ethoxyethyl, 3,3-dimethoxypropyl, 2,4-dimethoxybutyl and the like.

The term "$(C_2-C_7)$acyl" as employed herein by itself or as part of another group refers to alkylcarbonyl or alkenylcarbonyl group having 2 to 7 carbon atoms, and examples thereof include acetyl, propanoyl, isopropanoyl, butanoyl, sec-butanoyl, tert-butanoyl and pentanoyl.

The term "$(C_2-C_7)$acyl amino" as employed herein by itself or as part of another group refers to a group having formula —NCO—$(C_2-C_7)$acyl.

The term "aryl" as employed herein as such or as a part of another group, refers to an aromatic carbocyclic ring system having a single radical containing 6 or more carbon atoms. An aryl group may be a fused or polycyclic ring system. Representative, but not exclusive examples of aryl groups include phenyl and napthyl.

The term "heteroaryl" as employed herein as such or as a part of another group, refers to an aromatic monocyclic or fused or polycyclic ring system having at least five ring atoms in which one or more of the atoms in the ring system is other than carbon, for example, nitrogen (including N-oxide), oxygen or sulfur. In a bicyclic aromatic radical only one ring, containing a heteroatom, need to be aromatic. Representative but not exclusive examples of heteroaryl include pyridyl, pyrrolyl, pyrazolyl, imidazolyl, thienyl, furanyl, indolyl, indolizinyl, azaindolizinyl, quinolyl, pyrazinyl, pyrimidinyl, pyridazinyl, oxazolyl, isoxazolyl, benzoxazolyl, benzisoxazolyl, benzothiazolyl, isoquinolinyl, benzimidazolyl, benztriazolyl, benzofuranyl, benzothienyl, benzopyranyl, imidazo[2,1-b]thiazolyl, imidazo[1,2-a]pyridyl, imidazo[1,2-a]pyrimidinyl, pyrazolo[1,5-a]pyridyl, imidazolyl, triazolyl, thiadiazolyl, oxadiazolyl, thiazolyl, triazalopyrimidinyl, pyrazolopyrimidinyl, thienopyridinyl, pyrrolopyridinyl 4,5,6,7-tetrahydrobenzisoxazolyl, indazolyl, 4,5,6,7-tetrahydroindazolyl, and 4,5,6,7-tetrahydrobenzothienyl.

The term "arylalkyl" as employed herein as such or as a part of another group, refers to a $(C_x-C_y)$alkyl group substituted with an optionally substituted aryl group, wherein the terms alkyl and aryl have been previously defined. Representative examples of aralkyl groups include benzyl, phenethyl, alpha-methylbenzyl, picolyl, and the like, and may be optionally substituted. "Optionally substituted" is intended to include both substituted and unsubstituted.

The term "heteroarylalkyl" as employed herein as such or as a part of another group, refers to an alkyl group substituted with an with an optionally substituted heteroaralaryl group, wherein the terms alkyl and heteroaryl has been previously described.

The term "substituted" as used herein in connection with various residues refers to halogen substituents, such as fluorine, chlorine, bromine, iodine, or $(C_1-C_7)$alkyl, halo$(C_1-C_7)$ alkyl, hydroxy, amino, $(C1-C_7)$alkoxy, $(C_2-C_7)$acyl, $(C_1-C7)$ alkylamino, amino$(C1-C_7)$alkyl, nitro, cyano, thiol carbamoylmethyl, $(C_1-C_7)$hydroxy, amino, trifluoromethyl, N-methylsulfonylamino, substituents. The "substituted" groups may contain 1 to 3, preferably 1 or 2, most 5 preferably 1 of the above mentioned substituents.

The term "leaving group" as used herein is a molecular fragment that departs with a pair of electrons in heterolytic bond cleavage. Representative, but not exclusive leaving groups can be anions or neutral molecules. Common anionic leaving groups are halides such as Cl⁻, Br⁻, and I⁻, and sulfonate esters, such as mesylate or sulfonate, imydazole, —O-pyridyl, para-toluenesulfonate or "tosylate" (TsO⁻).

Common neutral molecule leaving groups are water ($H_2O$), ammonia ($NH_3$), and alcohols (ROH).

The present invention will now be described with reference to the included figures, which represent non limiting examples of the present invention:

FIGS. 1-29 cytotoxic activity of (R)-Bicalutamide and compounds (R)/(S)-23, (R)/(S)-27, (R)/(S)-28, (R)/(S)-29, (R)/(S)-30, (R)/(S)-31, (R)-13, (S)-24, (S)-32, (S)-36, (R)-10, (R)-11, (S)-37, (R)/(S)-8, (R)/(S)-9, (R)/(S)-22, (R)/(S)-26, (S)-14d at different concentration (0.02, 0.2, 2, 20 μM) after 144 h exposure. On the x-axis is reported the concentration, while on the y-axis is reported the inhibition of the net growth (% net growth).

FIGS. 30-34 illustrate the cytotoxic effect and apoptotic activity of compounds (S)-22, (S)-26, (R)-9, (S)-37 and (R)-10 on PC-3 and DU-145 cell lines at different concentration (0.02, 0.2, 2, 20 μM) after 144 h exposure. On the x-axis is reported the concentration, while on the y-axis is reported the inhibition of the net growth (% net growth).

In the tables legends of FIG. 38-43:

(1) Plasmid transfected cells+ARE-luc+β-galactosidase, without human AR;

(2) Plasmid transfected cells+ARE-luc+β-galactosidase+hAR;

(3) Plasmid transfected cells+ARE-luc+β-galactosidase+hAR+R1881 (10 nM) [androgen].

For each experiment, the ectopically expressed hAR was detected by Western blot, as described in the following section. Similar amounts of hAR were expressed in each experiment. Data have been obtained from two independent experiments. Mean is shown (SEM<1).

Figure 38:
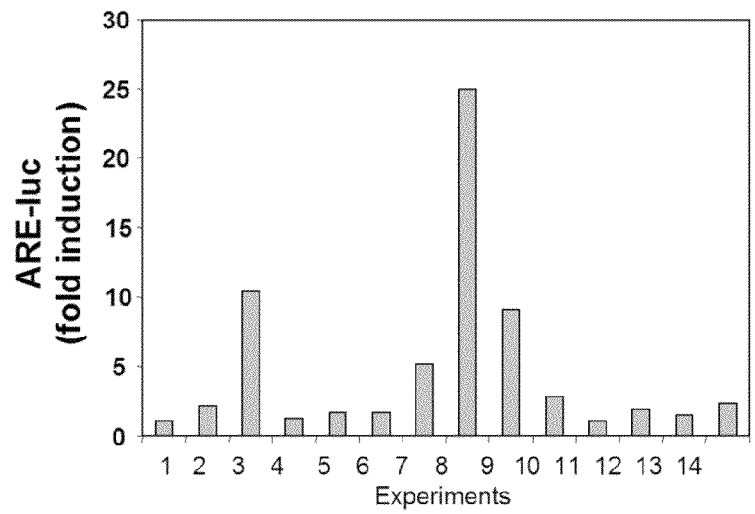
FIGS. 38-43 illustrate the quantification of the human androgen receptor transcriptional activity in the presence of compounds: (R)-22, (R)-9, (R)-8, (R)-12, (R)-26, (S)-7c, (S)-14e, (R)-26, (R)-11.

FIG. 38 Quantification of the human androgen receptor transcriptional activity in the presence of compounds (R)-22 and (R)-9.

| Experiment | Conditions | Compound (concentration) |
| --- | --- | --- |
| 1 | Control (1) | none |
| 2 | (2) | none |
| 3 | (3) | none |
| 4 | (3) | Casodex (10 μM) |
| 5 | (3) | (R)-22 (10 μM) |
| 6 | (2) | (R)-22 (10 nM) |
| 7 | (2) | (R)-22 (100 nM) |
| 8 | (2) | (R)-22 (1 μM) |
| 9 | (2) | (R)-22 (10 μM) |
| 10 | (3) | (R)-9 (10 μM) |
| 11 | (2) | (R)-9 (10 nM) |
| 12 | (2) | (R)-9 (100 nM) |
| 13 | (2) | (R)-9 (1 μM) |
| 14 | (2) | (R)-9 (10 μM) |

Figure 39:
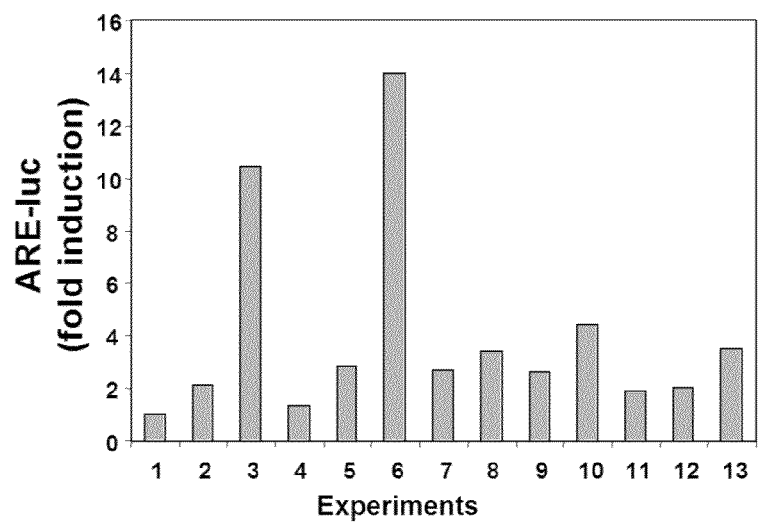

FIG. 39 Quantification of the human androgen receptor transcriptional activity in the presence of compounds (R)-8 and (R)-12.

| Experiment | Conditions | Compound (concentration) |
| --- | --- | --- |
| 1 | Control (1) | none |
| 2 | (2) | none |
| 3 | (3) | none |
| 4 | (3) | Casodex (10 μM) |
| 5 | (3) | (R)-8 (10 μM) |
| 6 | (3) | (R)-12 (10 μM) |
| 7 | (2) | (R)-8 (10 nM) |
| 8 | (2) | (R)-8 (1 μM) |
| 9 | (2) | (R)-8 (10 μM) |
| 10 | (2) | (R)-12 (10 nM) |
| 11 | (2) | (R)-12 (100 nM) |
| 12 | (2) | (R)-12 (1 μM) |
| 13 | (2) | (R)-12 (10 μM) |

Figure 40:
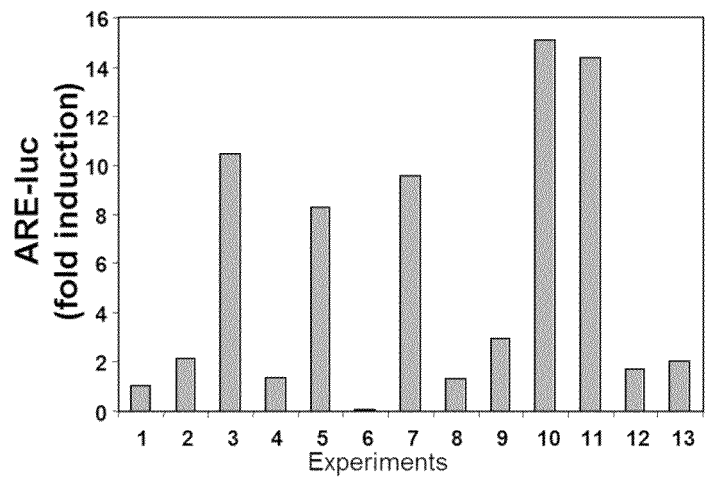

FIG. 40 Quantification of the human androgen receptor transcriptional activity in the presence of compounds (R)-26 and (S)-7c.

| Experiment | Conditions | Compound (concentration) |
|---|---|---|
| 1 | Control (1) | none |
| 2 | (2) | none |
| 3 | (3) | none |
| 4 | (3) | Casodex (10 μM) |
| 5 | (3) | (R)-26 (10 μM) |
| 6 | (3) | (R)-26 (10 nM) |
| 7 | (2) | (R)-26 (100 nM) |
| 8 | (2) | (R)-26 (1 μM) |
| 9 | (2) | (R)-26 (10 μM) |
| 10 | (2) | (R)-7c (10 nM) |
| 11 | (2) | (R)-7c (100 nM) |
| 12 | (2) | (R)-7c (1 μM) |
| 13 | (2) | (R)-7c (10 nM) + Casodex (10 μM) |

Figure 41:
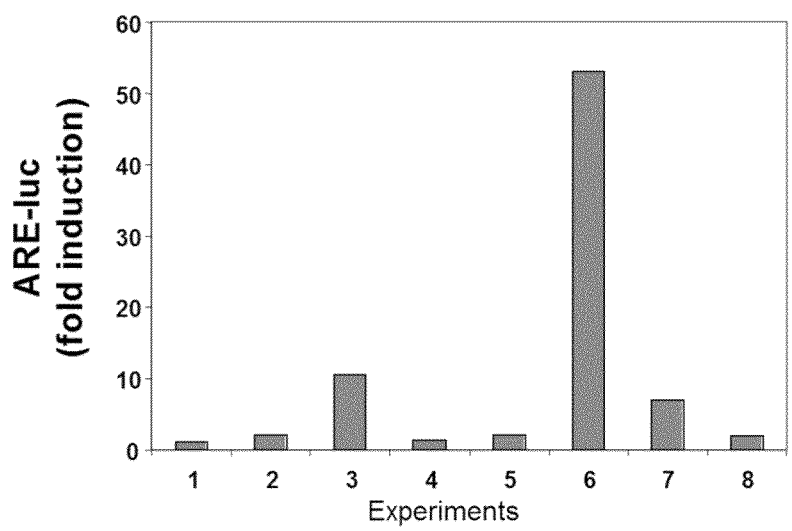

FIG. 41 Quantification of the human androgen receptor transcriptional activity in the presence of compounds (S)-14e.

| Experiment | Conditions | Compound (concentration) |
|---|---|---|
| 1 | Control (1) | none |
| 2 | (2) | none |
| 3 | (3) | none |
| 4 | (3) | Casodex (10 μM) |
| 5 | (2) | (S)-14e (10 nM) |
| 6 | (2) | (S)-14e (100 nM) |
| 7 | (2) | (S)-14e (1 μM)) |
| 8 | (2) | (S)-14e (10 nM) + Casodex (10 μM) |

Figure 42:
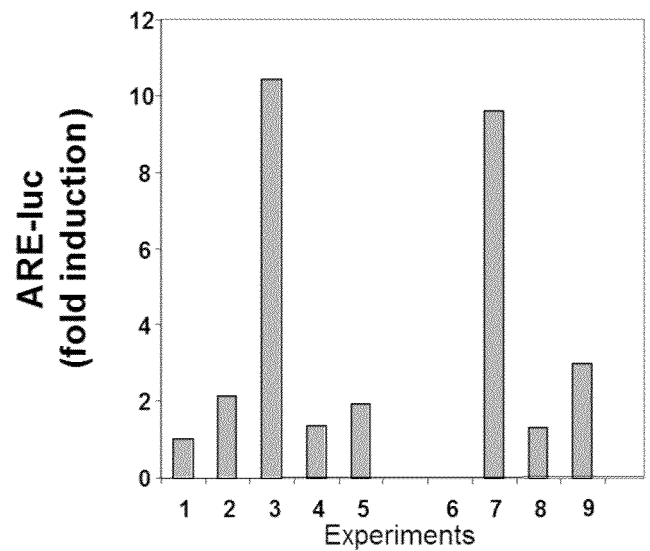

FIG. 42 Quantification of the human androgen receptor transcriptional activity in the presence of compounds (R)-26.

| Experiment | Conditions | Compound (concentration) |
|---|---|---|
| 1 | Control (1) | none |
| 2 | (2) | none |
| 3 | (3) | none |
| 4 | (3) | Casodex (10 μM) |
| 5 | (3) | (S)-26 (10 μM) |
| 6 | (2) | (S)-26 (10 nM) |
| 7 | (2) | (S)-26 (100 nM) |
| 8 | (2) | (S)-26 (1 μM) |
| 9 | (2) | (S)-26 (10 μM) |

Figure 43:
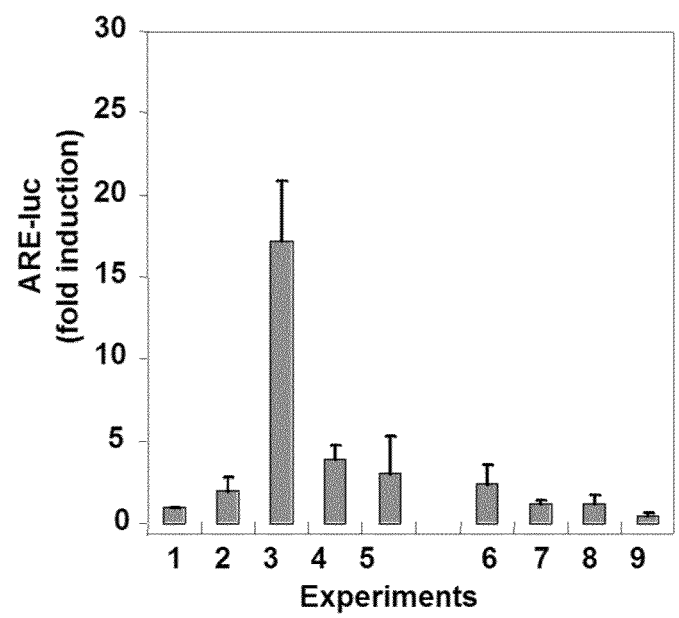

FIG. 43 Quantification of the human androgen receptor transcriptional activity in the presence of compounds (R)-11.

| Experiment | Conditions | Compound (concentration) |
|---|---|---|
| 1 | Control (1) | none |
| 2 | (2) | none |
| 3 | (3) | none |
| 4 | (3) | Casodex (10 μM) |
| 5 | (3) | (R)-11 (10 μM) |
| 6 | (2) | (R)-11 (10 nM) |
| 7 | (2) | (R)-11 (100 nM) |
| 8 | (2) | (R)-11 (1 μM) |
| 9 | (2) | (R)-11 (10 μM) |

Data have been obtained from three independent experiments. Mean and SEM are shown.

Figure 44:
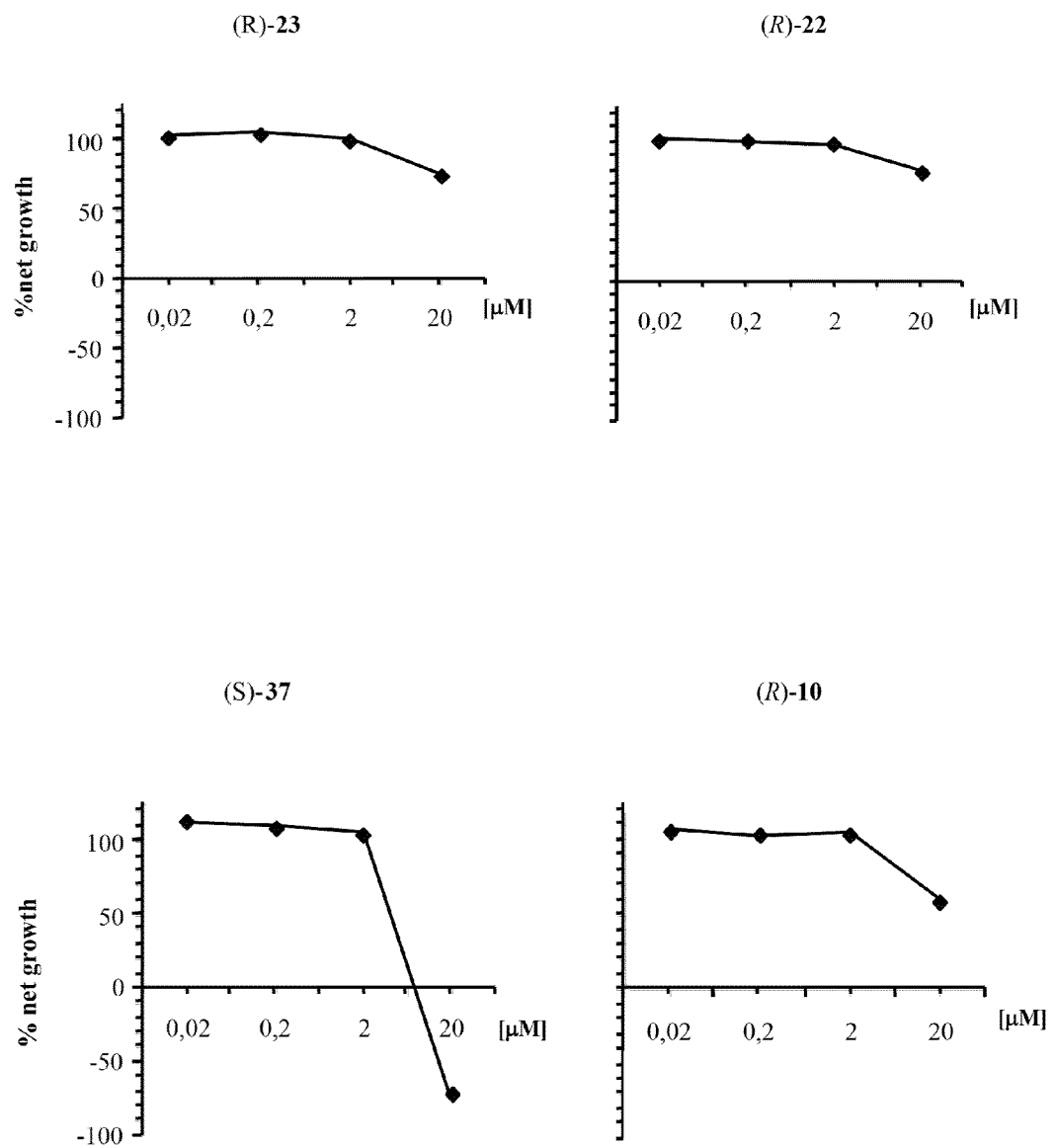

FIG. 44 Cytotoxic activity of the drugs on the human hepatoblastoma cell line HepG2.

Further details of the present invention will result from the following description of some, not-limitative examples.

EXAMPLES OF SYNTHESIS

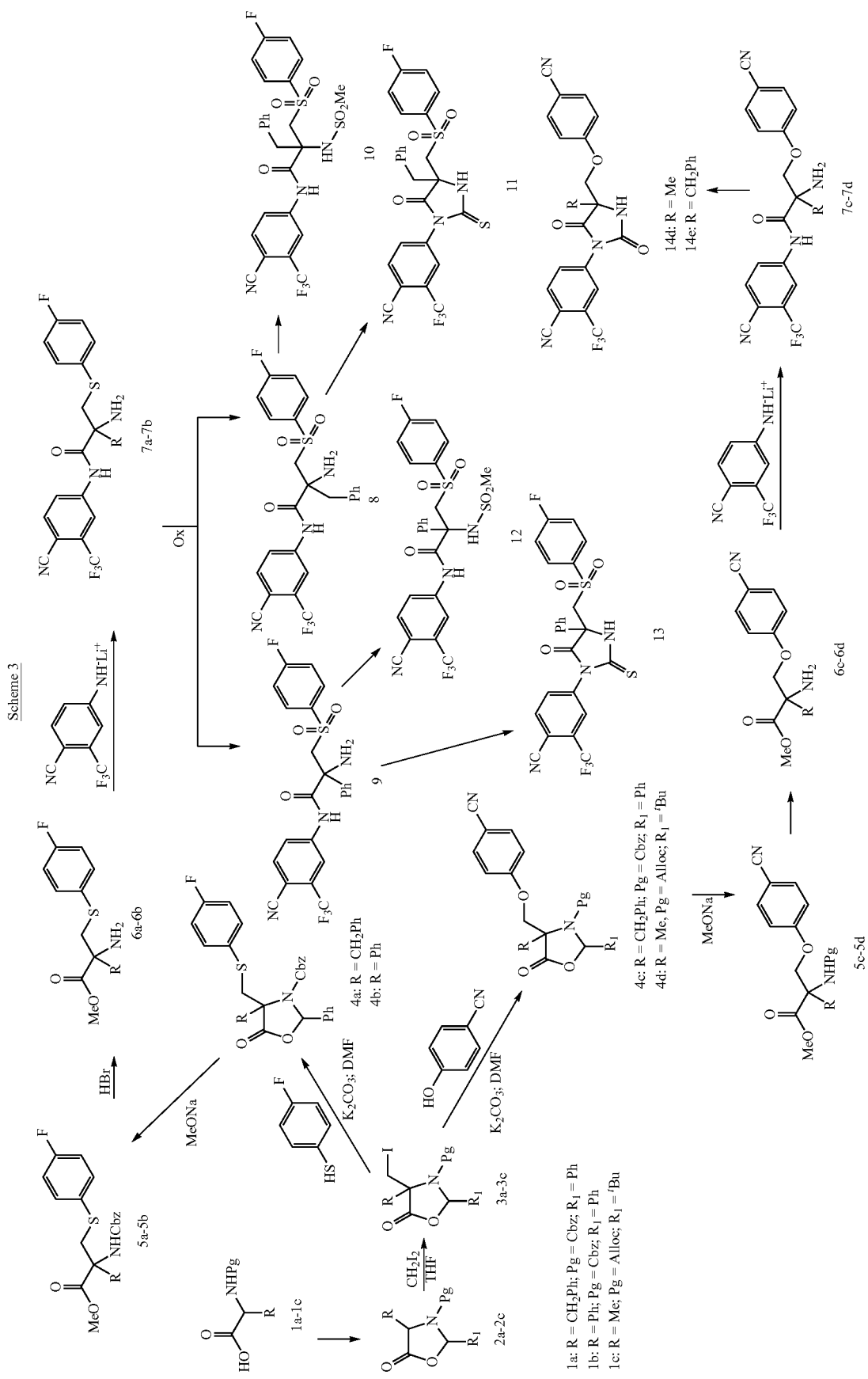

Scheme 4
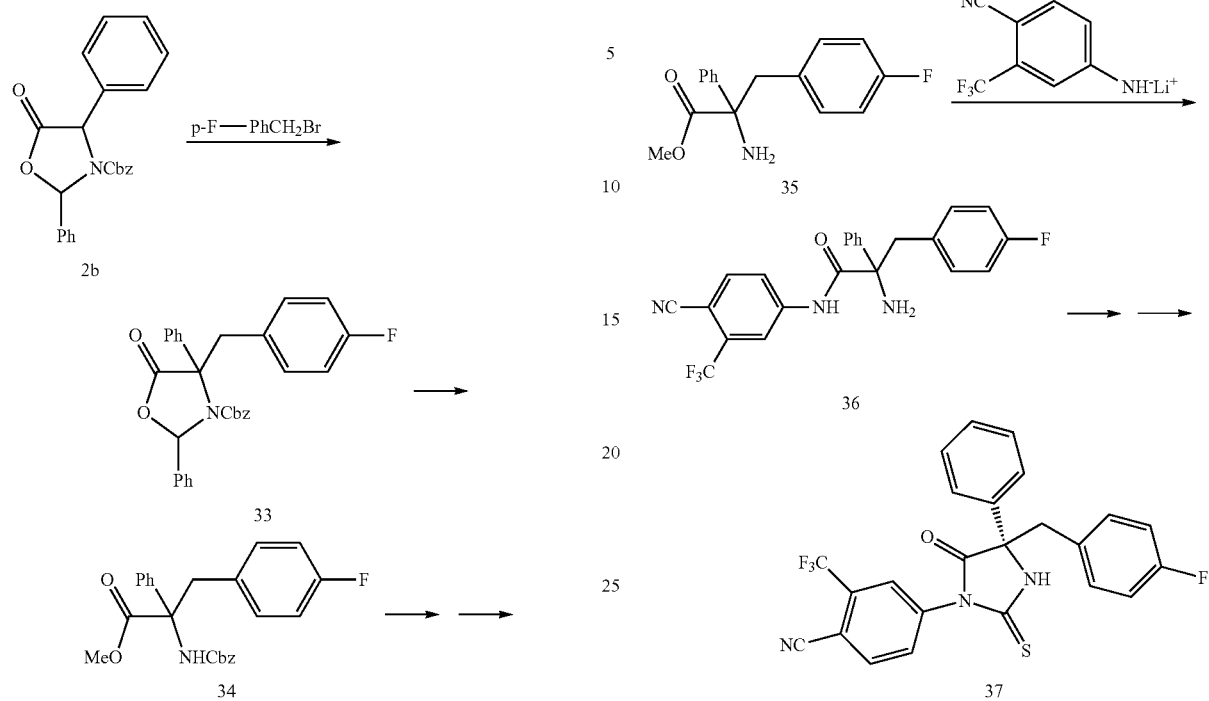

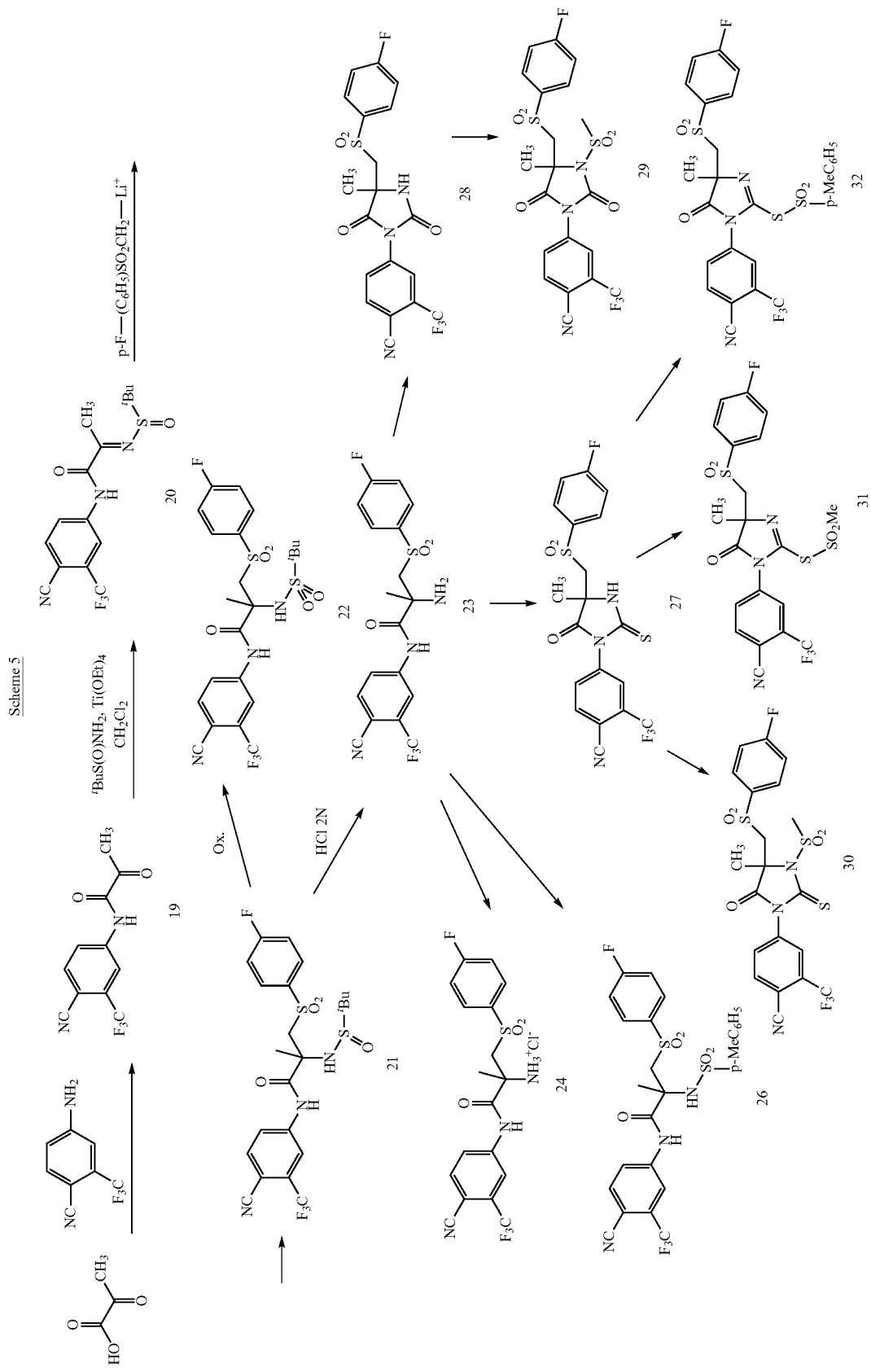

Compounds 1a-1b; 2a-2b and 3a-3b were obtained according to literature procedures [B. L. Kedrowsky and C H. Heatcock *Heterocycles* 2002, 601-634]

Example 1

Synthesis of cis-4a: (2R,4R)-benzyl 4-benzyl-4-((4-fluorophenylthio)methyl)-5-oxo-2-phenyloxazolidine-3-carboxylate To a solution of 3a (6 eq.) in anhydrous dimethlyformamide (DMF) (3 mL), 2 eq. of potassium carbonate were added, followed by 4-fluorobenzenethiol (1.6 eq). The reaction mixture was allowed to stir at room temperature for 3 hours (hrs) than water and ethyl acetate were added. The organic layer was than washed with 0.1N HCl. The crude material was purified by silica gel column chromatography (c-Hex/Et$_2$O=4/1) and than crystallised from pentane. (Yield: 95%)

The same procedure was applied for the synthesis of 4b, 4c 4d and 4e starting from he corresponding iodides (3b-e).

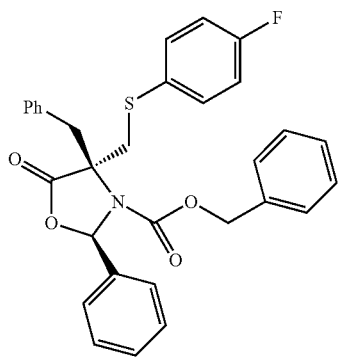 [SMILES: O=C(OCc1ccccc1)N1[C@@H](c2ccccc2)OC(=O)[C@@]1(CSc1ccc(F)cc1)Cc1ccccc1]

cis-4a: $^1$H NMR (400 MHz, C$_6$D$_6$): 7.23 (d, J=7.2 Hz, ArH), 7.12-6.89 (m, 9H, ArH), 6.76 (t, J=8 Hz, 2H, ArH), 6.47 (t, J=6.8 Hz, 2H, ArH), 6.27 (s, 1H, CH), 6.05 (d, J=8.4 Hz, 2H, ArH), 4.75 (d, J=12.4 Hz, 1H, CH$_2$), 4.30 (d, J=12.4 Hz, 1H, CH), 4.10 (d, J=14.4 Hz, 1H), 3.56 (d, J=13.2 Hz, 1H), 3.16 (d, J=13.2 Hz, 1H), 3.15 (d, J=14.4 Hz, 1H).

$^{13}$C NMR (100 MHz, CDCl$_3$): 172.0, 1662.0 (d), 152.2, 136.6, 135.9, 135.6, 133.5, 133.4, 130.9, 129.6, 129.2, 129.1, 128.8, 128.1, 128.0, 127.9, 127.8, 127.6, 127.4, 116.3, 116.1, 90.8, 70.1, 67.1, 41.3, 41.2.

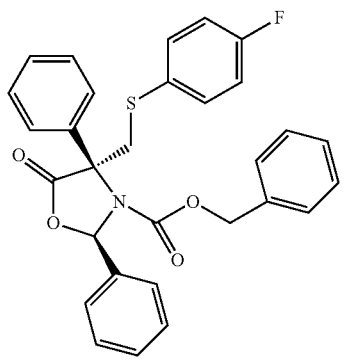 [SMILES: O=C(OCc1ccccc1)N1[C@@H](c2ccccc2)OC(=O)[C@@]1(CSc1ccc(F)cc1)c1ccccc1]

cis-4b (2 rotamers at room temperature): $^1$H NMR (400 MHz, CDCl$_3$): 7.61-7.21 (m, 30H, ArH), 7.19-6.89 (m, 8H, ArH), 6.83 (s, 1H), 6.63 (s, 1H), 5.10-4.90 (m, 3H, CH$_2$), 4.82 (d, J=14 Hz, 1H, CH$_2$), 4.48 (d, J=14 Hz, 1H, CH$_2$), 4.01 (q, J=7 Hz, 2H, CH$_2$), 3.82 (d, J=14 Hz, 1H, CH$_2$).

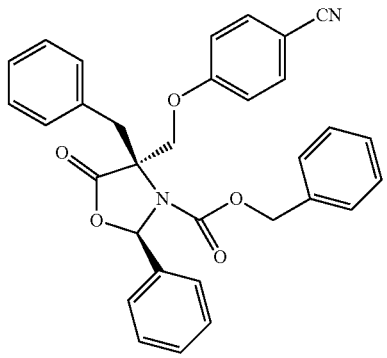 [SMILES: N#Cc1ccc(OC[C@@]2(Cc3ccccc3)C(=O)O[C@H](c3ccccc3)N2C(=O)OCc2ccccc2)cc1]

cis-4c (rotamers mixture): $^1$H NMR (400 MHz, CDCl$_3$): 7.60 (d, J=8.4 Hz, 2H, ArH, major), 7.57 (d, J=7.0 Hz, 2H, ArH, minor), 7.39-6.96 (m, 24H, ArH, minor+major), 6.98 (d, J=7.2 Hz, 2H, ArH, minor), 6.69 (d, J=7.8 Hz, 2H, ArH, major), 6.41 (s, 1H, ArH), 6.27 (s, 1H, ArH), 6.19 (d, J=7.2 Hz, 2H, ArH), 5.39 (d, J=8.1 Hz, 1H, minor), 5.02-4.98 (m, 3H), 4.84 (d, J=10.2 Hz, 2H), 4.43 (d, J=7.1 Hz, 1H), 4.35 (d, J=8.8 Hz, 2H), 3.60 (d, J=12.8 Hz, 2H), 3.31 (d, J=J=12.8 Hz, 2H). $^{13}$C NMR (100 MHz, CDCl$_3$): 171.8, 160.9, 135.9, 135.3, 134.4 (d), 130.9, 129.8, 129.4, 129.0, 128.5, 128.4, 128.3, 128.1, 127.8, 119.0, 115.8, 105.7, 90.9, 69.2, 68.9, 67.7, 36.9, 30.4, 27.1.

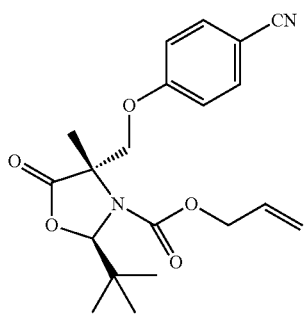 [SMILES: C=CCOC(=O)N1[C@@H](C(C)(C)C)OC(=O)[C@]1(C)COc1ccc(C#N)cc1]

cis-4e (eluent: c-Hex/EtOAc=4/1): $^1$H NMR (400 MHz, Aceton): 7.71 (d, J=8.4 Hz, 2H, ArH), 7.13 (d, J=8.4 Hz, 2H, ArH), 5.82-5.79 (m, 1H, CH$_{vinyl}$), 5.77 (s, 1H, CH), 5.23 (d, J=16.4 Hz, CH$_{2vinyl}$), 5.07 (d, J=9.6 Hz, CH$_{2vinyl}$), 4.66-4.98 (bs, 1H, CH$_2$), 4.54 (dd, J$_1$=13.2 Hz, J$_2$=5.6 Hz, 1H, CH$_2$), 4.30 (dd, J$_1$=13.2 Hz, J$_2$=6.0 Hz, 1H, CH$_2$), 4.27 (bd, J=6.4 Hz, 1H, CH$_2$), 1.62 (s, 3H, CH$_3$), 1.01 (s, 9H, $^t$Bu).

$^{13}$C NMR (100 MHz, Aceton): 173.7, 161.2, 134.3, 132.4, 118.6, 118.4, 116.1, 106.3, 95.5, 66.4, 63.1, 37.9, 24.7, 19.3.

Example 2

Synthesis of (S)-15: (2S,4S)-benzyl 4-(4-fluorobenzyl)-5-oxo-2,4-diphenyloxazolidine-3-carboxylate A solution of 2b (0.5 mmol) in dry THF (3 mL) was added to a solution of LHMDS (1.5 mmol), HMPA (1.5 mL) and dry THF (5 mL) cooled at −78° C. the reaction mixture was stirred at this temperature for 30 min and p-F-benzyl bromide (2.5 eq.) dissolved in THF (3 mL) was added drop wise. The temperature was allowed to rise till −50° C. during 2 h, than 0.1 N HCl was added to quench the reaction mixture. The organic layer was extracted with ethyl acetate and washed several times with 0.1N HCl to remove excess of HMPA. The crude material was purified by silica gel chromatography. Isolated yield: 90%.

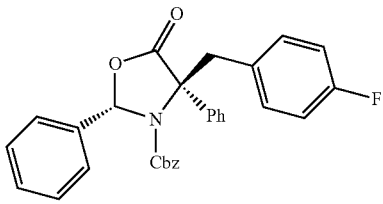 [SMILES: O=C(OCc1ccccc1)N1[C@H](c2ccccc2)OC(=O)[C@]1(Cc1ccc(F)cc1)c1ccccc1]

(S)-33 ¹H NMR (400 MHz, C₆D₆): 7.78 (d, J=7.2 Hz, 1H, ArH), 7.26-7.03 (m, 10H, ArH), 6.98-6.79 (m, 5H, ArH), 6.72-6.64 (m, 3H, ArH), 5.57 (s, 1H, CH), 4.89 (d, J=12.0 Hz, 1H, CH₂), 4.50 (d, J=12.0 Hz, 1H, CH₂), 4.17 (d, J=13.6 Hz, 1H, CH₂), 3.55 (d, J=12.0 Hz, 1H, CH₂).

¹³C NMR (100 MHz, C₆D₆): 172.1, 163.9 (d), 161.4, 152.4, 144.0, 138.0, 137.1, 135.7, 132.2 (d), 129.6, 128.7, 128.5, 128.3, 128.1, 127.9, 127.6, 127.1, 115.6 (d), 89.6, 67.3, 40.8.

Example 3

Synthesis of (R)-5a: (R)-methyl 2-benzyl-2-(benzyloxycarbonylamino)-3-(4-fluorophenylthio)propanoate 2 equivalents of sodium methylate (1 M in methanol) were added to a solution of cis-4a dissolved in dry THF at 0° C. the reaction mixture was stirred at this temperature for 3 h and than quenched with 0.1 M HCl and the organic layer was extracted with ethyl acetate. The crude material was purified by silica gel column chromatography (eluent: c-Hex/EtOAc=4/1) Isolated yield: 90%.

The same procedure was applied for the synthesis of 5b, 5c, 5d and 34 starting respectively from 4b-d and 33.

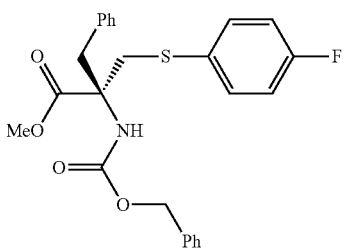 [SMILES: COC(=O)[C@@](CSc1ccc(F)cc1)(Cc1ccccc1)NC(=O)OCc1ccccc1]

(R)-5a: ¹H NMR (400 MHz, CDCl₃): 3.69 (s, 3H, CH₃), 3.79 (d, J=13.6 Hz, 1H, CH₂), 3.96 (d, J=13.2 Hz, 1H, CH₂), 4.96 (d, J=12.4 Hz, 1H, CH₂), 5.20 (d, J=12.0 Hz, 1H, CH₂), 6.18 (s, 1H, NH), 6.82-6.87 (m, 4H, ArH), 7.47-7.31 (m, 10H, ArH).

¹³C NMR (100 MHz, CDCl₃): 172.5, 162.1 (d), 154.3, 139.3, 136.8, 131.7 (t), 128.9, 128.7, 128.7, 128.5, 128.3, 126.2, 115.4, 115.2, 66.8, 66.3, 53.4, 38.1.

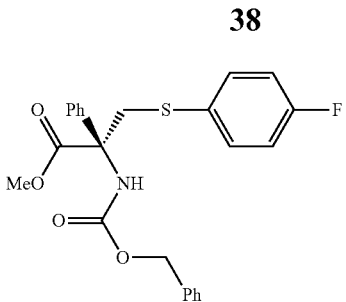

(R)-5b (eluent: c-Hex/Et₂O=4/1): ¹H NMR (400 MHz, C₆D₆): 2.97 (s, 3H, CH₃), 3.96 (d, J=13.6 Hz, 1H, CH₂), 4.57 (d, J=13.2 Hz, 1H, CH₂), 4.80-4.70 (m, 2H, CH₂), 6.53 (s, 1H), 6.55 (t, J=8.8 Hz, 2H, ArH), 7.16-6.93 (m, 10H, ArH), 7.33 (d, J=8 Hz, 2H, ArH). ¹³C NMR (100 MHz, C₆D₆): 171.5, 162.9 (d), 153.9, 136.7, 134.3 (d), 131.0 (d), 128.7, 128.4, 128.2, 128.1, 127.9, 127.8, 127.6, 126.2, 115.8 (d), 66.6 (d), 52.5.

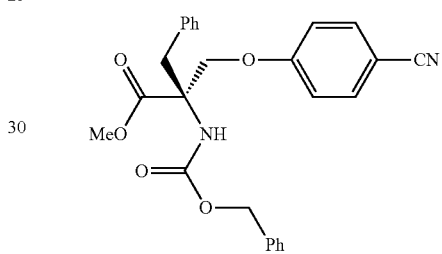

(S)-5c: ¹H NMR (400 MHz, CDCl₃): 7.55 (d, J=8.8 Hz, 2H, ArH), 7.33-7.20 (m, 8H, ArH), 6.95 (t, J=10 Hz, 2H, ArH), 5.76 (bs, 1H, NH), 5.16 (d, J=12 Hz, 1H, CH₂), 5.02 (d, J=12 Hz, 1H, CH₂), 4.87 (d, J=9.2 Hz, 1H, CH₂), 4.36 (d, J=9.6 Hz, 1H, CH₂), 3.77 (s, 3H, CH₃), 3.59 (d, J=13.6 Hz, 1H, CH₂), 3.10 (d, J=13.2 Hz, 1H, CH₂). ¹³C NMR (100 MHz, CDCl₃): 171.1, 161.8, 154.8, 134.4, 134.2, 129.9, 128.8, 128.7, 128.5, 128.3, 127.6, 119.3, 115.8, 104.9, 68.8, 66.8, 65.2, 53.2.

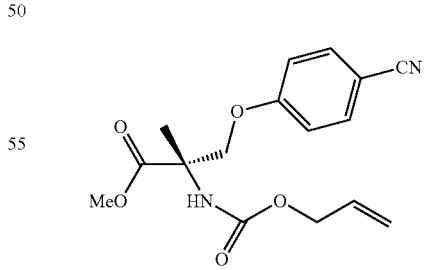

(S)-5d (eluent: c-Hex/Et₂O=3/1): ¹H NMR (400 MHz, CDCl₃): 7.55 (d, J=8.8 Hz, 1H, ArH), 6.93 (d, J=8.8 Hz, 1H, ArH), 5.88-5.76 (m, 2H, CH$_{vinyl}$+NH), 5.25 (d, J=17.2 Hz, CH$_{2vinyl}$), 5.16 (d, J=11.6 Hz, CH$_{2vinyl}$), 4.47-4.49 (m, 3H, CH₂), 4.32 (d, J=9.2 Hz, 1H, CH₂), 3.78 (s, 3H, CH₃), 1.64 (s, 3H, CH₃).

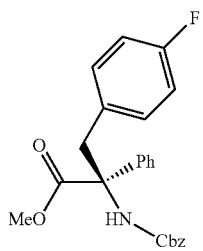 [SMILES: COC(=O)[C@@](Cc1ccc(F)cc1)(NC(=O)OCc1ccccc1)c1ccccc1]

(S)-34 (eluent: c-Hex/Et$_2$O=4/1): $^1$H NMR (400 MHz, CDCl$_3$): 7.47-7.26 (m, 10H, ArH), 6.87-6.82 (m, 4H, ArH), 6.18 (s, 1H, NH), 5.20 (d, J=12.0 Hz, 1H, CH$_2$), 4.95 (d, J=12.4 Hz, 1H, CH$_2$), 3.96 (d, J=13.2 Hz, 1H, CH$_2$), 3.79 (d, J=13.6 Hz, 1H, CH$_2$), 3.69 (s, 3H, CH$_2$). $^{13}$C NMR (100 MHz, CDCl$_3$): 172.5, 162.9 (d), 154.3, 139.9, 136.8, 131.8, 131.6 (d), 128.9, 128.7, 128.6, 128.5, 128.3, 126.1, 115.3 (d), 66.8, 66.3, 53.4, 38.1.

Example 4

Synthesis of (R)-6a: (R)-methyl 2-amino-2-benzyl-3-(4-fluorophenylthio)propanoate To a solution of (R)-5a in dry CH$_2$Cl$_2$ a solution of HBr 30% in acetic acid was added drop wise. The reaction mixture was than stirred at room temperature for 3 h and than quenched with a NaHCO3 saturated solution and extracted with EtOAc.

The same procedure was applied for the synthesis of 6b and 6c starting respectively from 5b and 5c. For the synthesis of 6d the authors followed a different procedure, which is reported below.

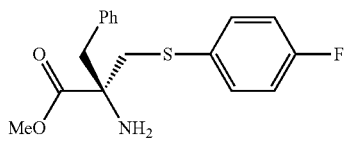 [SMILES: COC(=O)[C@@](N)(CSc1ccc(F)cc1)Cc1ccccc1]

(R)-6a (crystallized from Et$_2$O/pentane): $^1$H NMR (400 MHz, CDCl$_3$): 7.18-7.15 (m, 4H, ArH), 7.09-7.05 (m, 3H, ArH), 6.56 (dt, J$_1$=8.8 Hz, J$_2$=2.0 Hz, 2H, ArH), 3.31 (d, J=12.4 Hz, 1H, CH$_2$), 3.04 (s, 3H, CH$_3$), 2.95 (d, J=12.8 Hz, 1H, CH$_2$), 2.85 (d, J=13.2 Hz, 1H, CH$_2$), 2.64 (d, J=12.8 Hz, 1H, CH$_2$).

$^{13}$C NMR (100 MHz, CDCl$_3$): 167.5 (d), 136.1, 133.5 (d), 131.5, 130.1, 128.5, 128.1, 127.9, 127.8, 127.6, 127.2, 116.9 (d), 62.9, 51.2, 45.8 (d).

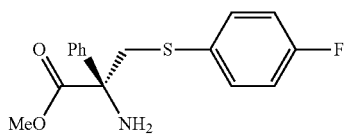

(R)-6b (eluent: c-Hex/Et$_2$O=2/1): $^1$H NMR (400 MHz, C$_6$D$_6$): 7.51-7.49 (m, 2H, ArH), 7.11-6.99 (m, 5H, ArH), 6.56 (t, J=8.8 Hz, 2H, ArH), 3.73 (d, J=13.6 Hz, 1H, CH$_2$), 3.11 (d, J=13.6 Hz, 1H, CH$_2$), 3.11 (s, 3H, CH$_3$), 2.02 (bs, 2H, NH$_2$). $^{13}$C NMR (400 MHz, C$_6$D$_6$): 174.5, 162.8 (d), 142.5, 133.1 (d), 132.2 (d), 128.6, 128.1, 128.0, 127.9, 127.7, 115.9 (d), 65.1, 51.8, 47.3.

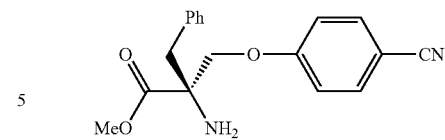

(S)-6c: $^1$H NMR (400 MHz, C$_6$D$_6$): 7.12-7.08 (m, 5H, ArH), 6.90 (d, J=9.2 Hz, 2H, ArH), 6.21 (d, J=9.2 Hz, 2H, ArH), 3.91 (d, J=8.8 Hz, 1H, CH$_2$), 3.53 (d, J=8.4 Hz, 1H, CH$_2$), 3.22 (s, 3H, CH$_3$), 2.94 (d, J=13.2 Hz, 1H, CH$_2$), 2.67 (d, J=12.8 Hz, 1H, CH$_2$), 2.63 (bs, 2H, NH$_2$). $^{13}$C NMR (100 MHz, C$_6$D$_6$): 174.4, 161.3, 135.4, 133.7, 130.2, 128.6, 127.4, 118.8, 115.2, 105.2, 74.0, 62.3, 51.6, 42.4.

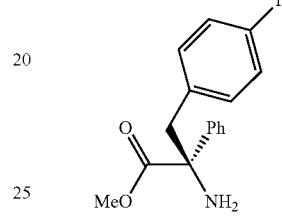

(S)-35 $^1$H NMR (400 MHz, C$_6$D$_6$): 7.50 (d, J=10 Hz, 2H, ArH), 7.10 (d, J=7.2 Hz, 2H, ArH), 6.88-6.86 (m, 2H, ArH), 6.66 (t, J=8.8 Hz, 2H, ArH), 3.41 (d, J=13.6 Hz, 1H, CH$_2$), 3.16 (s, 3H, CH$_3$), 2.95 (d, J=13.6 Hz, 1H, CH$_2$), 1.42 (bs, 2H, NH$_2$).

$^{13}$C NMR (100 MHz, C$_6$D$_6$): 175.1, 163.5, 161.1, 143.6, 132.3 (d), 128.4, 128.1, 127.9, 127.7, 127.6, 125.8, 114.9 (d), 64.6, 51.6, 45.6.

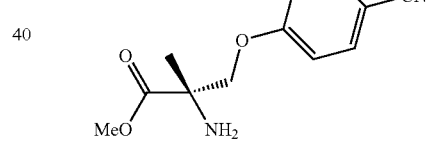

(S)-6d (eluent: CH$_2$Cl$_2$/MeOH=20/1): PhSiH$_3$ (6 eq.) were added to a solution of (R)-5e in CH$_2$Cl$_2$ at room temperature, followed by a catalytic amount of Pd[P(C$_6$H$_5$)$_3$]$_4$. After 2 hrs stirring at this temperature H2O and ethyl acetate were added. The crude mixture was purified by silica column gel chromatography. Isolated yield: 95%.

$^1$H NMR (400 MHz, CDCl$_3$): 6.89 (d, J=8.8 Hz, 2H, ArH), 6.19 (d, J=8.8 Hz, 2H, ArH), 3.70 (d, J=12.0 Hz, 1H, CH$_2$), 3.41 (d, J=8.8 Hz, 1H, CH$_2$), 3.22 (s, 3H, CH$_3$), 1.06 (s, 3H, CH$_3$).

Example 5

Synthesis of (R)-7a: (R)-2-amino-2-benzyl-N-(4-cyano-3-(trifluoromethyl)phenyl)-3-(4-fluorophenylthio)propanamide Lithium bis(trimethylsilyl)amide (LHMDS) (0.5 eq.) was added to a solution of 4-cyano-3-trifluoromethyl aniline (1.6 eq.) in dry THF (1 mL per mmol aniline) at 0° C. After stirring for 45 min. hexamethylphosphoric triamide (HMPA) (20% of the previously added). After 5 min at 0° C. a solution of (R)-6a in THF (1.5 mL per 0.1 mmol fo 6a) was added drop wise. After 30 min at 0° C., the reaction mixture was allowed to warm up at temperature value and than stirred for additional 3 h. The reaction was than quenched with a NH₄Cl saturated solution and extracted with ethyl acetate.

The same procedure was applied for the synthesis of 7b and 36 starting respectively from 6b and 35. For the synthesis of 7c and 7d, starting from 6c and 6d the same procedure was applied except for the ester addition which must be performed at −40° C. and warmed up to −20° C. in 2 h.

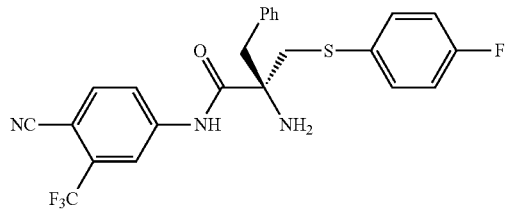 [SMILES: N#Cc1ccc(NC(=O)[C@@](N)(CSc2ccc(F)cc2)Cc2ccccc2)cc1C(F)(F)F]

(R)-7a: ¹H NMR (400 MHz, C₆D₆): 9.94 (s, 1H, NH), 7.80 (d, J=1.2 Hz, 1H, ArH), 7.71-7.70 (m, 2H, ArH), 7.39-7.35 (m, 2H, ArH), 7.28-7.25 (m, 3H, ArH), 7.13-7.11 (m, 2H, ArH), 6.89 (t, J=8.8 Hz, 2H, ArH), 3.80 (d, J=13.2 Hz, 1H, CH₂), 3.33 (d, J=13.2 Hz, 1H, CH₂), 3.05 (d, J=13.2 Hz, 1H, CH₂), 2.82 (d, J=13.6 Hz, 1H, CH₂).

¹³C NMR (400 MHz, C₆D₆): 172.9, 162.5 (d), 141.1, 135.4 (d), 133.4 (d), 130.1, 128.8, 128.1, 127.9, 127.6, 12.2, 116.3 (q), 104.6, 62.1, 46.2, 45.3.

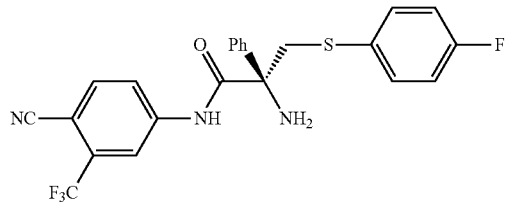 [SMILES: N#Cc1ccc(NC(=O)[C@@](N)(CSc2ccc(F)cc2)c2ccccc2)cc1C(F)(F)F]

(R)-7b (eluent: c-Hex/EtOAc=2/1): ¹H NMR (400 MHz, C₆D₆): 9.38 (s, 1H, NH), 7.41 (s, 1H, ArH), 7.31-7.28 (m, 2H, ArH), 7.12-6.95 (m, 6H, ArH), 6.75 (d, J=8.4 Hz, 1H, ArH), 6.55 (t, J=8.4 Hz, 1H, ArH), 3.98 (d, J=13.2 Hz, 1H, CH₂), 2.98 (d, J=13.2 Hz, 1H, CH₂), 1.70 (bs, 2H, NH₂).

¹³C NMR (400 MHz, C₆D₆): 171.5, 162.6 (d), 141.4, 140.7, 135.4, 133.6 (d), 130.8, 128.8, 128.4, 128.2, 127.9, 127.6, 125.3, 121.1, 116.3, (t), 115.5, 104.4, 64.2, 47.7.

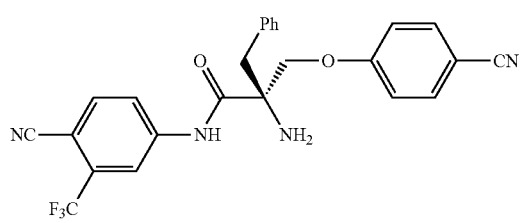 [SMILES: N#Cc1ccc(OC[C@@](N)(Cc2ccccc2)C(=O)Nc2ccc(C#N)c(C(F)(F)F)c2)cc1]

(S)-7c: ¹H NMR (400 MHz, C₆D₆): 9.41 (s, 1H, NH), 7.47 (s, 1H, ArH), 7.24 (d, J=8.4 Hz, 1H, ArH), 7.01-6.90 (m, 7H, ArH), 6.79 (d, J=8.4 Hz, 1H, ArH), 6.30 (d, J=8.4 Hz, 1H, ArH), 4.16 (d, J=8.4 Hz, 1H, CH₂), 3.22 (d, J=6.8 Hz, 1H, CH₂), 2.99 (d, J=13.2 Hz, 1H, CH₂), 2.39 (d, J=13.2 Hz, 1H, CH₂), 1.25 (bs, 2H, NH₂). ¹³C NMR (400 MHz, C₆D₆): 172.3, 161.0, 141.2, 135.6, 134.7, 133.9, 130.1, 128.9, 127.8, 121.2, 118.6, 116.6, 115.4, 115.1, 105.6, 73.3, 61.8, 42.1.

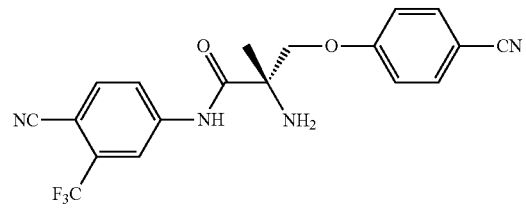 [SMILES: C[C@](N)(COc1ccc(C#N)cc1)C(=O)Nc1ccc(C#N)c(C(F)(F)F)c1]

(S)-7d (eluent: Et₂O/EtOAc=2/1): ¹H NMR (400 MHz, C₆D₆): 9.63 (s, 1H, NH), 7.47 (s, 1H, ArH), 7.35 (dd, 1H, J₁=8.8 Hz, J₂=2.0 Hz, 1H, ArH), 6.91 (dd, 1H, J₁=6.8 Hz, J₂=2.8 Hz, 2H, ArH), 6.79 (d, J=8.4 Hz, 1H, ArH), 6.21 (d, J=8.4 Hz, 1H, ArH), 4.08 (d, J=8.4 Hz, 1H, ArH), 2.93 (d, J=8.8 Hz, 1H, ArH), 0.89 (s, 3H, CH₃).

¹³C NMR (400 MHz, C₆D₆): 172.9, 160.9, 141.4, 135.7, 133.8, 121.0, 118.6, 116.5, 116.4, 115.0, 73.7, 57.7, 23.1.

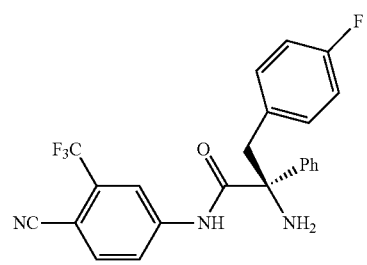 [SMILES: N#Cc1ccc(NC(=O)[C@](N)(Cc2ccc(F)cc2)c2ccccc2)cc1C(F)(F)F]

(S)-36 ¹H NMR (400 MHz, C₆D₆): 9.35 (s, 1H, NH), 7.47-7.39 (m, 3H, ArH), 7.17-7.02 (m, 5H, ArH), 6.79-6.65 (m, 4H, ArH), 3.79 (d, J=13.6 Hz, 1H, CH₂), 2.66 (d, J=13.2 Hz, 1H, CH₂), 1.16 (bs, 2H, NH₂).

¹³C NMR (100 MHz, C₆D₆): 172.6, 162.7 (d), 142.0, 141.6, 135.5, 132.3 (d), 131.9, 128.8, 128.1, 127.9, 127.6, 125.4, 121.1, 116.4 (d), 115.d (d), 64.3, 45.1.

Example 6

Synthesis of (R)-8: (R)-2-amino-2-benzyl-N-(4-cyano-3-(trifluoromethyl)phenyl)-3-(4-fluorophenylsulfonyl)propanamide A solution of m-Chloro per-benzoic acid (MCPBA) in CH₂Cl₂ (3.5 eq) was added drop wise to a solution of (R)-7a in CH₂Cl₂ at 5° C. The reaction mixture was stirred at this temperature for 1 h and than at room value for additional 2 hrs. The reaction was than quenched with a saturated solution of NaHCO₃ and extracted with ethyl acetate. The pure compound was obtained after column chromatography purification and crystallization from ethyl ether/pentane. Isolated yield: 70%.

The same procedure was applied for the synthesis of (R)-9[(S)-9].

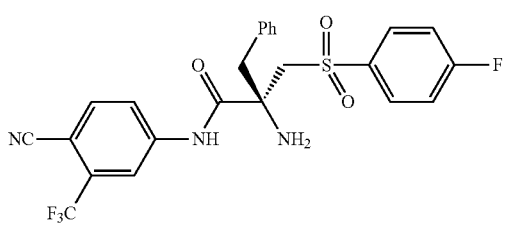 [SMILES: N#Cc1ccc(NC(=O)[C@](N)(Cc2ccccc2)CS(=O)(=O)c2ccc(F)cc2)cc1C(F)(F)F]

(R)-8[(S)-8] (eluent: c-Hex/EtOAc=1/1): $^1$H NMR (400 MHz, C$_6$D$_6$): 9.38 (s, 1H, NH), 7.54 (d, J=2.4 Hz, 1H, ArH), 7.51-7.47 (m, 2H, ArH), 6.92-6.87 (m, 4H, ArH), 6.80-6.73 (m, 3H, ArH), 6.36 (t, J=8.4 Hz, 2H, ArH), 3.84 (d, J=14.0 Hz, 1H, CH$_2$), 2.77 (dd, J$_1$=13.2 Hz, J$_2$=2.4 Hz, 2H, CH$_2$), 2.22 (d, J=13.6 Hz, 1H, CH$_2$), 2.04 (bs, 2H, NH$_2$). $^{13}$C NMR (400 MHz, C$_6$D$_6$): 171.8, 167.9, 164.5, 141.0, 136.5, 135.4, 133.9, 130.8 (d), 130.1, 128.8, 128.1, 127.9, 127.8, 127.6, 121.4, 116.2 (q), 104.8, 63.0, 60.4, 46.6. $[\alpha]^{20}_D$-144 (c 0.4, CH$_3$OH).

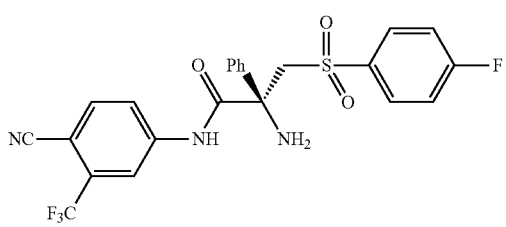 [SMILES: N#Cc1ccc(NC(=O)[C@@](N)(CS(=O)(=O)c2ccc(F)cc2)c2ccccc2)cc1C(F)(F)F]

(R)-9[(S)-9] (eluent: c-Hex/EtOAc=1/1): $^1$H NMR (400 MHz, C$_6$D$_6$): 9.39 (s, 1H, NH), 7.54-7.51 (m, 3H, ArH), 7.07-7.05 (m, 2H, ArH), 6.99-6.90 (m, 4H, ArH), 6.76 (d, J=8.4 Hz, 1H, ArH), 6.41 (t, J=9.2 Hz, 2H, ArH), 4.27 (d, J=14.4 Hz, 1H, CH$_2$), 3.20 (d, J=14.4 Hz, 1H, CH$_2$), 2.36 (bs, 2H, NH$_2$). $^{13}$C NMR (100 MHz, C$_6$D$_6$): 170.7, 166.0 (d), 141.2, 139.8, 136.9, 135.4, 130.8 (d), 128.9, 128.5, 128.1, 127.9, 127.6, 125.0, 121.3, 116.3 (q), 104.7, 64.4, 62.5. $[\alpha]^{20}_D$+85 (c 0.4, CH$_3$OH).

Example 7

Synthesis of (S)-13: (R)-4-(4-((4-fluorophenylsulfonyl)methyl)-5-oxo-4-phenyl-2-thioxoimidazolidin-1-yl)-2-(trifluoromethyl)benzonitrile To a solution of (S)/(R)-9 in dry toluene and an excess of di-isopropyl ethylamine (DIPEA), 2 eq. of dipyridyl-thionocarbonate (DPTC) were added in one portion at 100° C. After 3 h stirring the reaction mixture was quenched with 0.1 N HCl and extracted with ethyl acetate. The crude compound was purified by silica gel column chromatography. Isolated yield 90%.

The same synthetic procedure was applied to the synthesis of compounds 11 and 37 starting respectively from 8 and 36.

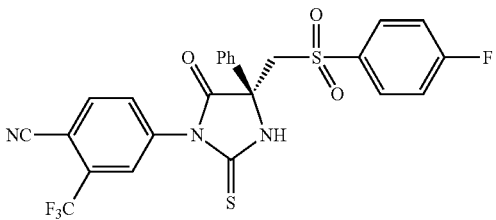 [SMILES: N#Cc1ccc(N2C(=O)[C@@](CS(=O)(=O)c3ccc(F)cc3)(c3ccccc3)NC2=S)cc1C(F)(F)F]

(R)-13: $^1$H NMR (400 MHz, Aceton): 8.31 (d, J=7.6 Hz, 1H, ArH), 8.13 (d, J=2.0 Hz, 1H, ArH), 8.01-8.04 (m, 3H, ArH), 7.62 (dd, J1=8.4 Hz, J2=2.0 Hz, 2H, ArH), 7.45-7.39 (m, 5H, ArH), 4.59 (d, 1H, J=15.6 Hz, CH$_2$), 4.43 (d, 1H, J=15.2 Hz, CH$_2$), 2.98 (bs, 1H, NH).
$^{13}$C NMR (100 MHz, Aceton): 181.7, 172.3, 167.5, 164.9, 138.2, 136.8, 136.3, 135.6, 133.3, 131.6 (d), 129.6, 129.4, 127.6)d), 125.7, 116.7 (d), 114.9, 110.0, 66.4, 61.3.

(S)-37: $^1$H NMR (400 MHz, Aceton): 10.3 (s, 1H, NH)), 8.16 (d, J=8.0 Hz, 1H, ArH), 7.79 (m, 2H, ArH), 7.54-7.38 (m, 7H, ArH), 7.16-7.12 (m, 2H, ArH), 3.79 (d, 1H, J=13.6 Hz, CH$_2$), 3.49 (d, 1H, J=13.6 Hz, CH$_2$). $^{13}$C NMR (100 MHz, Aceton): 180.8, 173.1, 162.3 (d), 137.6, 137.0, 136.1, 133.2, 132.7 (d), 130.3 (d), 129.2, 129.0, 127.2, (q), 126.2, 123.8, 121.1, 115.5, 1125.3, 114.8, 109.7, 71.4, 44.1.

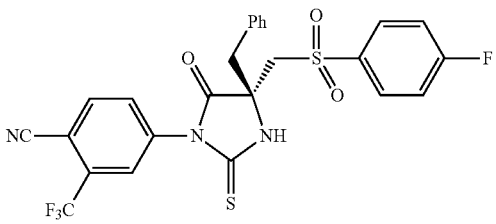 [SMILES: N#Cc1ccc(N2C(=O)[C@](Cc3ccccc3)(CS(=O)(=O)c3ccc(F)cc3)NC2=S)cc1C(F)(F)F]

(R)-11: $^1$H NMR (400 MHz, CDCl$_3$): 8.12 (s, 1H, NH), 8.02-7.98 (m, 2H, ArH), 7.83 (d, J=8.4 Hz, 1H, ArH), 7.38-7.26 (m, 6H, ArH), 7.19 (d, J=6.8 Hz, 1H, ArH), 7.08 (s, 1H, ArH), 3.87 (q, J=7.2 Hz, 2H, CH$_2$), 3.37 (d, J=13.6 Hz, 1H, CH$_2$), 3.19 (d, J=13.6 Hz, 1H, CH$_2$). $^{13}$C NMR (100 MHz, CDCl$_3$): 180.9, 172.1, 166.4 (d), 136.5, 135.6, 135.5, 132.3, 131.5, 131.3 (d), 130.6, 129.2, 128.9, 127.1, 117.4 (d), 114.9, 110.8, 66.3, 60.3, 43.3.

Example 8

Synthesis of (R)-10: (R)-2-benzyl-N-(4-cyano-3-(trifluoromethyl)phenyl)-3-(4-fluorophenylsulfonyl)-2-(methylsulfonamido)propanamide MethanSulfonyl chloride (10 eq.) was added to a solution of (R)-8 in pyridine a room temperature. The reaction mixture was than stirred at 50° C. for 5 h and than quenched with 0.1N HCl and extracted with ethyl acetate. The compound was obtained pure in 98% yield.

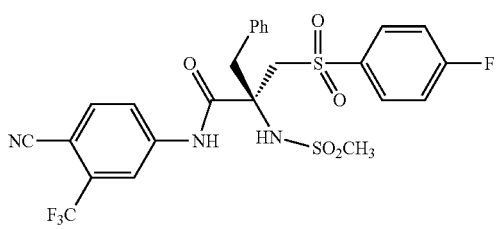 [SMILES: CS(=O)(=O)N[C@@](Cc1ccccc1)(CS(=O)(=O)c1ccc(F)cc1)C(=O)Nc1ccc(C#N)c(C(F)(F)F)c1]

(R)-10 $^1$H NMR (400 MHz, C$_6$D$_6$): 8.92 (s, 1H, NH), 7.81 (s, 1H, ArH), 7.43-7.56 (m, 2H, ArH), 7.38 (d, J=8.2 Hz, 1H, ArH), 7.13 (s, 1H, ArH), 7.03-6.81 (m, 3H, ArH), 7.82 (d, J=9.2 Hz, 1H, ArH), 6.38 (t, J=8.4 Hz, 2H, ArH), 6.18 (bs, 1H, HN), 3.97 (d, J=15.2 Hz, 1H, CH$_2$), 3.77 (d, J=15.2 Hz, 1H, CH$_2$), 3.63 (d, J=13.6 Hz, 1H, CH$_2$), 3.55 (d, J=13.6 Hz, 1H, CH$_2$), 2.82 (s, 3H, CH$_3$).

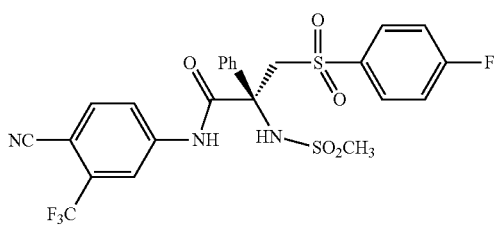 [SMILES: CS(=O)(=O)N[C@@](CS(=O)(=O)c1ccc(F)cc1)(C(=O)Nc1ccc(C#N)c(C(F)(F)F)c1)c1ccccc1]

(R)-12 $^1$H NMR (400 MHz, CDCl$_3$): 8.89 (s, 1H, NH), 7.98 (s, 1H, ArH), 7.45-7.53 (m, 2H, ArH), 7.36 (d, J=8.2 Hz, 1H, ArH), 7.13-7.15 (m, 1H, ArH), 7.01-6.82 (m, 4H, ArH), 6.38 (t, J=8.4 Hz, 2H, ArH), 3.97 (d, J=15.2 Hz, 1H, CH$_2$), 3.77 (d, J=15.2 Hz, 1H, CH$_2$), 3.63 (d, J=13.6 Hz, 1H, CH$_2$), 3.55 (d, J=13.6 Hz, 1H, CH$_2$), 2.82 (s, 3H, CH$_3$).

Example 9

Synthesis of (S) [or (R)]-20: (S)-2-(tert-butylsulfinylimino)-N-(4-cyano-3-(trifluoromethyl)phenyl) propanamide A solution of 2-methylpropane-2-sulfinamide (S or R) (1 eq.), Ti(OEt)$_4$ (3 eq.) and dry THF (4 mL per mmol), was added drop wise to a solution of 19 (2.5 eq.) (obtained according to *J. Med. Chem.* 2007, 50(5), 1028-1040 and Synthesis 2002, 7, 850-852) in THF (4 mL per mmol) at 40° C. The reaction mixture was stirred at this temperature for 30 min, than solvent was removed under vacuum and the crude material was purified by silica gel column chromatography (eluent: c-Hex/EtOAc=11/9). Isolated yield: 56%.

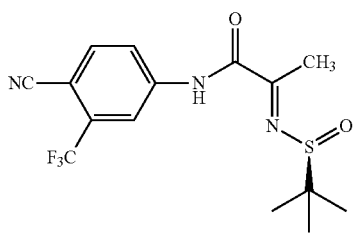 [SMILES: C/C(=N\[S@@](=O)C(C)(C)C)C(=O)Nc1ccc(C#N)c(C(F)(F)F)c1]

(S)-20 $^1$H NMR (400 MHz, CDCl$_3$): 9.24 (bs, 1H), 8.06 (s, 1H), 7.92-7.98 (m, 1H), 7.80-7.84 (m, 1H), 2.65 (s, 3H) 1.36 (s, 9H).

$^{13}$C NMR (100 MHz, CDCl$_3$): 171.1, 160.3, 141.0, 136.2, 134.3 (q, J=35 Hz), 122.2, 123.3 (q), 117.5 (q, J=5 Hz), 115.5, 105.5, 59.6, 23.1, 16.8.

Example 10

Synthesis of (S,S)- [or (R,R)]-21: (R)—N-(4-cyano-3-(trifluoromethyl)phenyl)-2-((R)-1,1-dimethylethylsulfinamido)-3-(4-fluorophenylsulfonyl)-2-methylpropanamide n-BuLi (3 eq.; 2.5 M in haxane) was added drop wise to a solution of fluoro-4-(methylsulfonyl)benzene (3.2 eq.) in dry THF (4 mL×mmol) at room temperature. the reaction mixture was than stirred for 1 h and than cooled at −45° C. Afterwards, a solution of (S) [or (R)]-20 (1 eq.) in THF (2 mL×mmol) was added drop wise. The mixture was than stirred at −20° C. for 1 h and than quenched with 0.1N HCl and extracted with diethyl ether. The crude compound was isolated by silica gel column chromatography. Isolated yield: 68%.

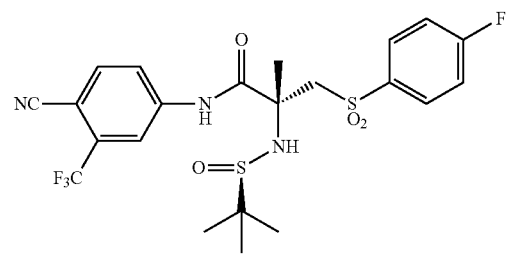 [SMILES: CC(C)(C)[S@@](=O)N[C@@](C)(CS(=O)(=O)c1ccc(F)cc1)C(=O)Nc1ccc(C#N)c(C(F)(F)F)c1]

(R,R)-21 $^1$H NMR (400 MHz, CDCl$_3$): 9.05 (bs, 1H), 7.98 (s, 1H), 7.90-7.96 (m, 2H), 7.79-7.82 (m, 2H), 7.19-7.26 (m, 2H), 6.02 (s, 1H), 4.06 (d, J=14 Hz, 1H), 3.73 (d, J=14 Hz, 1H), 1.84 (s, 3H) 1.45 (s, 9H). $^{13}$C NMR (100 MHz, CDCl$_3$): 170.9, 166.4 (d, J=257 Hz), 141.2, 136.2, 134.7 (q, J=36 Hz) 131.1 (d, J=13.8 Hz), 122.3 (q), 122.3, 117.6 (q, J=5 Hz), 117.0 (d, J=22.9 Hz), 115.5, 105.5, 63.1, 62.7, 56.9, 24.8, 23.2. [α]$^{20}_D$+13.0 (c 0.4, CH$_3$OH); MP: 96-98° C.

Example 11

Synthesis of (S)- [or (R)]-23: (R)-2-amino-N-(4-cyano-3-(trifluoromethyl)phenyl)-3-(4-fluorophenylsulfonyl)-2-methyl propanamide HCl (2M in Et$_2$O, 16 eq.) was added drop wise to a solution of (R,R)-21 (1 eq.) in dry MeOH (5 mL×mmol) cooled at −5° C. The reaction mixture was than stirred at room temperature for 3 h. The solvent was than removed under vacuum and the crude material was than washed with a saturated solution of NaHCO3 and extracted with EtOAc. The pure compound was obtained by crystallization from ethyl ether/pentane. Isolated yield: 93%.

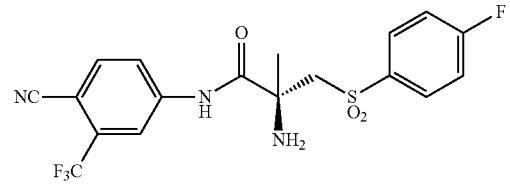 [SMILES: C[C@](N)(CS(=O)(=O)c1ccc(F)cc1)C(=O)Nc1ccc(C#N)c(C(F)(F)F)c1]

Example 12

Synthesis of (R)-22: (R)—N-(4-cyano-3-(trifluoromethyl)phenyl)-2-(1,1-dimethylethylsulfonamido)-3-(4-fluorophenyl sulfonyl)-2-methylpropanamide m-chloro perbenzoic acid (1.3 eq.) was added to a solution of (R,R)-21 (1 eq.) in dry $CH_2Cl_2$ (35 mL×mmol). The reaction mixture was stirred at room temperature for 2 h. EtOAc was than added to the solution and the organic layer was than washed with a saturated solution of $Na_2S_2O_3$ followed by a saturated solution of $Na_2CO_3$. The crude material was purified by silice gel column chromatography. Isolated yield: 91%.

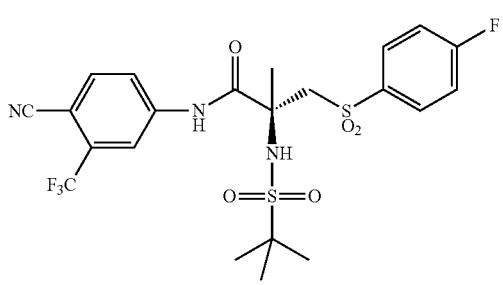 [SMILES: CC(C)(C)S(=O)(=O)N[C@@](C)(CS(=O)(=O)c1ccc(F)cc1)C(=O)Nc1ccc(C#N)c(C(F)(F)F)c1]

(R)-22 $^1$H NMR (400 MHz, $CDCl_3$): 9.50 (bs, 1H, NH), 7.99 (d, J=1.2 Hz, 1H, ArH), 7.93-7.89 (m, 2H, ArH), 7.80-7.73 (m, 2H, ArH), 7.21-7.17 (m, 2H, ArH), 6.26 (bs, 1H, NH), 4.04 (d, J=14.4 Hz, 1H, $CH_2$), 3.50 (d, J=14.4 Hz, 1H, $CH_2$), 1.90 (s, 3H, $CH_3$), 1.57 (s, 9H, $^tBu$). $^{13}$C NMR (100 MHz, $CDCl_3$): 169.9, 141.4, 135.7, 131.0, 130.9, 122.1, 117.5, 117.4, 117.0, 116.8, 115.4, 63.4, 63.1, 61.2, 24.5, 24.1.

Example 13

Synthesis of (R)-28: (R)-4-(4-((4-fluorophenylsulfonyl)methyl)-4-methyl-2,5-dioxoimidazolidin-1-yl)-2-(trifluoro methyl)benzonitrile To a solution of (S)/(R)-23 in dry toluene and an excess of di-isopropyl ethylamine (DIPEA), 6 eq. of carbonyldiimidazole (CDI) were added in one portion at room temperature and than brought to 100° C. After 12 h stirring the reaction mixture was quenched with 0.1 N HCl and extracted with ethyl acetate. The crude compound was purified by silica gel column chromatography. Isolated yield 90%.

The same procedure was followed for the synthesis of (S)-14d and (S)-14e.

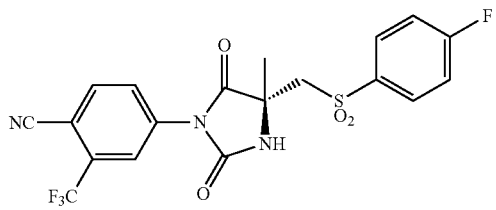 [SMILES: C[C@@]1(CS(=O)(=O)c2ccc(F)cc2)NC(=O)N(c2ccc(C#N)c(C(F)(F)F)c2)C1=O]

(R)-28 $^1$H NMR (400 MHz, $CDCl_3$): 8.06 (s, 1H), 7.90-8.0 (m, 4H), 7.22-7.32 (m, 2H), 6.91 (bs, 1H), 3.70 (d, J=16.4 Hz, 1H), 3.66 (d, J=16.4 Hz, 1H), 1.72 (s, 3H). $^{13}$C NMR (100 MHz, $CDCl_3$): 172.7, 166.5 (d, J=257 Hz), 153.4, 136.1, 135.7, 134.6 (q, J=36 Hz) 131.1 (d, J=9.8 Hz), 128.9, 123.9 (q, J=4.6 Hz), 122.4 (q), 117.3 (d, J=22.6 Hz), 115.1, 109.3, 61.5, 59.3, 24.8. $[\alpha]^{20}_D$+11.0 (c 0.4, Acetone); IR($CDCl_3$, $cm^{-1}$) 3360, 2960, 2928, 2240, 1733, 1731, 1402. MS m/z (E.I.) 455 (M+), 434, 282, 254, 213.

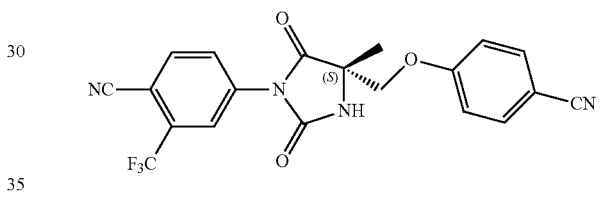

(S)-14d $^1$H NMR (400 MHz, $CDCl_3$): 8.09 (s, 1H, ArH), 7.96-7.93 (m, 2H, ArH), 7.58 (d, J=9.2 Hz, 2H, ArH), 6.91 (d, J=9.2 Hz, 2H, ArH), 4.33 (d, J=9.6 Hz, 1H, $CH_2$), 4.14 (d, J=9.2 Hz, 1H, $CH_2$), 1.68 (s, 3H, $CH_3$). $^{13}$C NMR (100 MHz, $CDCl_3$): 172.5, 160.8. 153.9, 136.1, 165.7, 134.5, 128.3, 123.4, 118.8, 115.6, 115.0, 109.1, 106.0, 71.2, 61.9, 20.5.

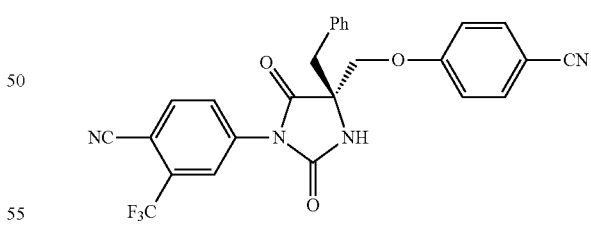

(S)-14e $^1$H NMR (400 MHz, Aceton): 8.22 (s, 1H, NH), 8.14 (d, J=8.0 Hz, 1H, ArH), 7.75-7.15 (m, 4H, ArH), 7.33-7.30 (m, 5H, ArH), 7.21 (d, J=9.2 Hz, 2H, ArH), 4.70 (d, J=10.0 Hz, 1H, $CH_2$), 4.56 (d, J=9.6 Hz, 1H, $CH_2$), 3.40 (AB system, $J_1$=13.6 Hz, $J_2$=5.2 Hz, 2H, $CH_2$). $^{13}$C NMR (100 MHz, Aceton): 172.1, 161.8, 153.6, 136.7, 136.2, 134.3, 133.8, 130.6, 129.4, 128.6, 127.7, 123.9 (q, $CF_3$), 123.4 (q), 18.7, 116.0, 115.0, 108.2, 105.170.5, 66.5, 39.0.

For the synthesis of (R)-27 the authors followed the same procedure reported for example 7.

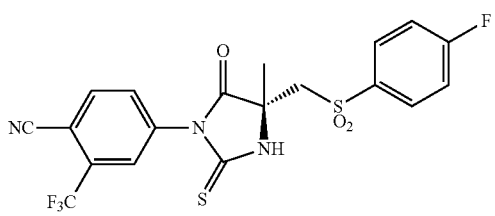

(R)-27 $^1$H NMR (400 MHz, CDCl$_3$): 8.08-7.80 (m, 6H), 7.22-7.34 (m, 2H), 3.74 (d, J=14.8 Hz, 1H), 3.67 (d, J=14.8 Hz, 1H), 1.74 (s, 3H). $^{13}$C NMR (100 MHz, CDCl$_3$): 180.8, 173.3, 167.5, (d, J=257 Hz), 136.9, 135.7, 134.6 (q, J=36 Hz), 132.4, 131.2 (d, J=9.3 Hz), 127.2, 123.4, 122.8 (q), 117.4 (d, J=22.5 Hz), 115.0, 110.9, 61.7, 61.3, 24.3. IR (CDCl$_3$, cm$^{-1}$) 1731, 1591, 1462, 1377. MS m/z (E.I.) 471 (M+), 442, 380, 346, 282, 213.

Example 14

Synthesis of (R)-24: (R)-1-(4-cyano-3-(trifluoromethyl)phenylamino)-3-(4-fluorophenylsulfonyl)-2-methyl-1-oxopropan-2-aminium chloride 4 eq. of 0.2N HCl in Et$_2$O were added drop wise to a solution of (R)-22 dissolved in dry MeOH and cooled at 5° C. The reaction mixture was stirred at room temperature for 3 h and the solvent removed under vacuum. The compound was crystallized from CH$_3$CN/Et$_2$O and the yield was quantitative.

$^1$H NMR (400 MHz, d$^6$-DMSO): 12-11.4 (bs, 1H), 8.95-8.40 (bs, 3H, NH3$^+$), 8.19 (s, 1H), 8.16-8.0 (m, 2H), 7.85 (bs, 2H), 7.22-7.16 (m, 2H), 5.36 (d, J=15.6 Hz, 1H), 4.05 (d, J=15.6 Hz, 1H), 1.75 (s, 3H). $^{13}$C NMR (100 MHz, d$^6$-DMSO): 167.6 163.8 (d, J=257 Hz), 143.0, 136.8, 135.0, 131.2 (d, J=9.4 Hz), 123.4, 117.8, 117.2 (d, J=23.4 Hz), 116.3, 103.3, 100.4, 58.5, 23.9.

Example 15

Synthesis of (R/S)-29: 4-((4-fluorophenylsulfonyl)methyl)-4-methyl-3-(methylsulfonyl)-2,5-dioxoimidazolidin-1-yl)-2-(trifluoromethyl)benzonitrile To a solution of (R)-28 in dry CH$_2$Cl$_2$, methanesulfonyl chloride (3 eq.), triethylmine (6 eq.) and dimethyl amino pyridine (1 eq.) were successively added at room temperature. The reaction mixture was stirred for 5 h and tan quenched with 0.1 N HCl and extracted with ethyl acetate. The compound was purified by silica gel column chromatography. Isolated yield: 90%.

The same procedure was applied for the synthesis of (R/S)-30, while for the synthesis of (R/S)-31 and (R/S)-32 di-isopropylamine was used instead of trietylamine.

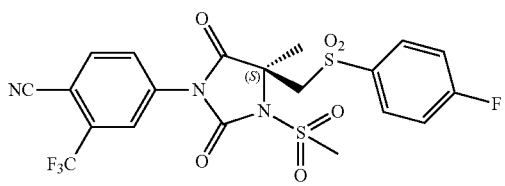

(S)-29 $^1$H NMR (400 MHz, CDCl$_3$): 8.07 (s, 1H, ArH), 8.02-7.82 (m, 4H, ArH), 7.30 (t, J=8.0 Hz, 2H, ArH), 4.25 (d, J=14.4 Hz, 1H, CH$_2$), 3.77 (s, 3H, CH$_3$), 3.76 (d, J=14.0 Hz, 1H, CH$_2$), 1.94 (s, 3H, CH$_3$). $^{13}$C NMR (100 MHz, CDCl$_3$): 170.8, 151.2, 13.9, 135.3, 135.0, 131.1 (d), 129.8, 124.7, 117.4 (d), 114.8, 64.8, 59.8, 43.5, 31.1, 25.1.

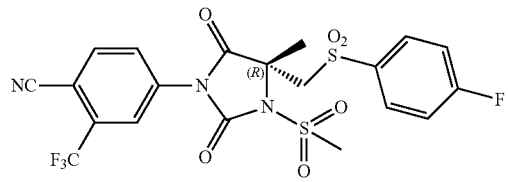

(R)-30 $^1$H NMR (400 MHz, CDCl$_3$): 8.03 (d, J=10.2 Hz, 1H, ArH), 7.96-7.92 (m, 3H, ArH), 7.83 (d, J=10.0 Hz, 1H, ArH), 7.29 (t, J=8.0 Hz, 2H, ArH), 4.35 (d, J=14.4 Hz, 1H, CH$_2$), 4.00 (s, 3H, CH$_3$), 3.76 (d, J=14.4 Hz, 1H, CH$_2$), 1.98 (s, 3H, CH$_3$). $^{13}$C NMR (100 MHz, CDCl$_3$): 178-8, 171.9, 167.9, 165.4, 136.6, 136.0, 135.2 (d), 134-6, 131.1 (d), 127.8 (q), 123.3, 117.4 (d), 114.8, 111.7, 67.5, 60.5, 44.6, 25.6.

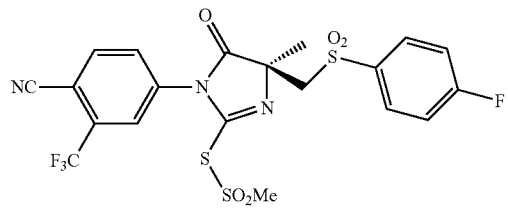 [SMILES: C[C@]1(CS(=O)(=O)c2ccc(F)cc2)N=C(SS(C)(=O)=O)N(c2ccc(C#N)c(C(F)(F)F)c2)C1=O]

(S)-31 $^1$H NMR (400 MHz, CDCl$_3$): 7.95-7.91 (m, 3H, ArH), 7.77-7.68 (m, 4H, ArH), 7.32-7.26 (m, 4H, ArH), 3.99 (d, J=14.4 Hz, 1H, CH$_2$), 3.77 (d, J=14.4 Hz, 1H, CH$_2$), 2.43 (s, 3H, CH$_3$), 1.84 (s, 3H, CH$_3$). $^{13}$C NMR (100 MHz, CDCl$_3$): 174.6, 167.8, 165.2, 164.9, 144.9, 1379, 136.8, 135.9 (d), 132.2, 131.4 (d), 130.0, 127.0 (d), 117.3 (d), 114.8, 111.3, 64.0, 51.9, 28.1, 21.9.

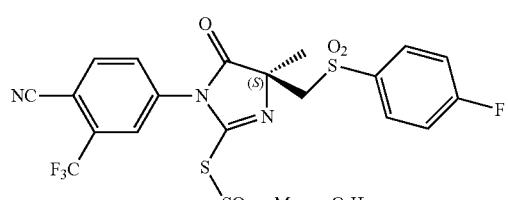

(S)-32 $^1$H NMR (400 MHz, CDCl$_3$): 8.02 (d, J=8.4 Hz, 1H, ArH), 7.96-7.92 (m, 2H, ArH), 7.85 (s, 1H, ArH), 7.81 (d, J=8.2 Hz, 1H, ArH), 4.00 (d, J=15.2 Hz, 1H, CH$_2$), 3.77 (d, J=15.2 Hz, 1H, CH$_2$), 3.05 (s, 3H, CH$_3$), 1.84 (s, 3H, CH$_3$). $^{13}$C NMR (100 MHz, CDCl$_3$): 174.6, 167.8, 165.8, 165.3, 137.9, 136.2, 135.7 (d), 134.6, 132.5, 131.4 (d), 127.0 (d), 123.3, 120.6, 117.3 (d), 114.7, 111.7, 63.9, 52.3, 41.9, 27.9.

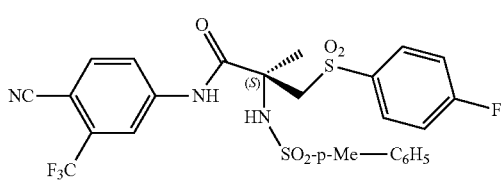

(S)-26 For the synthesis of (S)-26 the authors started from (S)-23 and followed the same procedure reported for the example 8.

$^1$H NMR (400 MHz, CDCl$_3$): 9.33 (s, 1H, NH), 7.90-7.84 (m, 4H, ArH), 7.59-7.51 (m, 2H, ArH), 7.37 (d, J=8.0 Hz, 2H, ArH), 7.16-7.09 (m, 3H, ArH), 3.96 (d, J=14.4 Hz, 1H, CH$_2$), 3.96 (d, J=14.8 Hz, 1H, CH$_2$), 2.46 (s, 3H, CH$_3$), 1.59 (s, 3H, CH$_3$). $^{13}$C NMR (100 MHz, CDCl$_3$): 169.6, 167.5, 164.9, 144.9 141.2, 138.0, 135.6, 135.2, 135.1, 134.0, 133.7, 131.0 (d), 130.2, 127.2, 122.4, 117.7 (d), 116.7 (d), 115.2, 105.162.0, 61.5, 23.2, 21.6.

Example 16

Drug Library Screening was Performed on LNCaP Cells, a Human Prostate Hormone Sensible Tumour Cell Line Furthermore, the compounds with the highest anti-tumour activity, were tested on LNCaP-AR line, derived from LNCaP, with hormone refractory prostate cancer (HRPC) features.

Cell Lines

Evaluation of the cytotoxic effect of novel antiandrogens to select the most active compounds was performed in different in vitro human prostate cancer models: LNCaP cells, derived from a prostatic cancer lymph node lesion responsive to the antiandrogen treatment, obtained from the American Type Culture Collection (ATCC); LNCaP-AR line, derived from LNCaP with HRPC features, engineered to stably-express high levels of AR (a generous gift of Dr. Sawyers of the Memorial Sloan Kettering Institute, NY); PC3 and DU145, two hormone-refractory prostate cancer cell lines non expressing AR receptor, purchased from ATCC. Finally, compounds were also tested on HepG2 cells, originally isolated from a primary hepatoblastoma of an 11-year-old boy, purchased from ATCC.

The cell lines were maintained as a monolayer at 37° C. and subcultured weekly. Culture medium was composed of RPMI 1640 supplemented with 10% fetal calf serum and 1% glutamine (Mascia Brunelli s.p.a., Milan, Italy). Cells were used in the exponential growth phase in all the experiments.

Compounds (R)-Bicalutamide and compounds (R,S)-23, (R,S)-28, (R,S)-27, (R,S)-22, (R,S)-26, (R)-24, (R,S)-29, (R,S)-30, (R,S)-8, (R,S)-9, (R,S)-31, (S)-32, (R)-11, (S)-36, (S)-37, (R)-10, (R)-13, (S)-7d, (S)-14d were tested. Compounds were dissolved in acetone or DMSO (AITES) (10 µM) and stored at −20° C. The cell culture containing acetone at the highest concentration was used as the control.

R1881 is a commercially available synthetic radiolabeled androgen methyltrienolone-17β-hydroxy-17-methyl-estra-4, 9.11-trien-3-one, native ligand of the androgen receptor.

In Vitro Chemosensitivity Assay

Sulforhodamine B (SRB) assay was used according to the method by Skehan et al. (JNCI, 1990). Briefly, cells were collected by trypsinization, counted and plated at a density of 5,000 cells/well in 96-well flat-bottomed microtiter plates (100 µl of cell suspension/well). In the chemosensitivity assay, experiments were run in octuplicate, and each experiment was repeated three times. The optical density (OD) of cells was determined at a wavelength of 490 nm by a colorimetric plate reader.

Data Analysis

Growth inhibition and cytocidal effect of drugs were calculated according to the formula reported by Monks et al. (JNCI, 1991):

$$[(OD_{treated}-OD_{zero})/(OD_{control}-OD_{zero})]\times 100\%,$$

when $OD_{treated}$ is > to $OD_{zero}$.

If $OD_{treated}$ is above $OD_{zero}$, treatment has induced a cytostatic effect, whereas if $OD_{treated}$ is below $OD_{zero}$, cell killing has occurred. The $OD_{zero}$ depicts the cell number at the moment of drug addition, the $OD_{control}$ reflects the cell number in untreated wells and the $OD_{treated}$ reflects the cell number in treated wells on the day of the assay.

TUNEL Assay

Cells were fixed in 1% paraformaldehyde in PBS on ice for 15 min, suspended in ice cold ethanol (70%) and stored overnight at −20° C. Cells were then washed twice in PBS and resuspended in PBS containing 0.1% Triton X-100 for 5 min at 4° C. Thereafter, samples were incubated in 50 µl of solution containing TdT and FITC-conjugated dUTP deoxynucleotides 1:1 (Roche Diagnostic GmbH, Mannheim, Germany) in a humidified atmosphere for 90 min at 37° C. in the dark, washed in PBS, counterstained with propidium iodide (2.5 µg/ml, MP Biomedicals, Verona, Italy) and RNAse (10 Kunits/ml, Sigma Aldrich, Milan, Italy) for 30 min at 4° C. in the dark and analyzed by flow cytometry.

Flow Cytometric Analysis

After the end of drug exposures, medium was removed and cells were detached from the flasks by trypsin treatment, washed twice with PBS and stained according to the different methods specified below. Flow cytometric analysis was performed using a FACS Canto flow cytometer (Becton Dickinson, San Diego, Calif.). Data acquisition and analysis were performed using FACSDiva software (Becton Dickinson). Samples were run in triplicate and 10,000 events were collected for each replica. Data were the average of three experiments, with errors under 5%.

Colony-Forming Cell Assay

The colony-forming cell assay was used as previously described [Motta M R et al., Exp Hematol 1997; 25:1261-1269]. In brief, for each molecule, $5\times10^4$ cells were plated in duplicate in a complete culture medium (MethoCult H4434, StemCell Technologies, Vancouver, Canada) containing different concentrations (0.2, 2, and 20 µmol/l) of the compound. After 14 days of incubation in a humidified atmosphere of 5% $CO_2$ at the temperature of 37° C., granulocyte macrophage colony-forming unit (GM-CFU) aggregates of more than 50 cells were counted. Control cells were incubated under the same conditions but in drug-free medium.

Results

Cytotoxic Activity of (R)-Bicalutamide and its Derivative Compounds on the LNCaP Cell Line (FIGS. 1-29)

The authors examined the antitumour activity of the compounds for which the synthesis is described above, in the hormone-sensitive prostate cancer cell line LNCaP. (R)-Bicalutamide and the novel compounds were tested at the increasing concentrations of 0.002, 0.2, 2.0, and 20.0 mM. The highest dose used was chosen on the basis of the clinically achievable peak plasma concentration reported in the literature for bicalutamide (Cockshott I D. Clin Pharmacokinet. 2004; 43 (13) 855-78).

After 144-hr exposure time, the cytotoxic effect of the molecules was calculated according to the method of Monks et al. (Monks A, et al., J. Nat. Cancer Inst. 1991; 83: 757-66). Among the compounds with only cytostatic effect, (S)-8, (S)-9, (S)-36 and (R)-22 showed to be able to suppress completely the cell growth at the highest concentration tested. (S)-22, (R)-11, (S)-26, (R)-9, (S)-37, (R)-10, (R)-8, showed also cytocidal activity. Results are reported in Table 1.

TABLE 1

Growth inhibition ($GI_{50}$) and cytocidal effects by 50% ($LC_{50}$) of bicalutamide and its derivative compounds observed in LNCaP cells.

| Drugs | $GI_{50}$ [μM] | $LC_{50}$ [μM] |
|---|---|---|
| (R)-Bicalutamide | 1.8 | n.r. |
| (R)-23 | 10.6 | n.r. |
| (S)-23 | 9.4 | n.r. |
| (S)-28 | 1.8 | n.r. |
| (R)-27 | 15.2 | n.r. |
| (S)-22 | 7 | 19.8 |
| (S)-24 | 11.6 | n.r. |
| (R)-22 | 5.8 | 20 |
| (R)-26 | 9.3 | n.r. |
| (S)-26 | 6.3 | 18.3 |
| (R)-28 | 14.9 | n.r. |
| (R)-29 | 12.3 | n.r. |
| (S)-29 | 12.5 | n.r. |
| (S)-27 | 16.5 | n.r. |
| (R)-30 | n.r. | n.r. |
| (S)-30 | n.r. | n.r. |
| (R)-31 | n.r. | n.r. |
| (S)-31 | n.r. | n.r. |
| (S)-32 | n.r. | n.r. |
| (S)-8 | 10.4 | n.r. |
| (R)-11 | 8.5 | n.r. |
| (R)-9 | 1.6 | 15 |
| (S)-37 | 5.8 | 16.8 |
| (S)-9 | 4 | n.r. |
| (S)-36 | 4.3 | n.r. |
| (R)-10 | 7.4 | 17.7 |
| (R)-13 | 14 | n.r. |

The table lists the $GI_{50}$ and $LC_{50}$ values of (R)-Bicalutamide and of novel anti-androgen compounds observed in LNCaP cells. The control substance bicalutamide has a $GI_{50}$ of 1.8 μM and does not shows any cell killing activity even at the highest concentration tested value ($LC_{50}$ indicated as "not reached". Thus, bicalutamide does not have an apoptotic effect. The most effective compounds (R)-22, (R)-10, (S)-22, (S)-26, (R)-9 and (S)-37 showed $LC_{50}$ values ranging from 15 to 20 μM.
n.r. = "not reached"

Cytotoxic Effect and Apoptotic Activity of Bicalutamide Derivatives on PC-3 and DU145 Cell Lines (FIG. 30-34)

The authors tested the antitumour activity of the compounds also on PC-3 and DU145 cancer cell lines, representative of hormone-refractory prostate cancer due to AR receptor absence. The compounds (S)-22, (S)-26, (R)-9, (S)-37 and (R)-10, although cytotoxic on PC-3 and DU145 cells, showed a significant reduction in their cytotoxic proprieties when compared to their cytotoxic effects on LNCaP and LNCaP-AR cells. This suggests that the activity of the compounds is AR receptor-dependent and that the compounds are very selective.

Cytotoxic Effect and Apoptotic Activity of (R)-Bicalutamide Derivatives on the LNCaP Cell Line.

Figure 3:
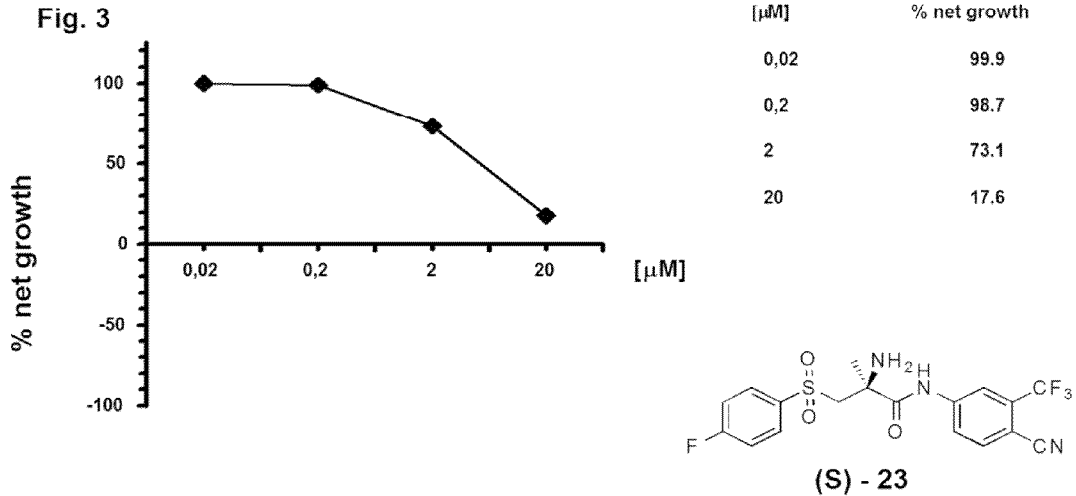
Figure 4:
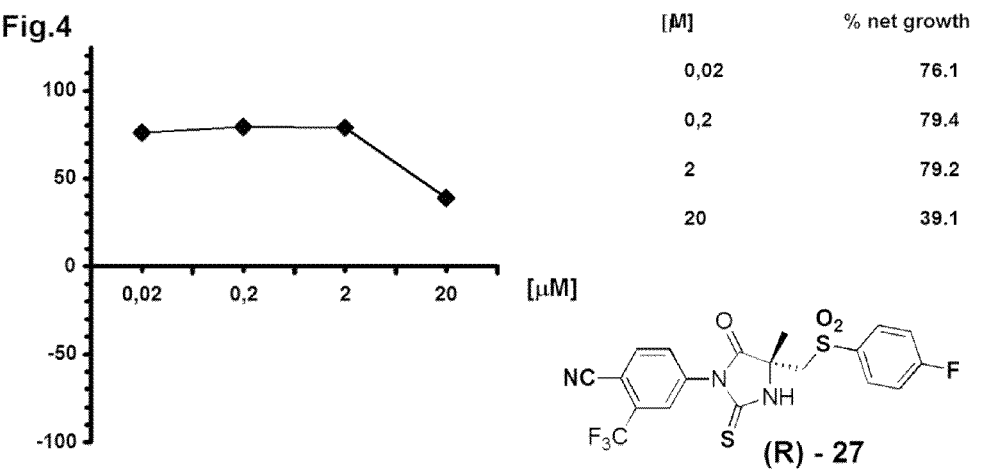
Figure 5:
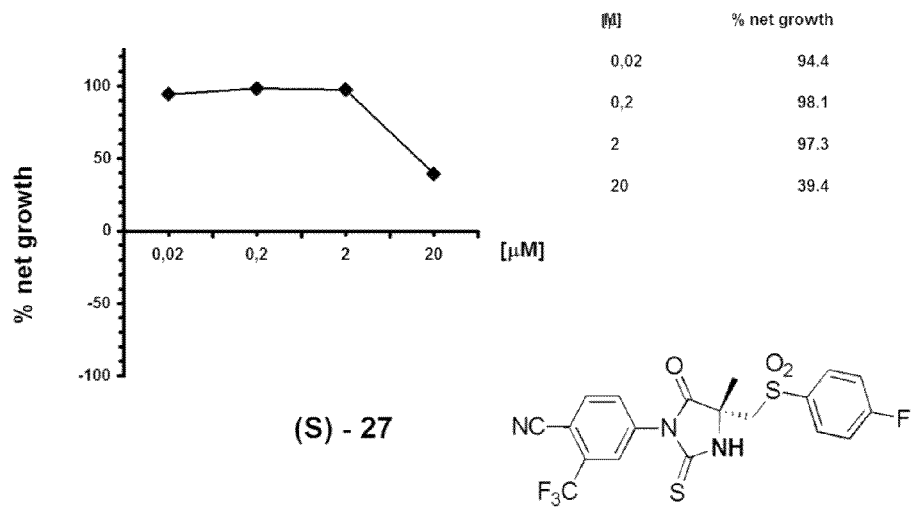
Figure 6:
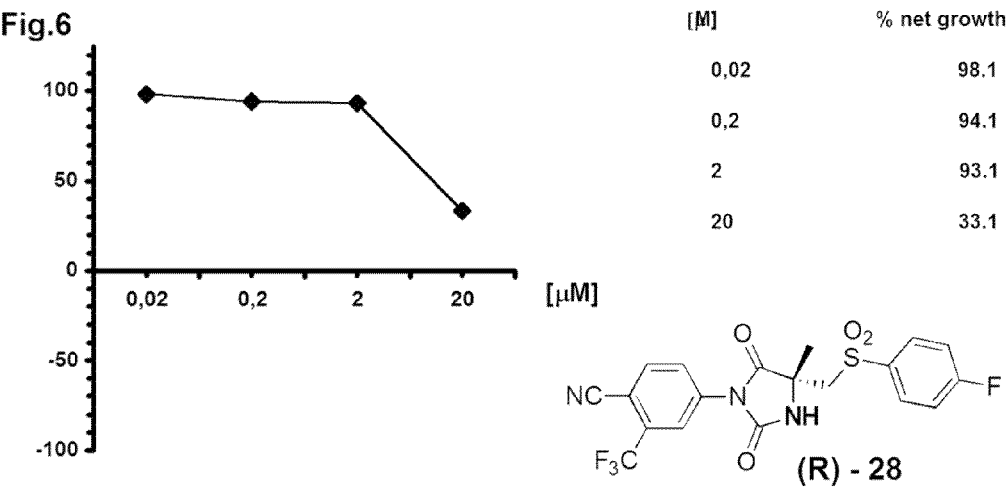
Figure 7:
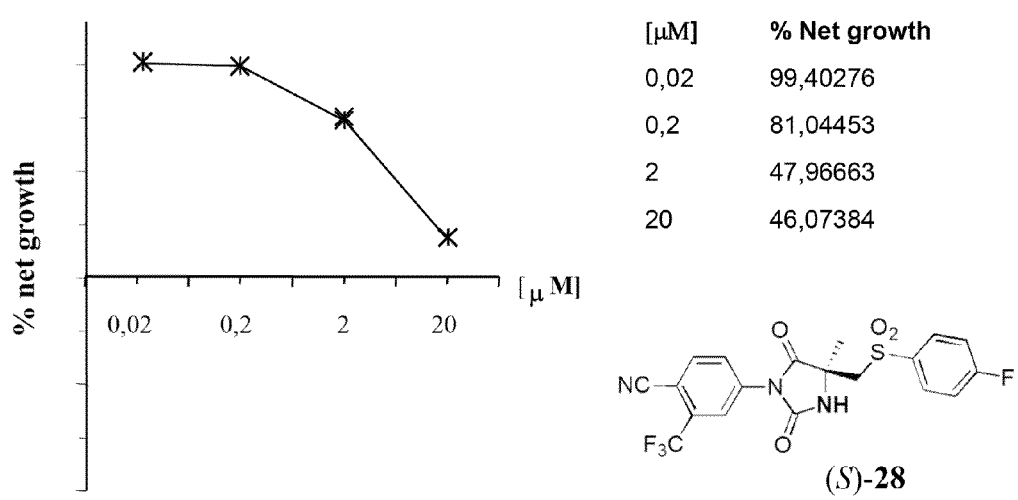
Figure 8:
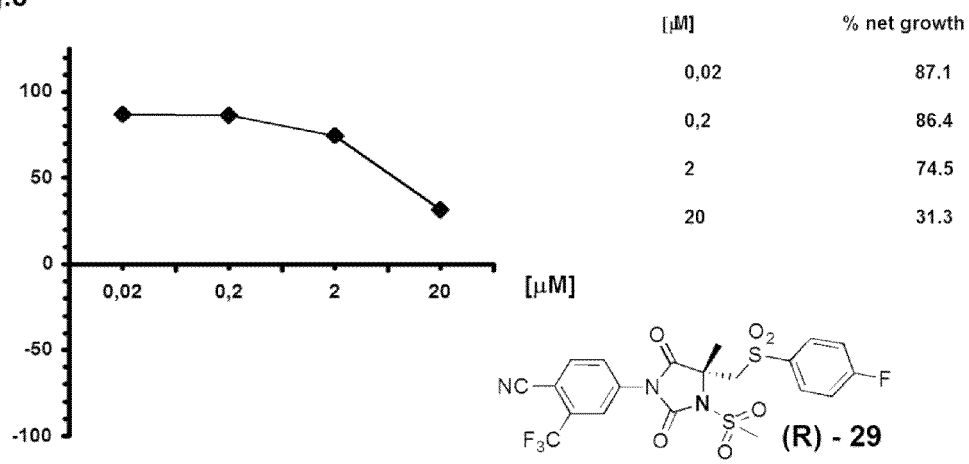
Figure 9:
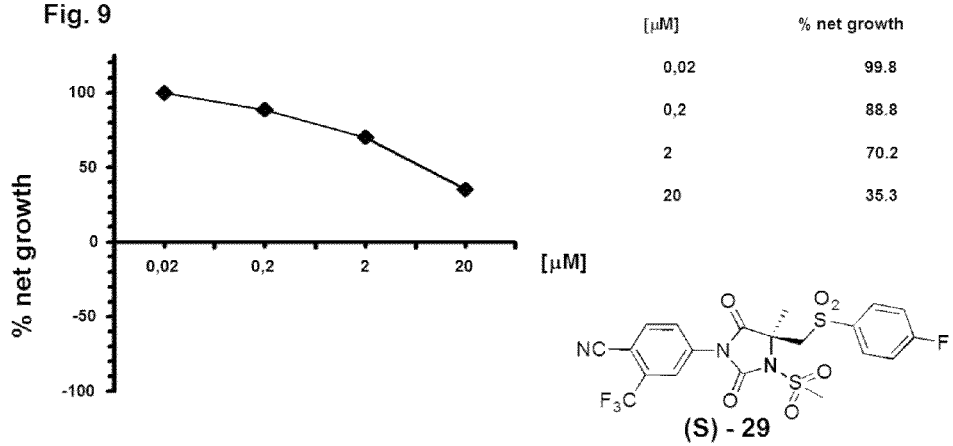
Figure 10:
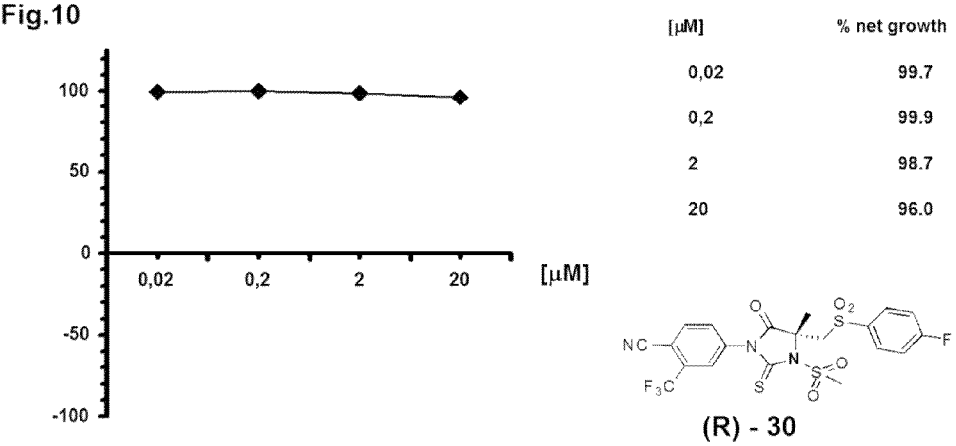
Figure 11:
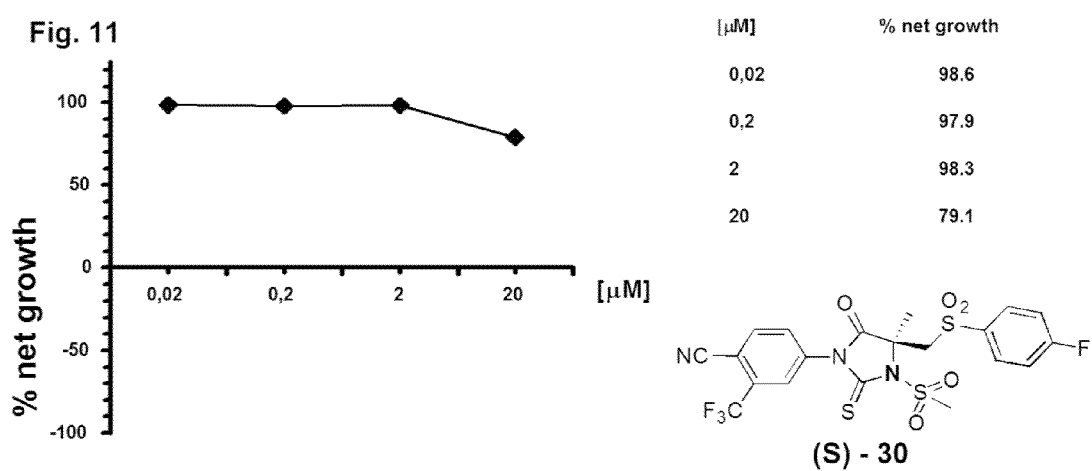
Figure 12:
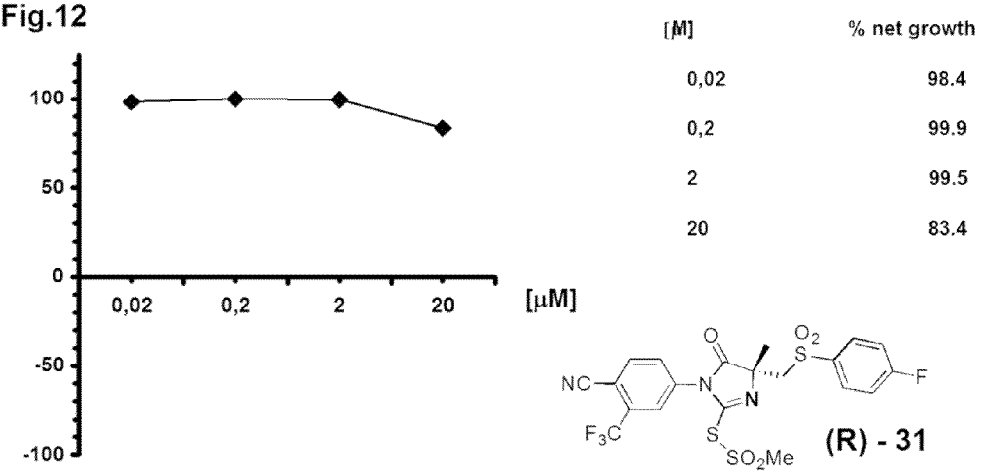
Figure 13:
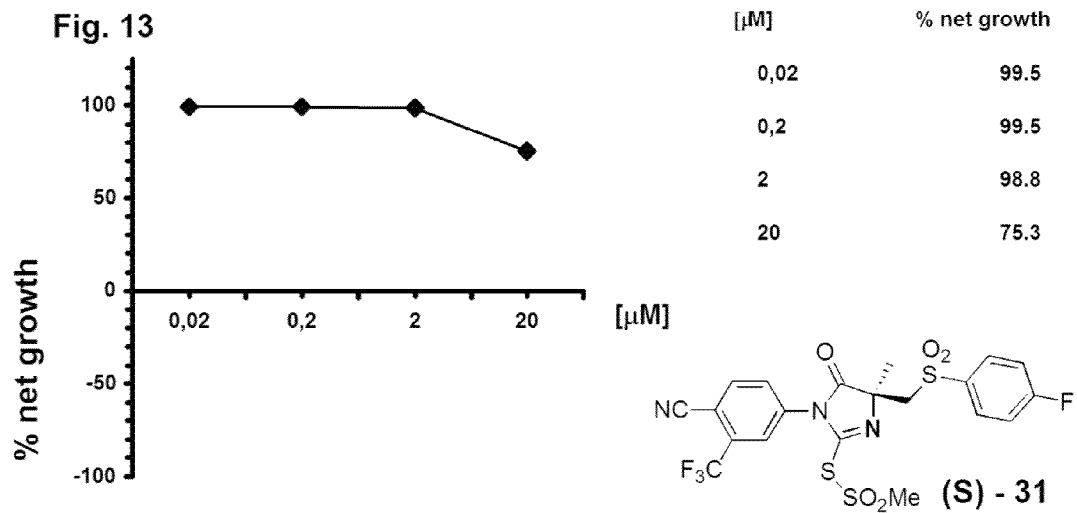
Figure 16:
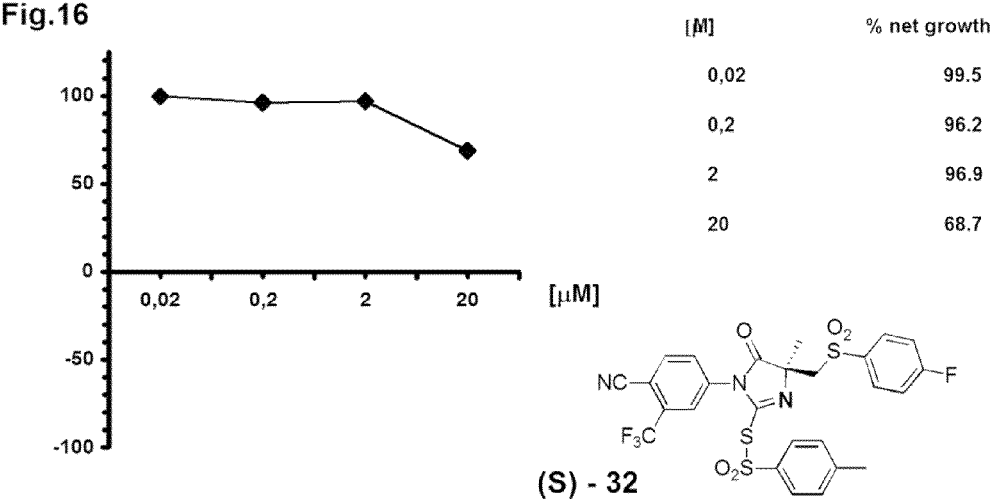
Figure 17:
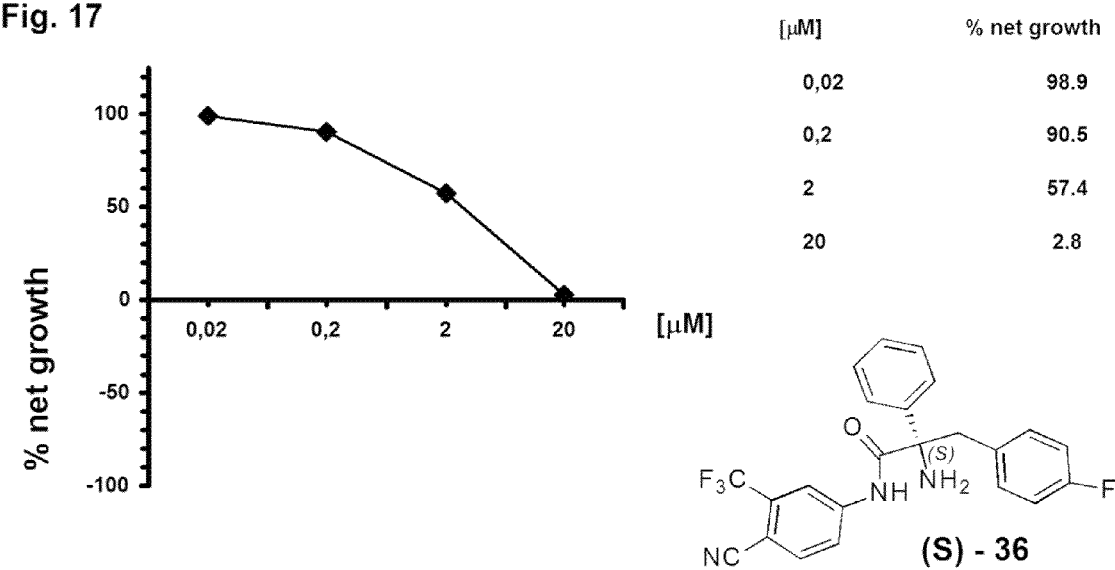
Figure 20:
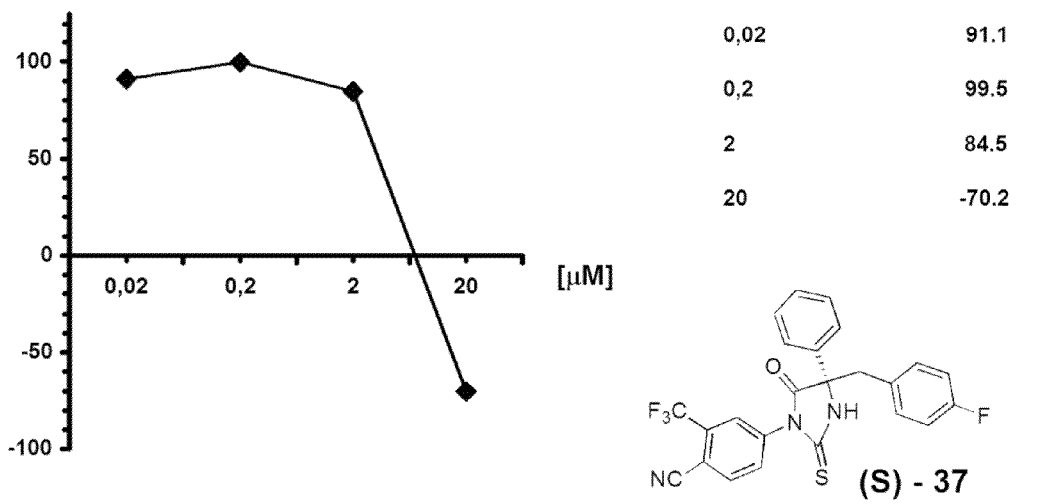
Figure 21:
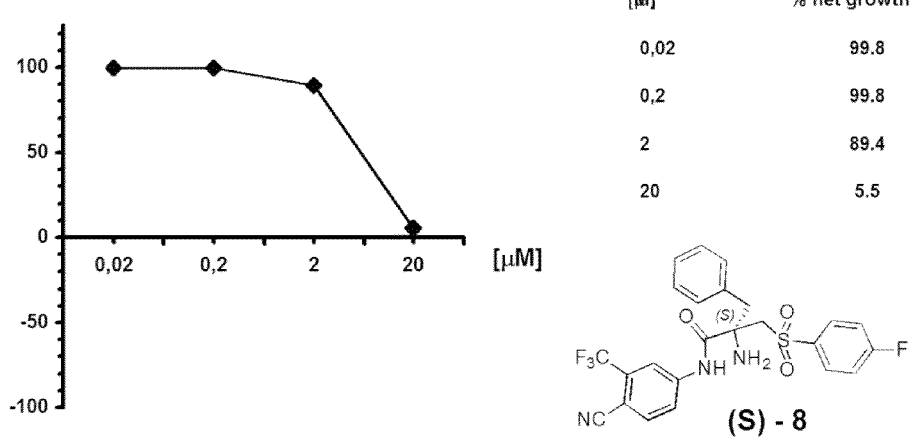
Figure 22:
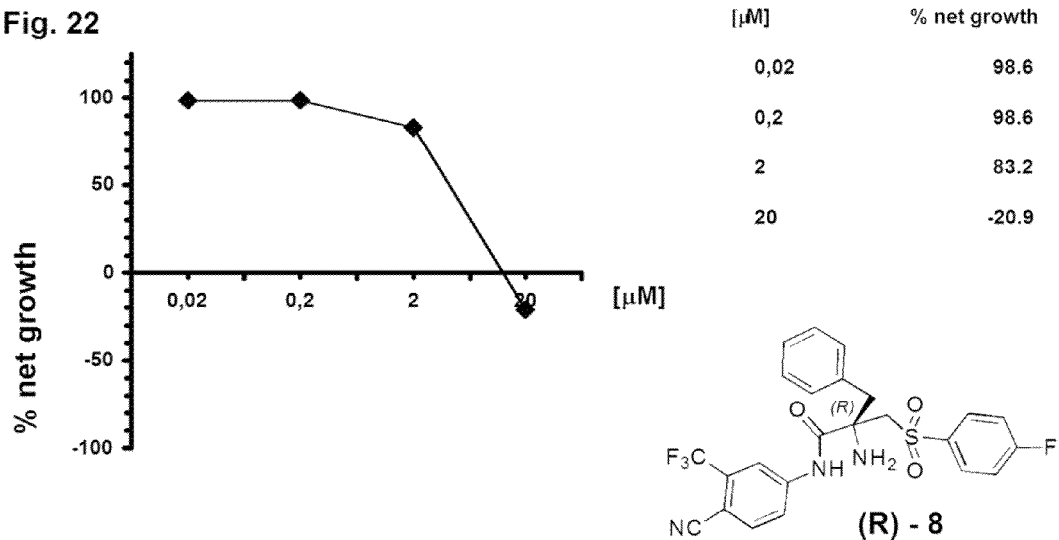
Figure 23:
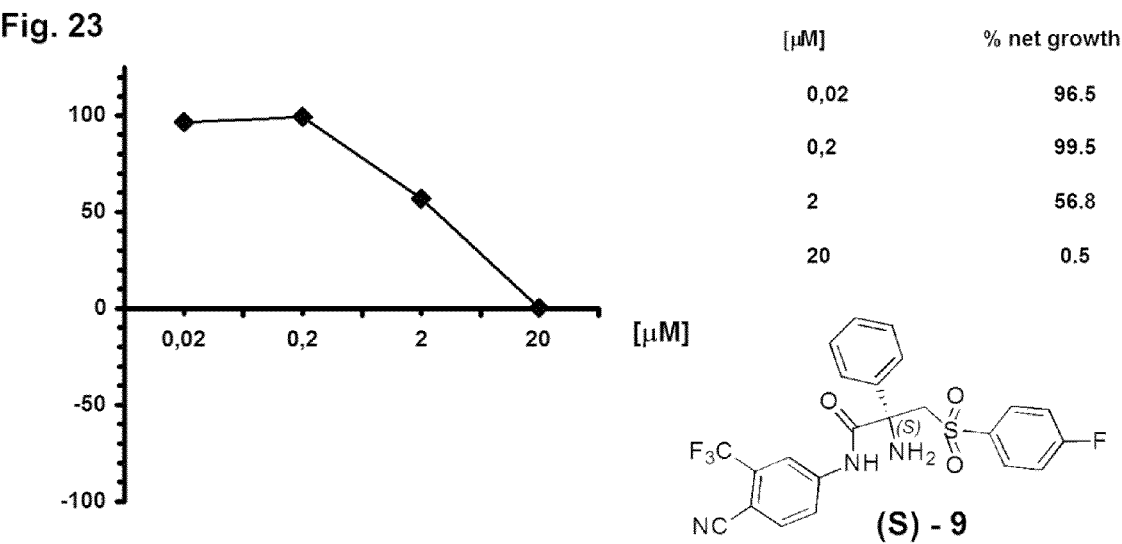
Figure 24:
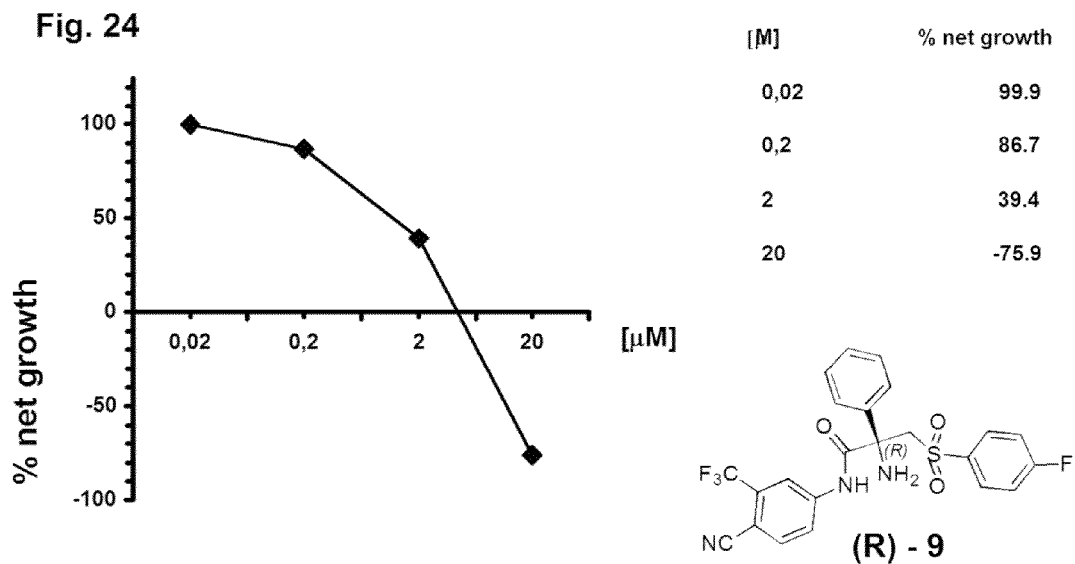
Figure 25:
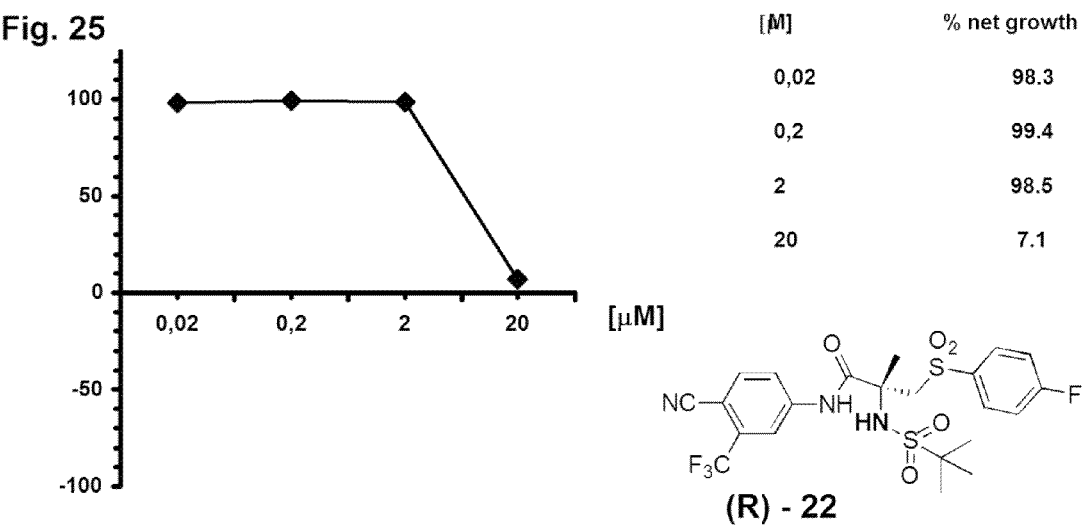
Figure 26:
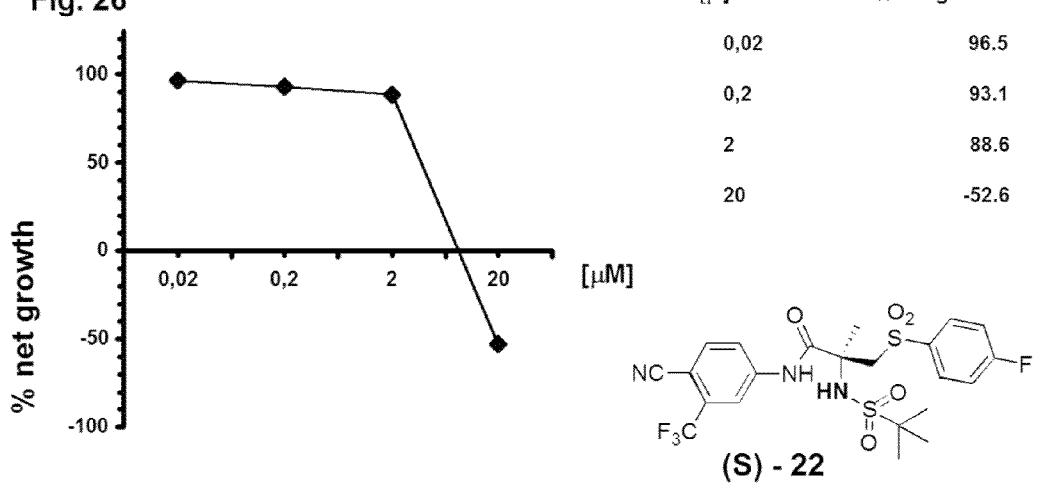
Figure 27:
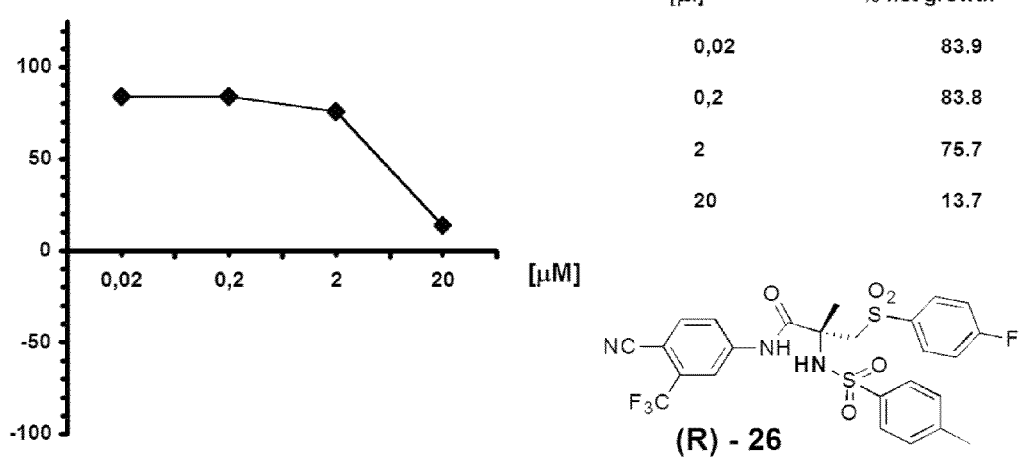
Figure 28:
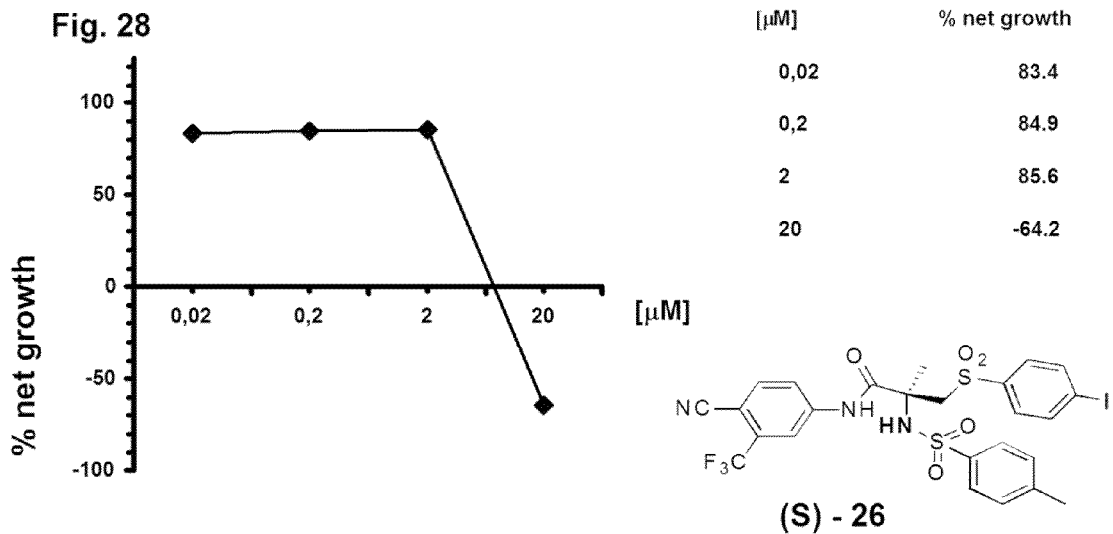
Figure 29:
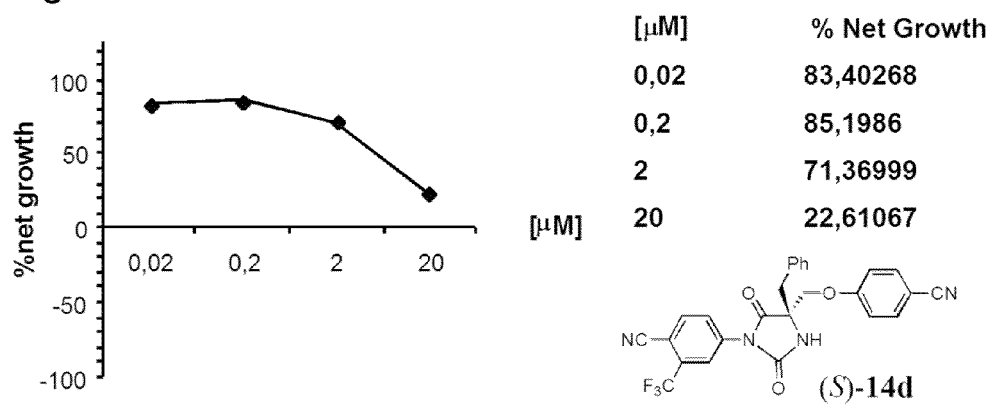
Figure 35:
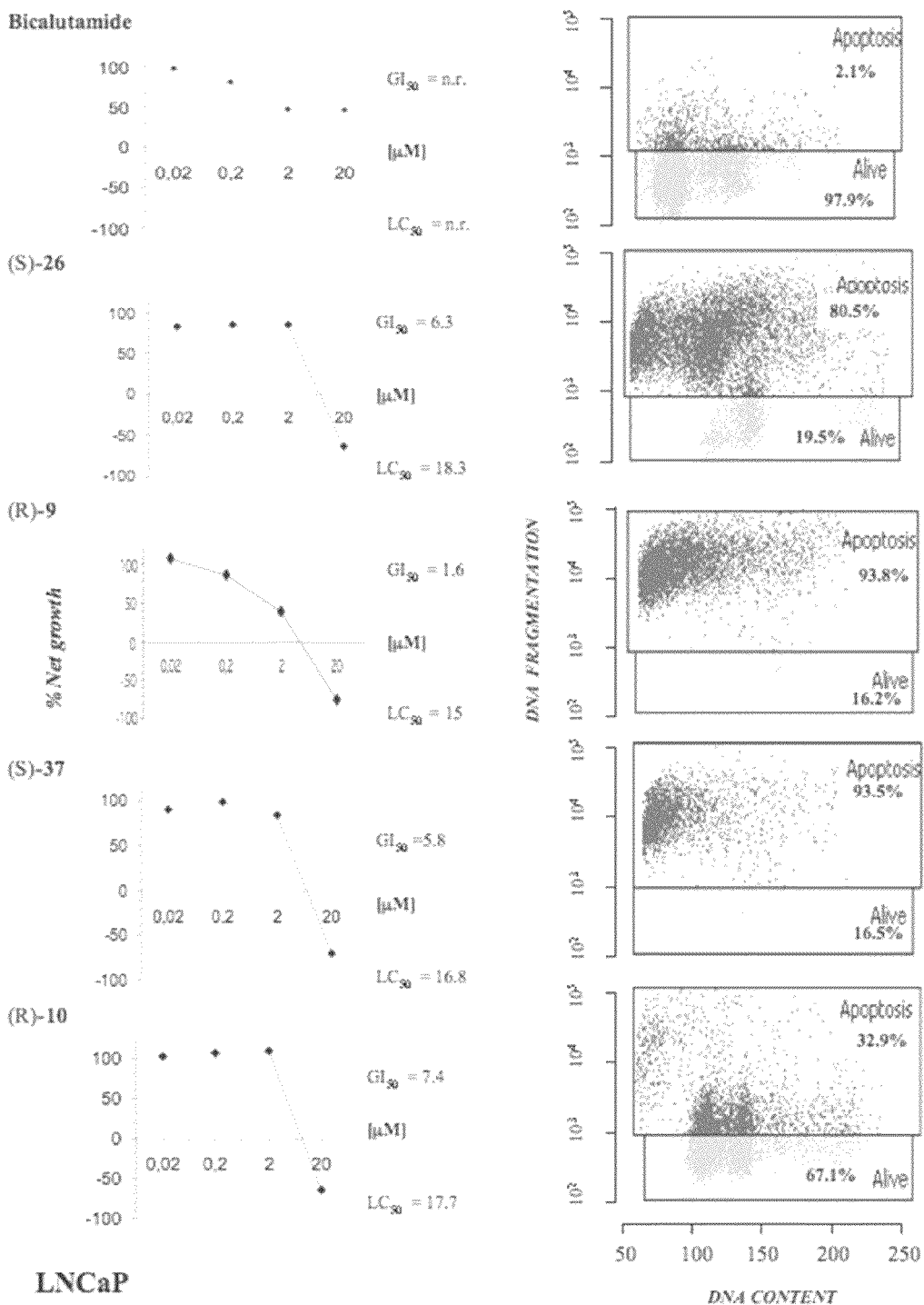
FIG. 35 illustrates the cytotoxic effect and apoptotic activity of bicalutamide and derivatives (S)-26, (R)-9, (S)-37 and (R)-10 on the LNCaP cell line. The figure reports the dose-effect curves, with the relative $GI_{50}$ and $LC_{50}$ values, and the dot plots showing the apoptotic fraction induced by the different compounds in LNCaP cells.

The FIG. 35 reports the dose-effect curves, with the relative $GI_{50}$ and $LC_{50}$ values, as already reported in Table 1, and the dot plots showing the apoptotic fraction induced by bicalutamide and (S)-26, (R)-9, (S)-37, (R)-10 compounds in LNCaP cells.

Figure 36:
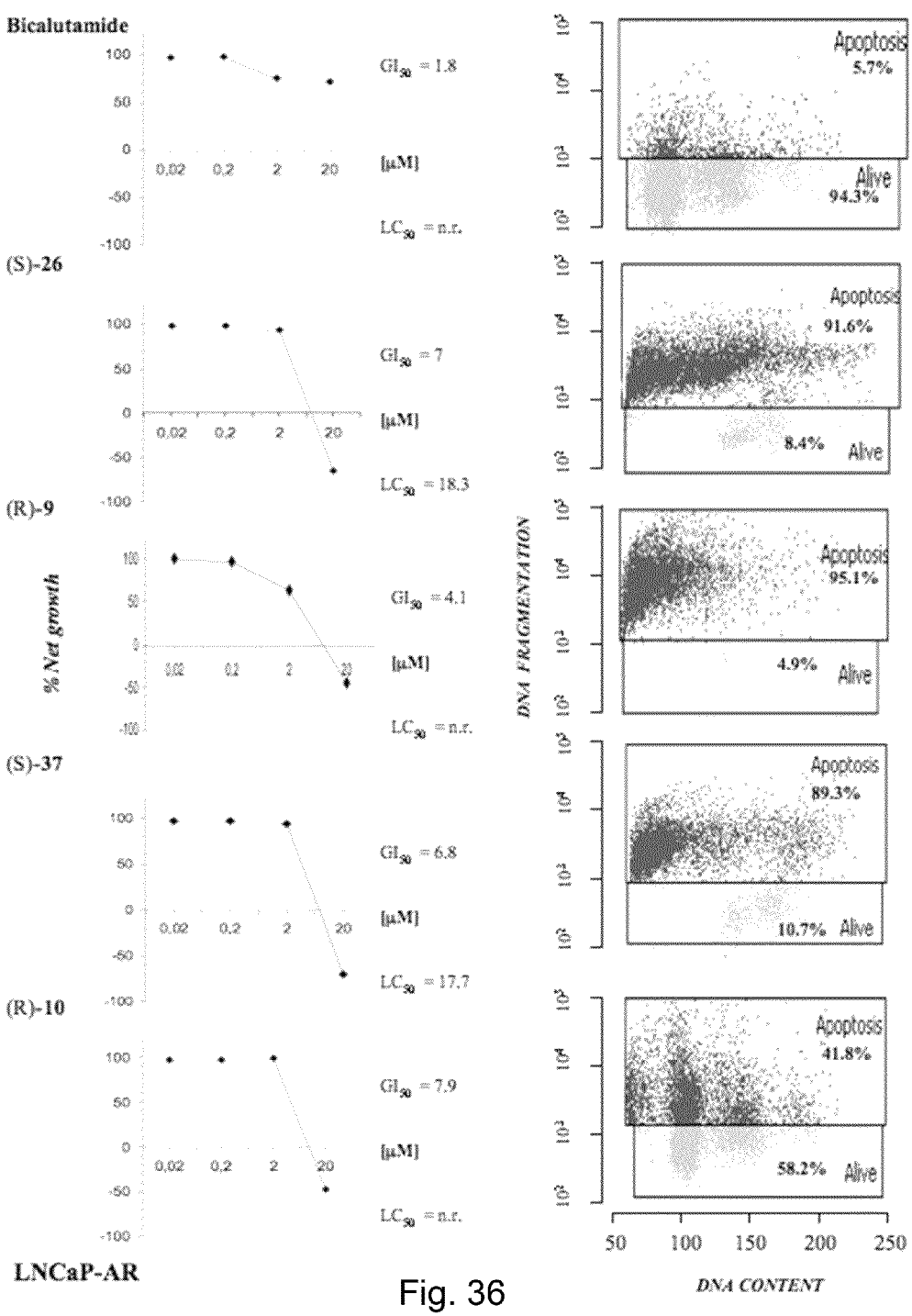
FIG. 36 illustrates the cytotoxic effect and apoptotic activity of bicalutamide and derivatives (S)-26, (R)-9, (S)-37 and (R)-10 on the LNCaP-AR cell line. The figure reports the dose-effect curves, with the relative $GI_{50}$ and $LC_{50}$ values, and the dot plots showing the apoptotic fraction induced by the different compounds in LNCaP-AR cells.

The FIG. 36 reports the dose-effect curves, with the relative $GI_{50}$ and $LC_{50}$ values, and the dot plots showing the apoptotic fraction induced by bicalutamide and (S)-26, (R)-9, (S)-37, (R)-10 compounds in LNCaP-AR cells The apoptotic data are reported in Table 2.

TABLE 2

Percentage of apoptotic cells, detected by TUNEL assay, in LNCaP and LNCaP-AR cells after 144-h exposure time to bicalutamide and its most effective derivative compounds

| | Apoptotic cells (%) | |
|---|---|---|
| Drugs | LNCaP | LNCaP-AR |
| Bicalutamide | 2.1 | 1.0 |
| (S)-22 | 6.2 | 0.0 |
| (S)-26 | 77.5 | 91.6 |
| (R)-9 | 93.5 | 83.5 |
| (S)-37 | 93.4 | 89.5 |
| (R)-10 | 35.5 | 42.7 |

The table compares the ability of (R)-bicalutamide and of the most effective compounds to induce apoptotis in LNCaP cells and in its derivative cell line LNCaP-AR, expressing high level of AR and with hormone refractory prostate cancer (HRPC) features. The cells, before TUNEL assay, were continuously exposed to the anti-androgen compounds for 144 hours at the concentration of 20.0 μM.

All the compounds showed to be able to induce higher cell death in LNCaP cells than the control substance bicalutamide. (R)-26, (R)-9, (S)-37, (R)-10 maintain a similar apoptotic property in both LNCaP and LNCaP-AR cells.

(R)-10 and (R)-26 seem to be more active, in terms of apoptosis induction, in the LNCaP derivative cell line. This could suggest a higher binding affinity for AR of (R)-26, (R)-9, (S)-37, (R)-10 in respect of bicalutamide that would explain their higher antitumour activity.

Ability of the Drugs to Inhibit Clonogenic Growth of Normal Stem Cells Derived from Human Peripheral Blood Stem Cells.

Figure 37:
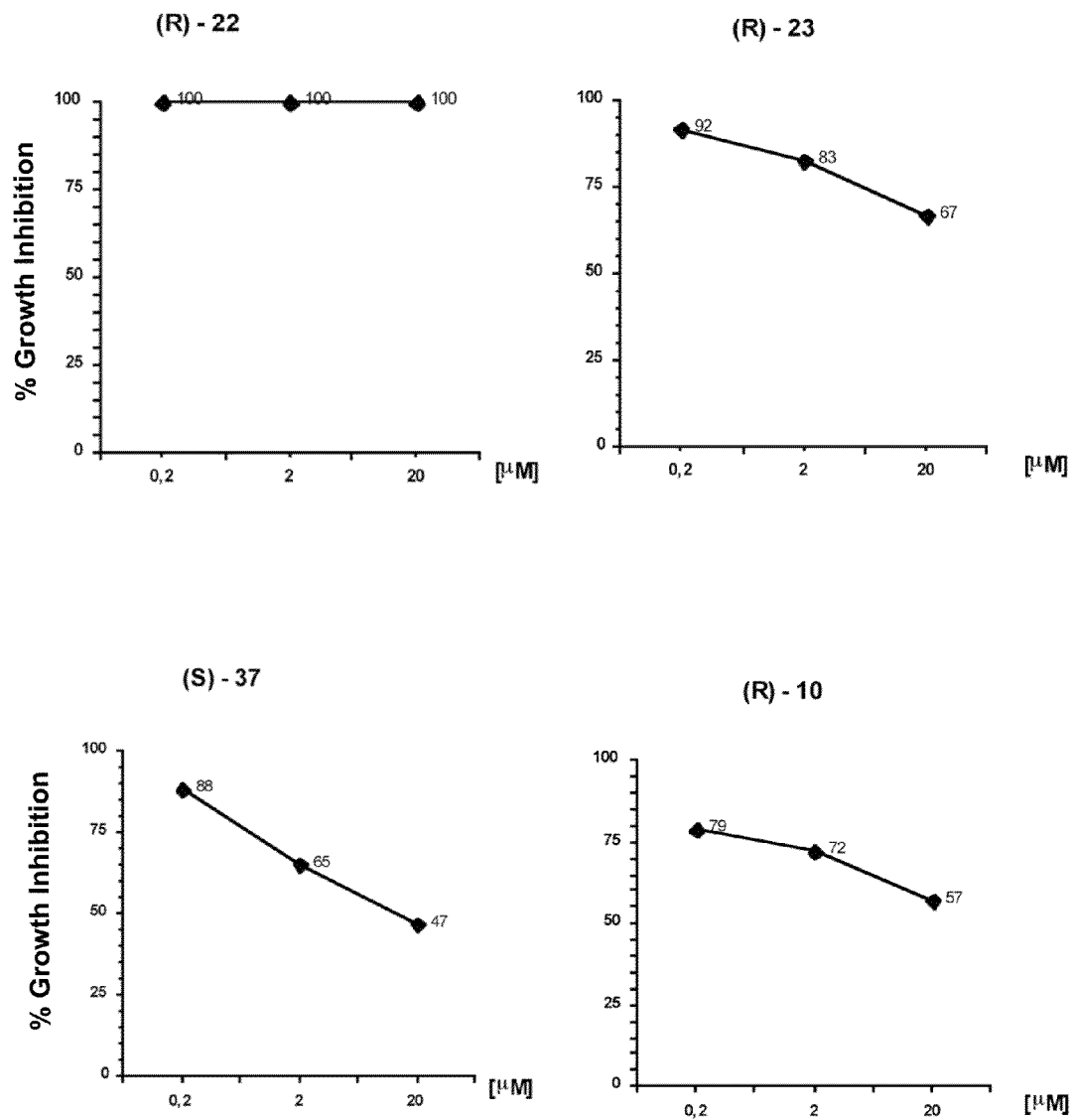
FIG. 37 illustrates the ability of the drugs (R)-22, (R)-23, (S)-37, (R)-10 to inhibit clonogenic growth of normal stem cells derived from human peripheral blood stem cells.

The authors also evaluated the potential toxicity of some of the novel compounds in normal cells as the ability of the drugs to inhibit clonogenic growth of normal stem cells derived from human peripheral blood stem cells (FIG. 37). The exposure of hematopoietic precursor to the compounds, caused low ((S)-37) or negligible (, (R)-22, (R)-23, (R)-10) toxicity at the highest concentration tested.

Example 17

Quantification of the Human Androgen Receptor (hAR) Transcriptional Activity

Constructs

The cDNA coding hAR was cloned into the pSG5 expression vector as reported previously [Chang, C. S., et al., *Science* (1988)240:324-326]. The 3416 construct (ARE-Luc), containing four copies of the wild-type slp-HRE2 (5'-TGGT-CAgccAGTTCT-3') (SEQ ID No. 1) was cloned in the NheI site in pTK-TATA-Luc [Verrijdt, G. et al., *J. Biol. Chem.* (2000)275:12298-12305].

Transactivation Assay

For androgen-stimulated transcriptional analysis, $32\times10^4$ Cos-7 cells were plated in phenol red-free DMEM containing 5% charcoal-stripped serum. After 48 h, the cells were transfected by Superfect (Qiagen) with 0.3 μg of 3416-pTK-TATA-Luc construct, together with 1.5 μg of either pSG5-empty plasmid or pSG5-hAR expressing plasmid. After 18 h, transfected cells were stimulated for 24 h with 10 nM of the synthetic androgen, R1881 (from Perkin-Elmer; dissolved in 0.001% ethanol, final concentration), in the absence or presence of the indicated concentrations of synthetic compounds. When indicated, the synthetic compounds were added alone to the cell medium. The anti-androgen Casodex (Astra-Zeneca) was used at 10 μM. It was dissolved in 0.001% (final concentration) ethanol. Control cells were treated with the vehicle alone. Lysates were prepared and the luciferase activity was measured using a luciferase assay system (Promega). The results were corrected using CH110-expressed beta-galactosidase activity (Amersham Biosciences) and luciferase activity was expressed as fold induction. Results were obtained from two or three different experiments, each performed in duplicate. Mean and SEM are shown.

AR Detection by Western Blot

For detection of ectopically expressed AR, lysates from COS cells transfected with pSG5-hAR plasmid were prepared as described [Migliaccio, et al., *EMBO J.* (1998)17: 2008-2018]. Lysates from cells transfected with the empty pSG5 plasmid were used in parallel, as a control. Protein concentrations were measured using a Bio-Rad protein assay kit (Bio-Rad Laboratories). Lysates (2 mg/ml protein concentration) were submitted to SDS-PAGE (12% acrylammide) and separated proteins were then transferred to nitrocellulose transfer membrane (Protran; Whatman GmbH) as previously described [Migliaccio, A. et al., *EMBO J.* (1998) 17:2008-2018]. To reveal expression of AR, nitrocellulose membranes were finally submitted to Western blot using the rabbit polyclonal anti-AR antibodies (either C-19 or N-20; from Santa Cruz) as described [Castoria, G. et al., *J. Cell Biol.* (2003) 161: 547-556].

Results

FIG. 38 shows that 10 nM R1881 increases by about 11 fold the transcriptional activation mediated by AR ectopically expressed in Cos-7 cells and assayed using an ARE-reporter gene (LANE 3). The antiandrogen Casodex (at 10 μM, LANE 4) inhibits such an activation. Similar inhibition is observed in cells treated with 10 nM R1881 in the presence of 10 μM (R)-9 compound (LANES 10-14). The compound (R)-22 (LANES 10-14) does not seem to be a pure antagonist, since it shows antagonistic activity when used at 10 μM in cells challenged with 10 nM R1881, whereas it functions as agonist in the range between 100 nM-10 μM.

FIG. 39 shows that 10 nM R1881 increases by about 11 fold the transcriptional activation mediated by AR ectopically expressed in Cos-7 cells and assayed using an ARE-reporter gene. The antiandrogen Casodex (at 10 μM) inhibits such an activation. Similar inhibition is observed in cells treated with 10 nM R1881 in the presence of 10 μM (R)-8. (R)-12 does not interfere in the transcriptional activity mediated by hAR in cells challenged with 10 nM R1881. It does not show agonistic activity when used alone in range between 10 nM-10 μM.

FIG. 40 shows that 10 nM R1881 increases by about 11 fold the transcriptional activation mediated by AR ectopically expressed in Cos-7 cells and assayed using an ARE-reporter gene. The antiandrogen Casodex (at 10 μM) inhibits such an activation. A robust transcriptional activation is observed in cells challenged with (R)-7c compound. It increases by about 15 fold the transcriptional activity of AR when used in the range between 10-100 nM. Its agonistic activity is inhibited by the pure antiandrogen Casodex (at 10 μM). (R)-26 does not show antagonistic activity.

FIG. 41 shows that 10 nM R1881 increases by about 11 fold the transcriptional activation mediated by AR ectopically expressed in Cos-7 cells and assayed using an ARE-reporter gene. The antiandrogen Casodex (at 10 μM) inhibits such an activation. A strong transcriptional activation is observed in cells challenged with (S)-14e compound. It increases by about 55 fold the transcriptional activity of AR when used at 100 nM.

FIG. 42 shows that 10 nM R1881 increases by about 11 fold the transcriptional activation mediated by AR ectopically expressed in Cos-7 cells and assayed using an ARE-reporter gene. The antiandrogen Casodex (at 10 μM) inhibits such an activation. Inhibition of androgen-induced transcriptional activation is observed in cells challenged with (S)-26 compound. It, however, also shows agonistic activity at 100 nM.

FIG. 43 shows that 10 nM R1881 increases by about 11 fold the transcriptional activation mediated by AR ectopically expressed in Cos-7 cells and assayed using an ARE-reporter gene. The antiandrogen Casodex (at 10 μM) inhibits such an activation. A strong inhibition of androgen-induced transcriptional activation is observed in cells challenged with (R)-11 compound, which does not show agonistic activity in the authors' experimental conditions.

Example 18

Cytotoxic Activity of the Drugs on the Human Hepatoblastoma Cell Line HepG2

The authors evaluated in vitro the potential hepato-toxicity of some of the novel compounds on HepG2 cell line, a human hepatoblastoma cell line that retains the specialized function of normal hepatocytes [Knowles B B, et al., Science 1980, 209:497-499; Aden D P, et al., Nature, 1979, 282:615-616]. As shown in FIG. 44, a significant toxicity was observed only when this cell line was exposed to the compound (S)-37, reaching values of $GI_{50}$ and $LC_{50}$ of 7.4 μM and 17.7 μM, respectively. The other compounds, (R)-22, (R)-23, (R)-10, caused only negligible toxicity also at the highest concentration tested.

The invention claimed is:
1. A compound of general formula (I):

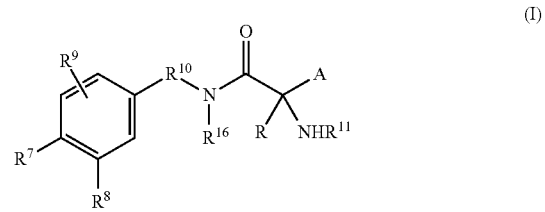

wherein
R is: H, aryl, optionally substituted aryl, heteroaryl, optionally substituted heteroaryl, straight or branched $C_{1-10}$ alkyl, wherein the alkyl may be substituted with one or more substituents which may be the same or different, and include halo, cycloalkyl containing three to six carbon atoms, hydroxy, alkoxy, amino, acylamino, aroylamino, carboxy, alkoxycarbonyl, aralkyloxycarbonyl;
R is also $C_1$-$C_4$-arylalkyl, $C_{1-4}$ heteroarylalkyl or substituted heterocyclylalkyl;
$R^9$ is H, F, Cl, I or Br;
$R^7$ is H, CN, $NO_2$, F, Cl, I, Br, carbamoyl, or alkyl, alkoxy, alkanoyl, alkylthio, alkylsulphinyl, alkylsulphonyl, perfluoroalkyl, perfluoroalkylthio, perfluoroalkylsulphinyl or perfluoroalkysulphonyl each being substituted or unsubstituted and having up to 4 carbon atoms, or phenyl, phenylthio, phenylsulphinyl or phenylsulphonyl; each being substituted or unsubstituted;
$R^8$ is cyano, carbamoyl, nitro, fluoro, chloro, bromo, iodo or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each being substituted or unsubstituted and having up to 4 carbon atoms, or phenyl, phenylthio, phenylsulphinyl or phenylsulphonyl, each being substituted or unsubstituted;

$R^{10}$ is $C_1$-$C_4$ alkyl or a bond;

$R^{16}$ is H, $C_1$-$C_4$-alkyl, —CO—, —CS—, —SO—, —SO$_2$—, —$R^p$CS—, —$R^p$CO—, —$R^p$SO—, —$R^p$SO$_2$— wherein $R^p$ is a $C_1$-$C_4$ alkyl and with the condition that when $R^{16}$ is —CO— or —CS—, it is connected to NHR$^{11}$ to form a cycle; $C_1$-$C_4$-alkyl, —SO—, —SO$_2$—, —$R^p$CS—, —$R^p$CO—, —$R^p$SO—, —$R^p$SO$_2$— can also be connected to NHR$^{11}$ to form a cycle;

$R^{11}$ is H, $C_1$-$C_6$ alkyl, substituted $C_1$-$C_6$ alkyl, $C_1$-$C_6$ hetero alkyl, substituted $C_1$-$C_6$ hetero alkyl, aryl, substituted aryl, $C_1$-$C_4$-alkylaryl, hetero aromatic $C_1$-$C_4$ alkyl, aromatic hetero cycle, substituted aromatic hetero cycle, a protecting group or a chiral auxiliary; wherein the protecting group is selected from the group consisting of —COR$^r$, —COOR$^r$, —OSO$_2$R$^r$, —SO$_2$R$^r$, and —SR$^r$; wherein the chiral auxiliar is selected from the group consisting of —OS(O)R$^r$ and —OP(O)R$^s$R$^r$ where R$^r$ and R$^s$ can be the same or different; R$^r$ and R$^s$ are selected from the group consisting of $C_1$-$C_6$ alkyl, $C_1$-$C_6$ halo-alkyl, aryl, substituted aryl, aromatic hetero cycle, and substituted aromatic hetero cycle; and A has the structure of formula II:

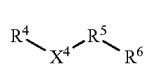

(II)

wherein $R^4$ is substituted or unsubstituted alkyl (alkylene) having up to 6 carbon atoms;

$X^4$ is oxygen, sulfur, sulfinyl (—SO—), sulfonyl (—SO$_2$—) imino (—NH—) or alkylimino (—NR$^n$—) wherein R$^n$ is H, $C_1$-$C_4$ alkyl;

$R^5$ is a direct bond or a substituted or unsubstituted alkylene having up to 6 carbon atoms;

$R^6$ is selected from the group consisting of furyl, thienyl, pyrrolyl, pyridyl, imidazolyl, thiazolyl, pyrimidinyl, thiadiazolyl, triazolyl, benzimidazolyl, benzothiazolyl, indolyl, benzothienyl, quinolyl, isoquinolyl, benzofuryl, and 1,2-dihydro-2-oxoquinolyl.

2. The compound according to claim 1 represented by the following stereoisomer structure:

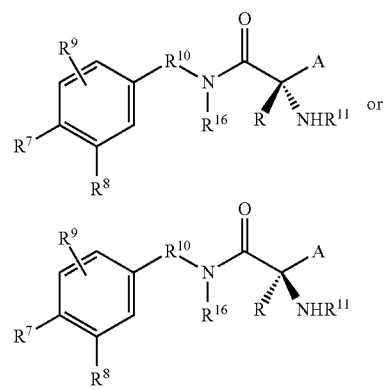

wherein the substituents are defined as in claim 1.

3. A compound having the formula III, IV or V:

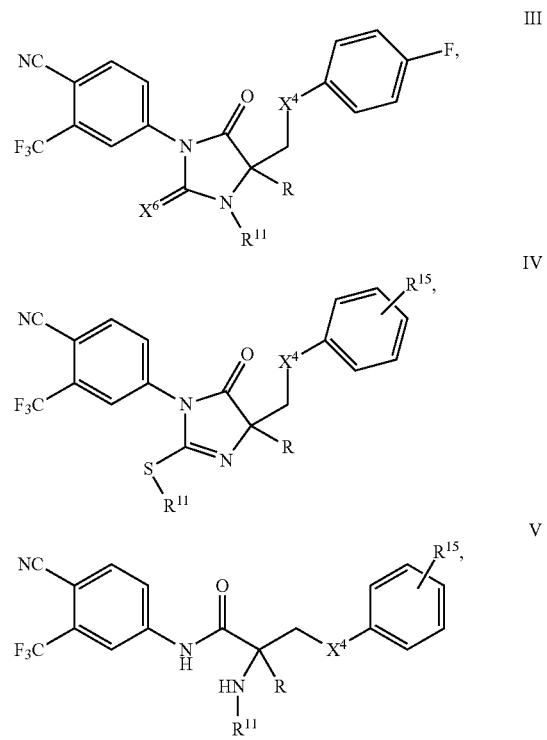

wherein $X^4$ is O, S, —SO—, —SO$_2$—, —NH— or —NR$^n$— in which R$^n$ is H, $C_1$-$C_4$ alkyl;

R is: H, aryl, optionally substituted aryl, heteroaryl, optionally substituted heteroaryl, straight or branched $C_{1-10}$ alkyl, wherein the alkyl may be substituted with one or more substituents which may be the same or different, and include halo, cycloalkyl containing three to six carbon atoms, hydroxy, alkoxy, amino, acylamino, aroylamino, carboxy, alkoxycarbonyl, aralkyloxycarbonyl;

R is also $C_1$-$C_4$-arylalkyl, $C_{1-4}$ heteroarylalkyl or substituted heterocyclylalkyl;

$R^{11}$ is H, $C_1$-$C_6$ alkyl, substituted $C_1$-$C_6$ alkyl, $C_1$-$C_6$ hetero alkyl, substituted $C_1$-$C_6$ hetero alkyl, aryl, substituted aryl, $C_1$-$C_4$-alkylaryl, hetero aromatic $C_1$-$C_4$ alkyl, aromatic hetero cycle, substituted aromatic hetero cycle, a protecting group or a chiral auxiliary; wherein the protecting group is selected from the group consisting of —COR$^r$, —COOR$^r$, —OSO$_2$R$^r$, —SO$_2$R$^r$, and —SR$^r$; wherein the chiral auxiliary is selected from the group consisting of —OS(O)R$^r$ and —OP(O)R$^s$R$^r$ where R$^r$ and R$^s$ can be the same or different; R$^r$ and R$^s$ are selected from the group consisting of $C_1$-$C_6$ alkyl, $C_1$-$C_6$ halo-alkyl, aryl, substituted aryl, aromatic hetero cycle, and substituted aromatic hetero cycle;

$R^{15}$ is H, halogen, nitro, carboxyl, carbamoyl and cyano, alkyl, alkoxy, alknoyl, alkylthio, alkylsulphinyl, alkylsulphonyl, perfluoroalkyl, perfluoroalkoxy, perfluoroalkylthio, perfluoroalkylsulfinyl, perfluoroalkylsulphonyl, alkoxycarbonyl and N-alkylcarbamoyl, each up to 4 carbon atoms, phenyl, phenylthio, phenylsulfinyl or phenylsulfonyl; and $X^6$ is O or S.

4. The compound according to claim 1 having the formula selected from the group consisting of:

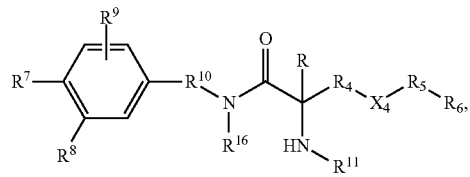

(XXIV)

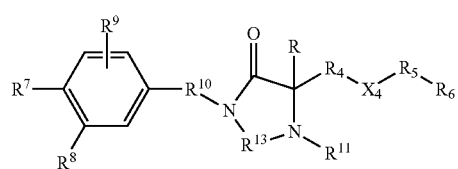

(XVI)

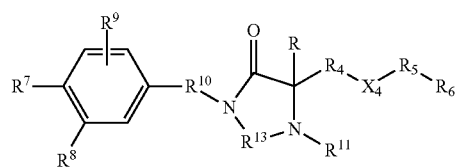

(XVI)

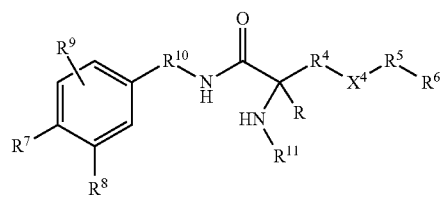

(XIV)

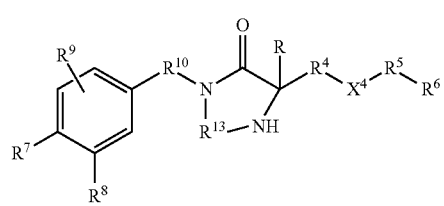

(XV)

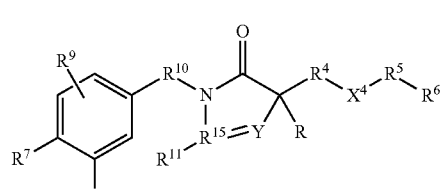

(XVII)

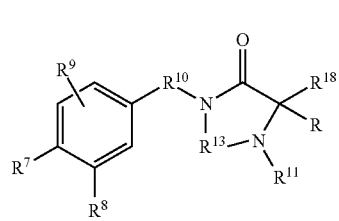

(XXI)

wherein $R^{13}$ is $C_1$-$C_4$-alkyl, —CO—, —CS—, —SO—, —SO_2—, —$R^p$CO—, —$R^p$CS—, —$R^p$SO—, —$R^p$SO_2— in which $R^p$ is a $C_1$-$C_3$-alkyl;

$R^{15}$ is —C—S—;

$R^{18}$ is aryl, $C_1$-$C_4$-alkyl, $C_1$-$C_4$-heteroalkyl, $C_1$-$C_4$-arylalkyl, $C_1$-$C_4$-heteroarylalkyl, substituted $C_1$-$C_4$-aryla lkyl, substituted $C_1$-$C_4$-heteroarylalkyl or it is A as defined in claim 1; and the other substituents are defined as in claim 1.

5. The compound according to claim 3 being selected from the following structures:

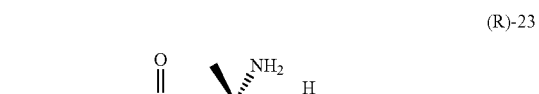

(R)-23

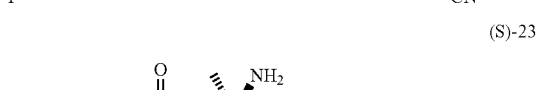

(S)-23

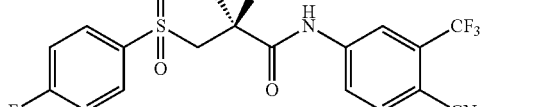

(S)-28

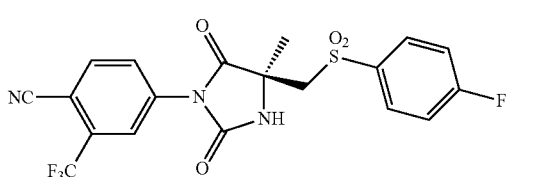

(R)-28

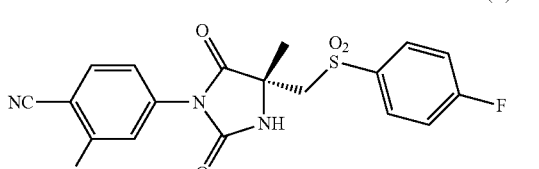

(R)-27

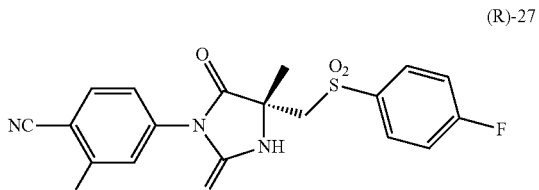

(S)-27

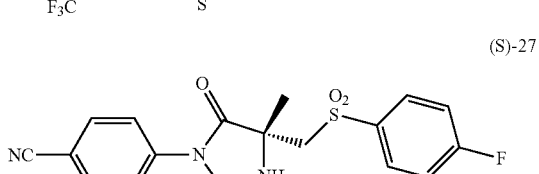

(R)-22

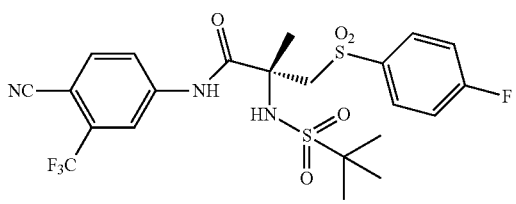

-continued

-continued (S)-31
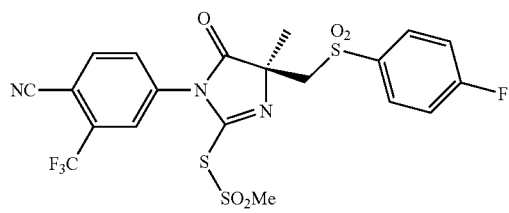

(S)-32
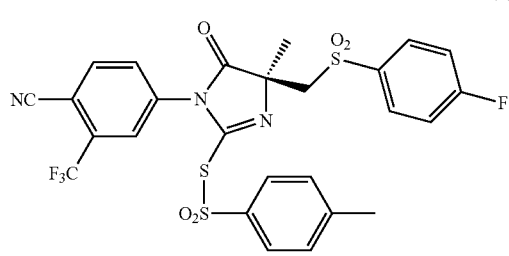

(R)-11
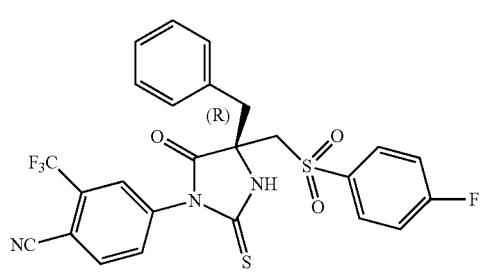

(R)-10
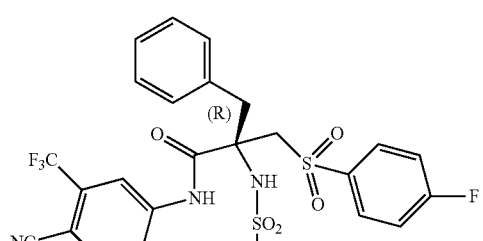

(R)-13
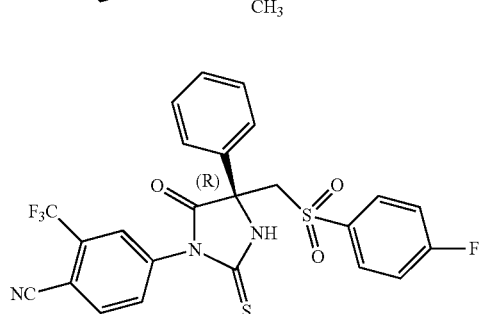

(S)-7d
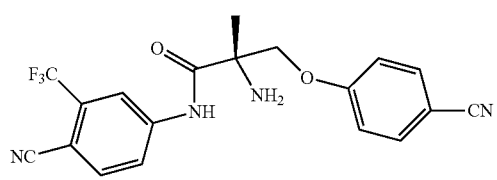

-continued (S)-14d
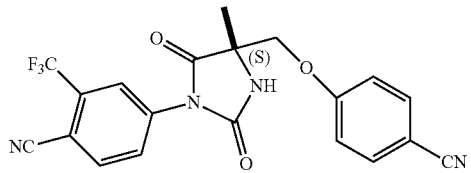

(S)-14e
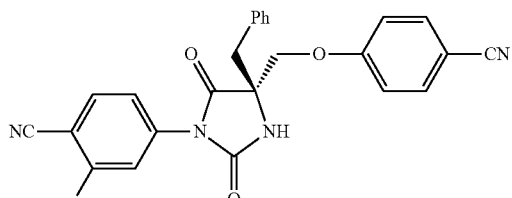

(S)-7c
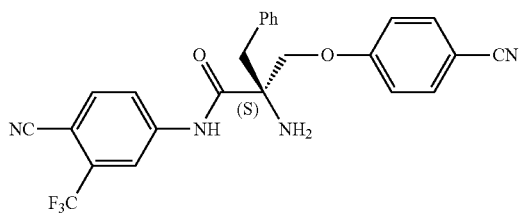

(R)-12
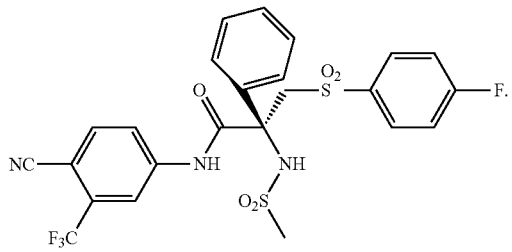

6. A pharmaceutical composition comprising a carrier and the compound according to claim 1, an isomer thereof, a pharmaceutically acceptable salt thereof, a crystal or N-oxide thereof, a hydrate thereof or any combination thereof.

7. A method for the preparation of a compound of general formula (I):

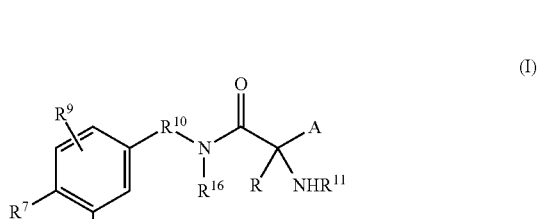

wherein

R is H, aryl, optionally substituted aryl, heteroaryl, optionally substituted heteroaryl, straight or branched $C_{1-10}$ alkyl, wherein the alkyl may be substituted with one or more substituents which may be the same or different, and include halo, cycloalkyl containing three to six carbon atoms, hydroxy, alkoxy, amino, acylamino, aroylamino, carboxy, alkoxycarbonyl, aralkyloxycarbonyl;

R is also $C_1$-$C_4$-arylalkyl, $C_{1-4}$ heteroarylalkyl or substituted heterocyclylalkyl;

$R^9$ is H, F, Cl, I or Br;

$R^7$ is H, CN, $NO_2$, F, Cl, I, Br, carbamoyl, or alkyl, alkoxy, alkanoyl, alkylthio, alkylsulphinyl, alkylsulphonyl, perfluoroalkyl, perfluoroalkylthio, perfluoroalkylsulphinyl or perfluoroalkysulphonyl each being substituted or unsubstituted and having up to 4 carbon atoms, or phenyl, phenylthio, phenylsulphinyl or phenylsulphonyl; each being substituted or unsubstituted;

$R^8$ is cyano, carbamoyl, nitro, fluoro, chloro, bromo, iodo or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each being substituted or unsubstituted and having up to 4 carbon atoms, or phenyl, phenylthio, phenylsulphinyl or phenylsulphonyl, each being substituted or unsubstituted;

$R^{10}$ is $C_1$-$C_4$alkyl or a bond;

$R^{16}$ is H, $C_1$-$C_4$-alkyl, —CO—, —CS—, —SO—, —$SO_2$—, —$R^pCS$—, —$R^pCO$—, —$R^pSO$—, —$R^pSO_2$— wherein $R^p$ is a $C_1$-$C_4$ alkyl and with the condition that when $R^{16}$ is —CO— or —CS—, it is connected to $NHR^{11}$ to form a cycle; $C_1$-$C_4$-alkyl, —SO—, —$SO_2$—, —$R^pCS$—, —$R^pCO$—, —$R^pSO$—, —$R^pSO_2$— can also be connected to $NHR^{11}$ to form a cycle;

$R^{11}$ is H, $C_1$-$C_6$ alkyl, substituted $C_1$-$C_6$ alkyl, $C_1$-$C_6$ hetero alkyl, substituted $C_1$-$C_6$ hetero alkyl, aryl, substituted aryl, $C_1$-$C_4$-alkylaryl, hetero aromatic $C_1$-$C_4$ alkyl, aromatic hetero cycle, substituted aromatic hetero cycle, a protecting group or a chiral auxiliary; wherein the protecting group is selected from the group consisting of —$COR^r$, —$COOR^r$, —$OSO_2R^r$, —$SO_2R^r$ and —$SR^r$; wherein the chiral auxiliar is selected from the group consisting of —OS(O)$R^r$ and —OP(O)$R^sR^r$ where $R^r$ and $R^s$ can be the same or different; $R^r$ and $R^s$ are selected from the group consisting of $C_1$-$C_6$ alkyl, $C_1$-$C_6$ halo-alkyl, aryl, substituted aryl, aromatic hetero cycle, and substituted aromatic hetero cycle; and A has the structure of formula II:

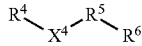

(II)

wherein $R^4$ is substituted or unsubstituted alkyl (alkylene) having up to 6 carbon atoms;

$X^4$ is oxygen, sulfur, sulfinyl (—SO—), sulfonyl (—$SO_2$—) imino (—NH—) or alkylimino (—$NR''$—) wherein is $R''$ is H, $C_1$-$C_4$ alkyl;

$R^5$ is a direct bond or a substituted or unsubstituted alkylene having up to 6 carbon atoms;

$R^6$ is a direct bond or an unsubstituted alkylene having 1, 2 or 3 carbon atoms; or $R^6$ is alkyl, alkenyl, hydroxyalkyl, or cycloalkyl each being substituted or unsubstituted and having up to 6 carbons; or $R^6$ is phenyl which bears one, two or three substituents independently selected from the group consisting of hydrogen, halogen, nitro, carboxy, carbamoyl and cyano, alkyl, alkoxy, alknoyl, alkylthio, alkylsulfinyl, alkylsulfonyl, perfluoroalkyl, perfluoroalkoxy, perfluoroalkylthio, perfluoroalkylsulfinyl, perfluoroalkylsulfonil, alkoxycarbonyl and N-alkylcarbamoyl, each up to 4 carbon atoms and phenyl, phenylthio, phenylsulfynil and phenylsulfonyl, or $R^6$ is naphthyl, or $R^6$ is a 5- or 6-membered saturated or unsaturated heterocyclic which contains one, two or three heteroatoms selected from the group consisting of oxygen, nitrogen and sulfur, which heterocyclic may be single ring or may be fused to a benzo-ring, and which heterocyclic is unsubstituted or bears one or two halogen, cyano or amino, or alkyl, alkoxy, alkylsulfinyl or alkylsulfonyl each of up to 4 carbon atoms, or oxy or hydroxy substituents, or which is sufficiently saturated and may bear one or two oxo substituents; and wherein $R^6$ is selected from the group consisting of furyl, thinly, pyrrolyl, pyridyl, imidazolyl, thiazolyl, pyrimidinyl, thiadiazolyl, triazolyl, benzimidazolyl, benzothiazolyl, indolyl, benzothienyl, quinolyl, isoquinolyl, benzofuryl, and 1,2-dihydro-2-oxoquinolyl; and which comprises one of the synthetic procedures reported in scheme 1 or 2:

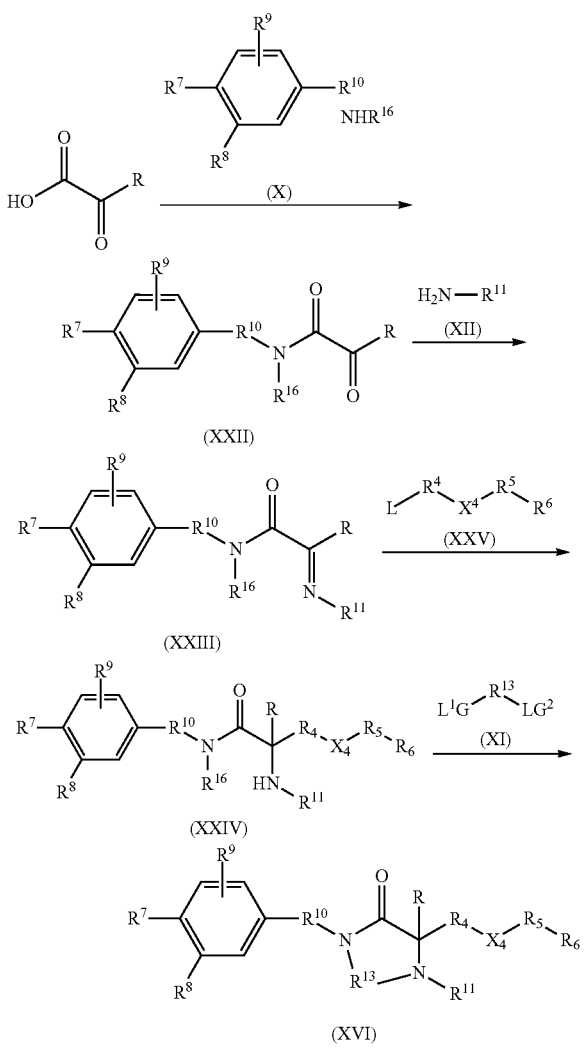

Scheme 2
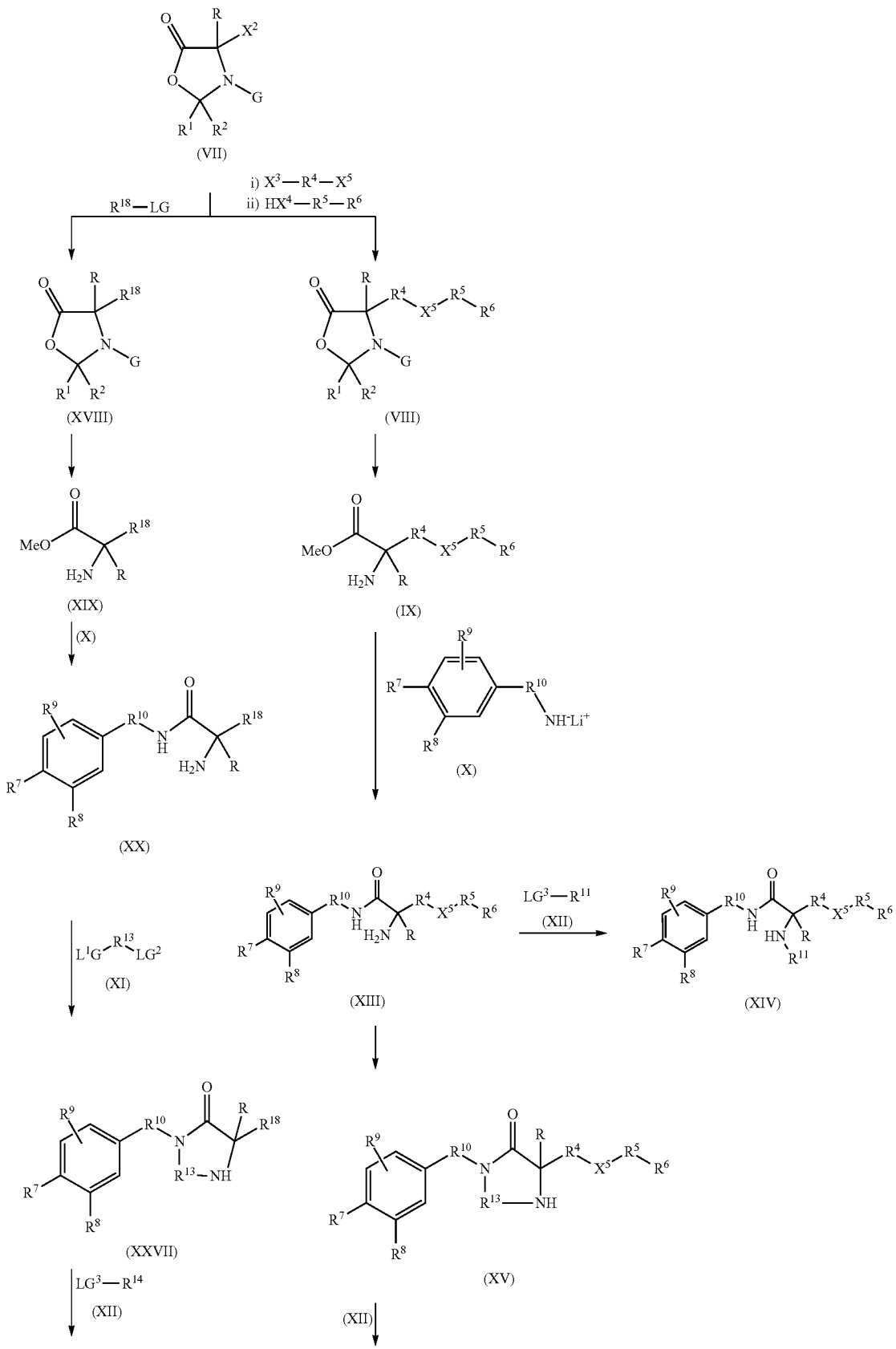

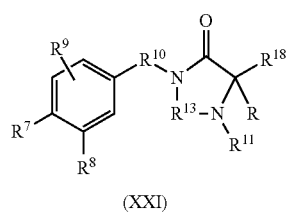 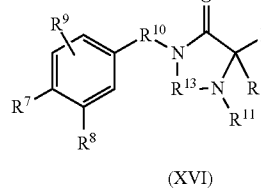 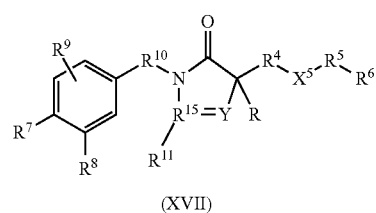

(XXI) (XVI) (XVII)

wherein $R^{13}$ is —CO— or —CS—, —SO—, —SO$_2$—, —R$^p$CO—, —R$^p$CS—, —R$^p$SO—, —R$^p$SO$_2$—, wherein R$^p$ is a $C_1$-$C_3$-alkyl;

$R^{15}$ is —C—S—;

$R^{18}$ is aryl, $C_1$-$C_4$-alkyl, $C_1$-$C_4$-heteroalkyl, $C_1$-$C_4$-arylalkyl, $C_1$-$C_4$-heteroarylalkyl, substituted $C_1$-$C_4$-arylalkyl, substituted $C_1$-$C_4$-heteroarylalkyl or it is A as defined in claim 1;

$X^5$ is a leaving group;

L is selected from the group consisting of metal and metal halides; or L is selected from the group consisting of Li and MgX$^6$, wherein X$^6$ is halogen;

LG, LG$^1$, LG$^2$ and LG$^3$ are independent leaving groups; and the other substituents are defined above.

8. The compounds of claim 1, wherein $R^4$ is methyl (methylene).

9. A method for the preparation of a compound having the formula III, IV or V:

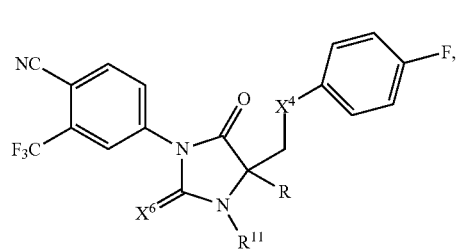

III

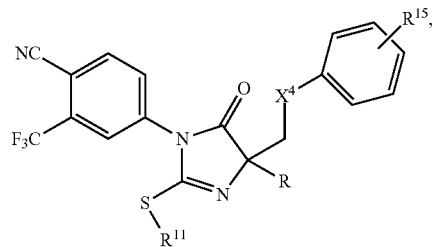

IV

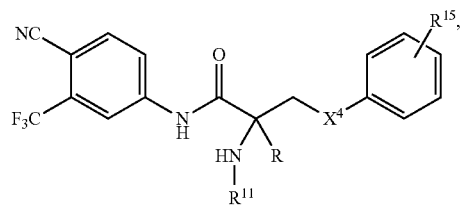

V wherein $X^4$ is O, S, —SO—, —SO$_2$—, —NH— or —NR''— in which R'' is H, $C_1$-$C_4$ alkyl;

R is: H, aryl, optionally substituted aryl, heteroaryl, optionally substituted heteroaryl, straight or branched $C_{1-10}$ alkyl, wherein the alkyl may be substituted with one or more substituents which may be the same or different, and include halo, cycloalkyl containing three to six carbon atoms, hydroxy, alkoxy, amino, acylamino, aroylamino, carboxy, alkoxycarbonyl, aralkyloxycarbonyl;

R is also $C_1$-$C_4$-arylalkyl, $C_{1-4}$ heteroarylalkyl or substituted heterocyclylalkyl;

$R^{11}$ is H, $C_1$-$C_6$ alkyl, substituted $C_1$-$C_6$ alkyl, $C_1$-$C_6$ hetero alkyl, substituted $C_1$-$C_6$ hetero alkyl, aryl, substituted aryl, $C_1$-$C_4$-alkylaryl, hetero aromatic $C_1$-$C_4$ alkyl, aromatic hetero cycle, substituted aromatic hetero cycle, a protecting group or a chiral auxiliary; wherein the protecting group is selected from the group consisting of —COR$^r$, —COOR$^r$, —OSO$_2$R$^r$, —SO$_2$R$^r$, and —SR$^r$; wherein the chiral auxiliar is selected from the group consisting of —OS(O)R$^r$ and —OP(O)R$^s$R$^r$ where R$^r$ and R$^s$ can be the same or different; R$^r$ and R$^s$ are selected from the group consisting of $C_1$-$C_6$ alkyl, $C_1$-$C_6$ halo-alkyl, aryl, substituted aryl, aromatic hetero cycle, and substituted aromatic hetero cycle;

$R^{15}$ is H, halogen, nitro, carboxyl, carbamoyl and cyano, alkyl, alkoxy, alknoyl, alkylthio, alkylsulphinyl, alkylsulphonyl, perfluoroalkyl, perfluoroalkoxy, perfluoroalkylthio, perfluoroalkylsulfinyl, perfluoroalkylsulphonyl, alkoxycarbonyl and N-alkylcarbamoyl, each up to 4 carbon atoms, phenyl, phenylthio, phenylsulfinyl or phenylsulfonyl;

$X^6$ is O or S; and which comprises one of the synthetic procedures reported in scheme 1 or 2:

Scheme 1

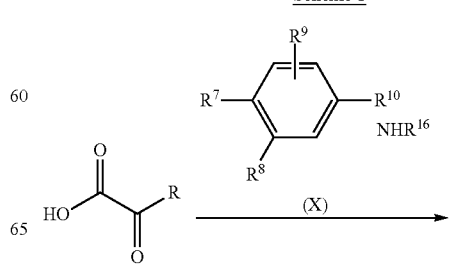

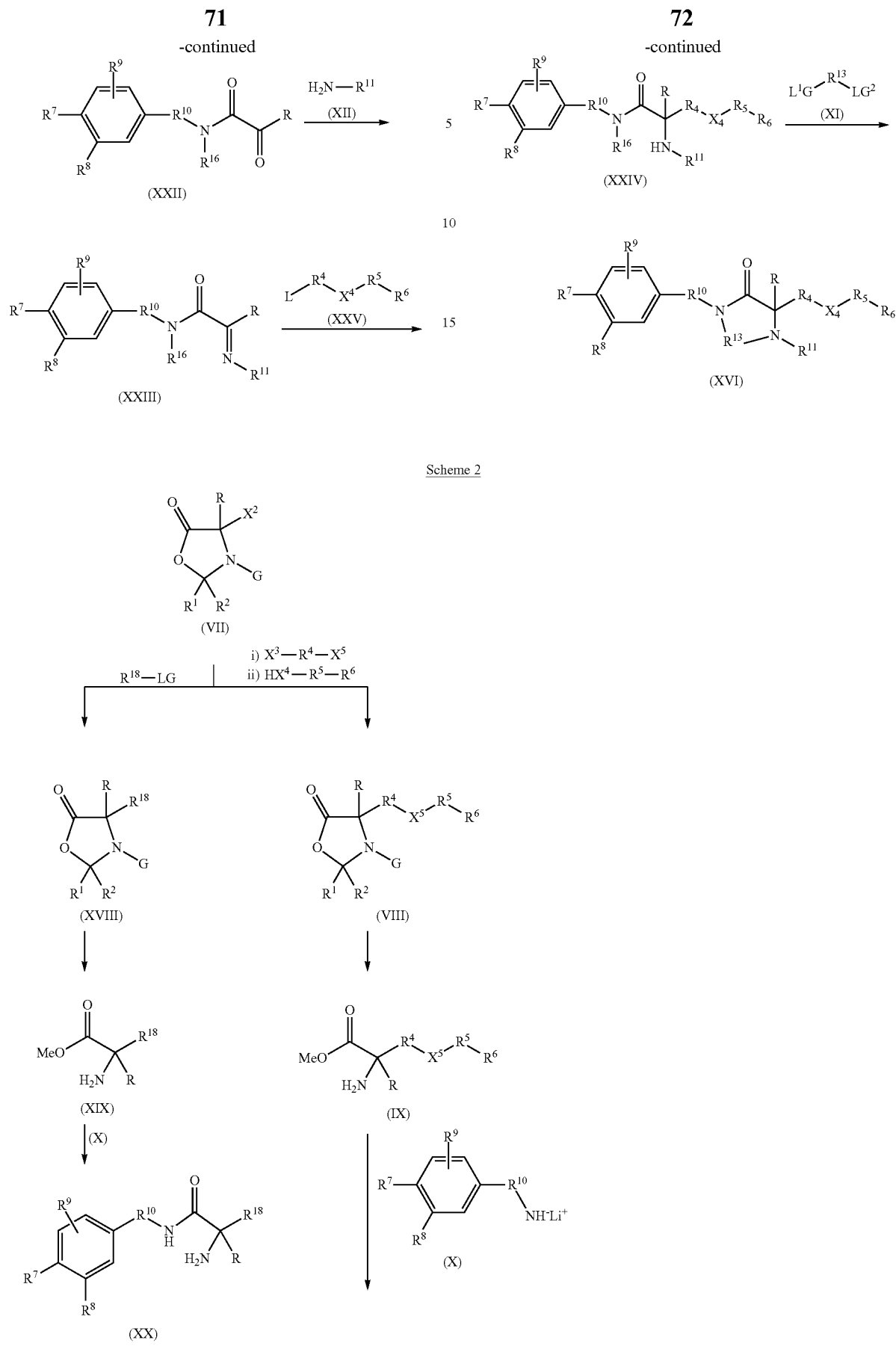

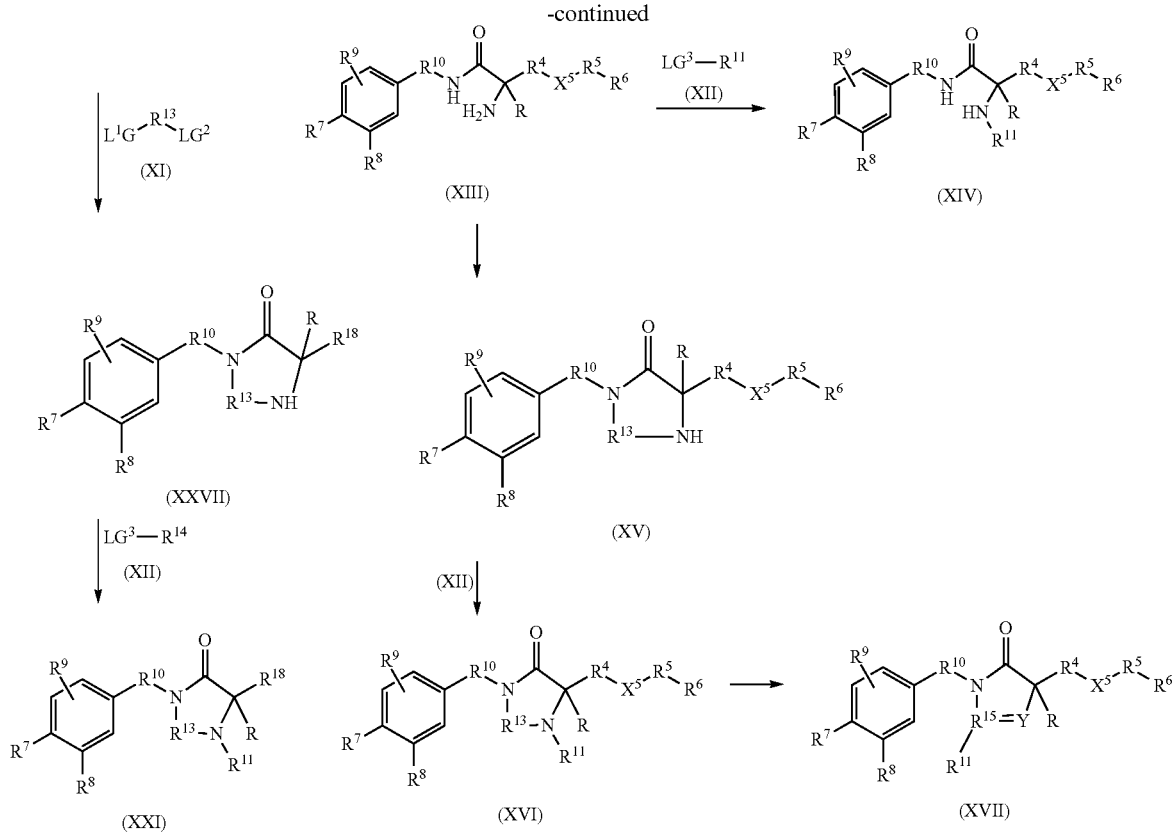

wherein $R^{13}$ is —CO— or —CS—, —SO—, —SO$_2$—, —R$^p$CO—, —R$^p$CS—, —R$^p$SO—, —R$^p$SO$_2$—, wherein R$^p$ is a C$_1$-C$_3$-alkyl;

$R^{15}$ is —C—S—;

$R^{18}$ is aryl, C$_1$-C$_4$-alkyl, C$_1$-C$_4$-heteroalkyl, C$_1$-C$_4$-arylalkyl, C$_1$-C$_4$-heteroarylalkyl, substituted C$_1$-C$_4$-arylalkyl, substituted C$_1$-C$_4$-heteroarylalkyl or it is A as defined in claim 1;

$X^5$ is a leaving group;

L is selected from the group consisting of metal and metal halides; or L is selected from the group consisting of Li and MgX$^6$, wherein X$^6$ is halogen;

LG, LG$^1$, LG$^2$ and LG$^3$ are independent leaving groups; and the other substituents are defined above.

10. A pharmaceutical composition comprising a carrier and the compound according to claim 3, an isomer thereof, a pharmaceutically acceptable salt thereof, a crystal or N-oxide thereof, a hydrate thereof or any combination thereof.

\* \* \* \* \*